(12) United States Patent
Traxlmayr et al.

(10) Patent No.: US 12,102,653 B2
(45) Date of Patent: *Oct. 1, 2024

(54) LIGAND REGULATED PROTEIN-PROTEIN INTERACTION SYSTEM

(71) Applicants: ST. ANNA KINDERKREBSFORSCHUNG, Vienna (AT); UNIVERSITÄT FÜR BODENKULTUR WIEN, Vienna (AT)

(72) Inventors: Michael Traxlmayr, Vienna (AT); Christian Obinger, Vienna (AT); Charlotte Brey, Vienna (AT); Manfred Lehner, Vienna (AT)

(73) Assignees: ST. ANNA KINDERKREBSFORSCHUNG, Vienna (AT); UNIVERSITÄT FÜR BODENKULTUR WIEN, Vienna (AT)

( * ) Notice: Subject to any disclaimer, the term of this patent is extended or adjusted under 35 U.S.C. 154(b) by 0 days.

This patent is subject to a terminal disclaimer.

(21) Appl. No.: 18/312,330

(22) Filed: May 4, 2023

(65) Prior Publication Data
US 2024/0000841 A1 Jan. 4, 2024

Related U.S. Application Data

(63) Continuation of application No. 16/954,914, filed as application No. PCT/EP2018/086299 on Dec. 20, 2018, now Pat. No. 11,844,813.

(30) Foreign Application Priority Data

Dec. 20, 2017 (EP) .................................... 17208924
Mar. 9, 2018 (EP) .................................... 18160863
Oct. 25, 2018 (EP) .................................... 18202544

(51) Int. Cl.
| | | |
|---|---|---|
| *C07K 14/00* | (2006.01) | |
| *A61K 35/17* | (2015.01) | |
| *C07K 14/705* | (2006.01) | |
| *C07K 14/725* | (2006.01) | |
| *C07K 14/775* | (2006.01) | |
| *A61K 38/00* | (2006.01) | |

(52) U.S. Cl.
CPC .......... *A61K 35/17* (2013.01); *C07K 14/7051* (2013.01); *C07K 14/70517* (2013.01); *C07K 14/70521* (2013.01); *C07K 14/775* (2013.01); *A61K 38/00* (2013.01); *C07K 2319/70* (2013.01)

(58) Field of Classification Search
CPC .......... C07K 14/7051; C07K 14/70517; C07K 14/70521; C07K 14/775; C07K 2319/70; A61K 38/00
See application file for complete search history.

(56) References Cited

U.S. PATENT DOCUMENTS

| | | |
|---|---|---|
| 7,723,476 B2 | 5/2010 | Skerra et al. |
| 8,158,753 B2 | 4/2012 | Skerra et al. |
| 8,536,307 B2 | 9/2013 | Skerra et al. |
| 2006/0058510 A1 | 3/2006 | Skerra et al. |
| 2012/0244596 A1 | 9/2012 | Skerra et al. |
| 2017/0081411 A1 | 3/2017 | Engels et al. |
| 2019/0263914 A1 | 8/2019 | Brogdon et al. |

FOREIGN PATENT DOCUMENTS

| | | |
|---|---|---|
| DE | 19742706 A1 | 4/1999 |
| EP | 1017814 B1 | 9/1998 |
| EP | 1270725 B1 | 9/1998 |
| WO | 1999016873 A1 | 4/1999 |
| WO | 2012065978 A1 | 5/2012 |
| WO | 2014127261 A1 | 8/2014 |
| WO | 2015017214 A1 | 2/2015 |
| WO | 2016113203 A1 | 7/2016 |
| WO | 2017032777 A1 | 3/2017 |

OTHER PUBLICATIONS

Heller et al. InChI, the IUPAC International Chemical Identifier. J Cheminform. May 30, 2015; 7:23.*
Voss et al., "Chemically Induced Dimerization: Reversible and Spatiotemporal Control of Protein Function in Cells," Current Opinion in Chemical Biology, vol. 28, Oct. 2015, pp. 194-201 (8 pages).
Derose et al, "Manipulating Signaling at Will: Chemically-inducible Dimerization (CID) Techniques Resolve Problems in Cell Biology," Pflugers Archiv—European Journal of Physiology, vol. 465, No. 3, 2013, pp. 409-417 (14 pages).
Motani et al., "Identification and Characterization of a Non-retinoid Ligand for Retinol-binding Protein 4 Which Lowers Serum Retinol-binding Protein 4 Levels in Vivo," The Journal of Biological Chemistry, vol. 284, Jan. 15, 2009, pp. 7673-7680 (10 pages).
Murzin et al., "SCOP: A Structural Classification of Proteins Database for the Investigation of Sequences and Structures," Journal of Molecular Biology, vol. 247, 1995, pp. 536-540 (5 pages).
Lakshmi et al., "Structure-Based Phylogenetic Analysis of the Lipocalin Superfamily," PLoS One, vol. 10, No. 8: e0135507, Aug. 11, 2015, pp. 1-18 (18 pages).

(Continued)

*Primary Examiner* — Jeanette M Lieb
(74) *Attorney, Agent, or Firm* — Greer, Burns & Crain, Ltd

(57) ABSTRACT

A ligand regulated protein-protein interaction system based on a lipocalin-fold molecule including: (a) a lipocalin-fold molecule; (b) a lipocalin-fold ligand with a low molecular weight of 1500 Da or below; and (c) a lipocalin-fold binding interaction partner, wherein the lipocalin-fold molecule can bind to the lipocalin-fold ligand; and wherein the lipocalin-fold molecule bound to the lipocalin-fold ligand binds to the lipocalin-fold binding interaction partner with an affinity which is at least 10-fold higher than the affinity of the lipocalin-fold molecule not bound to the lipocalin-fold ligand; and wherein the lipocalin-fold binding interaction partner is not a naturally occurring protein which has an affinity of <10 μM to any naturally occurring lipocalin-fold molecule in the presence of any lipocalin-fold ligand.

20 Claims, 29 Drawing Sheets
Specification includes a Sequence Listing.

(56) References Cited

OTHER PUBLICATIONS

Zhang et al., "Retinoid-Binding Proteins: Similar Protein Architectures Bind Similar Ligands via Completely Different Ways," PLoS One, vol. 7, Issue 5: e36772, May 4, 2012, pp. 1-8 (8 pages).
Smathers et al., "The Human Fatty Acid-binding Protein Family: Evolutionary Divergences and Functions," Human Genomics, vol. 5, No. 3, Mar. 2011, pp. 170-191 (22 pages).
Grzyb et al., "Lipocalins—a Family Portrait," Journal of Plant Physiology, vol. 163, Issue 9, Sep. 25, 2006, pp. 895-915 (21 pages).
Flower et al., "The Lipocalin Protein Family: Structural and Sequence Overview," Biochimica et Biophysica Acta (BBA)—Protein Structure and Molecular Enzymology, vol. 1482, Issues 1-2, Oct. 18, 2000, pp. 9-24 (16 pages).
Schiefner et al., "The Menagerie of Human Lipocalins: A Natural Protein Scaffold for Molecular Recognition of Physiological Compounds," Accounts of Chemical Research, 48, Mar. 10, 2015, pp. 976-985 (10 pages).
Skerra, "Lipocalins as a Scaffold," Biochimica et Biophysica Acta (BBA), vol. 1482, Issues 1-2, Oct. 18, 2000, pp. 337-350 (14 pages).
Korndörfer, "Crystallographic Analysis of an "Anticalin" with Tailored Specificity for Fluorescein Reveals High Structural Plasticity of the Lipocalin Loop Region," Proteins, vol. 53, Issue 1, Oct. 2003, pp. 121-129 (9 pages).
Korndörfer et al., "Structural Mechanism of Specific Ligand Recognition by a Lipocalin Tailored for the Complexation of Digoxigenin," Journal of Molecular Biology, vol. 330, Issue 2, 2003, pp. 385-396 (12 pages).
Kim et al., "High-Affinity Recognition of Lanthanide (III) Chelate Complexes by a Reprogrammed Human Lipocalin 2," Journal of the American Chemical Society, 131 (10), Feb. 19, 2009, pp. 3565-3576 (12 pages).
Schlehuber et al., "Tuning Ligand Affinity, Specificity, and Folding Stability of an Engineered Lipocalin Variant—a So-Called 'Anticalin'—Using A Molecular Random Approach," Biophysical Chemistry, vol. 96, Issues 2-3, May 2, 2002, pp. 213-228 (16 pages).
Richter, "Anticalins: Exploiting a Non-Ig Scaffold with Hypervariable Loops for the Engineering of Binding Proteins," FEBS Letters, vol. 588, Issue 2, Jan. 21, 2014, pp. 213-218 (6 pages).
Schonfeld et al., "An Engineered Lipocalin Specific for CTLA-4 Reveals a Combining Site with Structural and Conformational Features Similar to Antibodies," Proceedings of the National Academy of Sciences of the USA, vol. 106, No. 20, May 19, 2009, pp. 8198-8203 (6 pages).
Gebauer et al., "Combinatorial Design of an Anticalin Directed Against the Extra-Domain B for the Specific Targeting of Oncofetal Fibronectin," Journal of Molecular Biology, vol. 425, Issue 4, Feb. 22, 2013, pp. 780-802 (23 pages).
Barinka et al., "Selection and Characterization of Anticalins Targeting Human Prostate-specific Membrane Antigen (PSMA)," Protein Engineering, Design & Selection, 2016, vol. 29, No. 3, Jan. 21, 2016, pp. 105-115 (11 pages).
Jones et al., "Improving the Safety of Cell Therapy Products by Suicide Gene Transfer," Frontiers in Pharmacology, vol. 5, Article 254, Nov. 27, 2014, pp. 1-8 (8 pages).
Sun et al., "The Quest for Spatio-Temporal Control of CAR T Cells," Cell Research, vol. 25, Nov. 17, 2015, pp. 1281-1282 (2 pages).
Sergeeva et al., "Display Technologies: Application for the Discovery of Drug and Gene Delivery Agents," Advanced Drug Delivery Reviews, vol. 58, 2006, pp. 1622-1654 (33 pages).
Rutkowska et al., "Protein Tango: The Toolbox to Capture Interacting Partners," Angewandte Chemie International Edition, vol. 51, 2012, pp. 8166-8176 (11 pages).
Papiz et al., "The structure of β-lactoglobulin and its Similarity to Plasma Retinol-binding Protein," Nature, vol. 324, Nov. 27, 1986, pp. 383-385 (3 pages).

Spinelli et al., "Boar Salivary Lipocalin, Three-dimensional X-ray Structure and Androstenol/Androstenone Docking Simulations," European Journal of Biochemistry, FEBS Journal, vol. 269, 2002, pp. 2449-2456 (8 pages).
Sevvana et al., "Mouse ApoM Displays an Unprecedented Seven-Stranded Lipocalin Fold: Folding Decoy or Alternative Native Fold?" Journal of Molecular Biology, vol. 404, 2010, pp. 363-371 (9 pages).
Berni et al., "In Vitro Interaction of Fenretinide with Plasma Retinol-Binding Protein and its Functional Consequences," FEBS Letters, vol. 308, No. 1, Aug. 1992, pp. 43-45 (3 pages).
Zanotti et al., "The Interaction of N-ethyl Retinamide with Plasma Retinol-binding Protein (RBP) and the Crystal Structure of the Retinoid-RBP Complex at 1.9-A Resolution," Journal of Biological Chemistry, vol. 268, No. 33, Nov. 25, 1993, pp. 24873-24879 (7 pages).
Zanotti et al., "Crystallographic Studies on Complexes Between Retinoids and Plasma Retinol-binding Protein," The Journal of Biological Chemistry, vol. 26, No. 47, Nov. 25, 1994, pp. 29613-29620 (8 pages).
Pattanayek et al., "Protein and Ligand Adaptation in a Retinoic Acid Binding Protein," Protein Science, 1999, 8, pp. 2027-2032 (6 pages).
Gasymov et al., "Structural Changes in Human Tear Lipocalins Associated with Lipid Binding," Biochimica et Biophysica Acta (BBA), vol. 1386, Apr. 10, 1998, pp. 145-156 (12 pages).
Breustedt et al., "A New Crystal Form of Human Tear Lipocalin Reveals High Flexibility in the Loop Region and Induced Fit in the Ligand Cavity," Acta Crystallographica Section D, Biological Crystallography, D65, Aug. 4, 2009, pp. 1118-1125 (8 pages).
Gasymov et al., "Cation-πInteractions in Lipocalins: Structural and Functional Implications," Biochemistry, 51, 14, Apr. 10, 2012, pp. 2991-3002 (25 pages).
Zhang et al., "Binding Characteristics of Sphingosine-1-Phosphate to ApoM Hints to Assisted Release Mechanism via the ApoM Calyx-Opening," Scientific Reports, vol. 6, Article No. 30655, Aug. 1, 2016, pp. 1-12 (12 pages).
Christoffersen et al., "Endothelium-protective Sphingosine-1-phosphate Provided by HDL-Associated Apolipoprotein M," Proceedings of the National Academy of Sciences of the USA, vol. 108, No. 23, Jun. 7, 2011, pp. 9613-9618 (14 pages).
Redondo et al., "Identification of the Retinol-binding Protein (RBP) Interaction Site and Functional State of RBPs for the Membrane Receptor," The FASEB Journal, Research Communication, vol. 22, No. 4, Apr. 2008, pp. 1043-1054 (13 pages).
Coward et al., "Application of an Allosteric Model to Describe the Interactions Among Retinol Binding Protein 4, Transthyretin and Small Molecule Retinol Binding Protein 4 Ligands," Analytical Biochemistry, vol. 384, 2009, pp. 312-320 (9 pages).
Sharif et al., "Time-resolved Fluorescence Resonance Energy Transfer and Surface Plasmon Resonance-based Assays for Retinoid and Transthyretin Binding to Retinol-binding Protein 4," Analytical Biochemistry, vol. 392, May 29, 2009, pp. 162-168 (7 pages).
Bao et al., "The Ligands of Neutrophil Gelatinase-associated Lipocalin," RSC Adv., 5 (126), 2015, pp. 104363-104374 (20 pages).
Eggenstein et al., "Structure-guided Engineering of Anticalins with Improved Binding Behavior and Biochemical Characteristics for Application in Radio-immuno Imaging and/or Therapy," Journal of Structural Biology, vol. 185, 2014, pp. 203-214 (12 pages).
Gasymov et al., "The Conserved Disulfide Bond of Human Tear Lipocalin Modulates Conformation and Lipid Binding in a Ligand Selective Manner," Biochimica et Biophysica Acta (BBA)—Proteins and Proteomics, vol. 1814, Mar. 29, 2011, pp. 671-683 (13 pages).
Schmidt, "Untersuchungen zur Proteinfaltung durch Protein-Design am Retinol-Bindungsprotein," München: Herbert Utz Verlag, vol. ISBN 3-89675-314-2, 1998 (6 pages).
Whitehead et al., "Computational Design of Novel Protein Binders and Experimental Affinity Maturation," Methods in Enzymology, vol. 523, 2013, pp. 1-19 (19 pages).
Strauch et al., "Computational Design of a pH-sensitive IgG Binding Protein," Proceedings of the National Academy of Sciences of the USA, vol. 111, No. 2, Jan. 14, 2014, pp. 675-680 (6 pages).

(56) References Cited

OTHER PUBLICATIONS

Worn et al., "Correlation Between in Vitro Stability and in Vivo Performance of Anti-GCN4 Intrabodies as Cytoplasmic Inhibitors," The Journal of Biological Chemistry, vol. 275, No. 4, Jan. 28, 2000, pp. 2795-2803 (10 pages).
Traxlmayr et al., "Directed Evolution of Stabilized IgG1-Fc Scaffolds by Application of Strong Heat Shock to Libraries Displayed on Yeast," Biochimica et Biophysica Acta (BBA)—Proteins and Proteomics, vol. 1824, Apr. 2012, pp. 542-549 (8 pages).
Hotamisligil et al., "Metabolic Functions of FABPs—Mechanisms and Therapeutic Implications," Nature Reviews Endocrinology, vol. 11, Oct. 2015, pp. 592-605 (14 pages).
Curto et al., "Δ98Δ, a Minimalist Model of Antiparallel β-sheet Proteins Based on Intestinal Fatty Acid Binding Protein," Protein Science, vol. 18, Jan. 22, 2009, pp. 735-746 (12 pages).
Ogbay et al., "The NMR Structure of a Stable and Compact all-β-sheet Variant of Intestinal Fatty Acid-binding Protein," Protein Science, vol. 13, Feb. 10, 2004, pp. 1227-1237 (11 pages).
Yu et al., "Coexistence of Multiple Minor States of Fatty Acid Binding Protein and Their Functional Relevance," Scientific Reports, vol. 6, Article 34171, Sep. 28, 2016, pp. 1-8 (8 pages).
Sharma et al., "Fatty Acid Induced Remodeling Within the Human Liver Fatty Acid-binding Protein," The Journal of Biological Chemistry, vol. 286, No. 36, Sep. 9, 2011, pp. 31924-31928 (6 pages).
Cai et al., "Solution Structure and Backbone Dynamics of Human Liver Fatty Acid Binding Protein: Fatty Acid Binding Revisited," Biophysical Journal, vol. 102, Issue 11, Jun. 2012, pp. 2585-2594 (10 pages).
Franzoni et al., "New Insights on the Protein-ligand Interaction Differences Between the Two Primary Cellular Retinol Carriers[s]," The Journal of Lipid Research, vol. 51, 2010, pp. 1332-1343 (12 pages).
Vaezeslami et al., "The Structure of Apo-wild-type Cellular Retinoic Acid Binding Protein II at 1.4 Å and its Relationship to Ligand Binding and Nuclear Translocation," Journal of Molecular Biology, vol. 363, 2006, pp. 687-701 (15 pages).
Gillilan et al., "Structural Basis for Activation of Fatty Acid-binding Protein 4," Journal Molecular Biology, vol. 372, 2007, pp. 1246-1260 (15 pages).
Menozzi et al., "Structural and Molecular Determinants Affecting the Interaction of Retinol with Human CRBP1," Journal of Structural Biology, vol. 197, 2017, pp. 330-339 (10 pages).
Long et al., "Millisecond Timescale Dynamics of Human Liver Fatty Acid Binding Protein: Testing of Its Relevance to the Ligand Entry Process," Biophysical Journal, vol. 98, Jun. 2010, pp. 3054-3061 (8 pages).
Armstrong et al., "Structural Basis for Ligand Regulation of the Fatty Acid-binding Protein 5, Peroxisome Proliferator-activated Receptor β/δ(FABP5-PPAR β/δ) Signaling Pathway," The Journal of Biological Chemistry, vol. 289, No. 21, May 23, 2014, p. 14941-14954 (15 pages).
Amber-Vitos et al., "The Interaction of FABP with Kapα," PLoS One, Aug. 18, 2015, e0132138, pp. 1-24 (24 pages).
Berry et al., "Cross Talk Between Signaling and Vitamin A Transport by the Retinol-Binding Protein Receptor STRA6," Molecular and Cellular Biology, vol. 32, No. 15, Aug. 2012, pp. 3164-3175 (12 pages).
Sessler et al., "A Ligand-Activated Nuclear Localization Signal in Cellular Retinoic Acid Binding Protein-II," Molecular Cell, vol. 18, Apr. 29, 2005, pp. 343-353 (11 pages).
Hofer et al., "Fatty Acid-binding Proteins Interact with Comparative Gene Identification-58 Linking Lipolysis with Lipid Ligand Shuttling," The Journal of Biological Chemistry, vol. 290, No. 30, Jul. 24, 2015, pp. 18438-18453 (17 pages).
Furuhashi et al., "Fatty Acid-binding Proteins: Role in Metabolic Diseases and Potential as Drug Targets," Nature Reviews, Drug Discovery, vol. 7, Jun. 2008, pp. 489-503 (15 pages).
Velkov T. et al., "Examination of the Role of Intestinal Fatty Acid-Binding Protein in Drug Absorption Using a Parallel Artificial Membrane Permeability Assay," Chemistry & Biology, vol. 14, Apr. 2007, pp. 453-465 (13 pages).
Velkov T., "Interactions Between Human Liver Fatty Acid Binding Protein and Peroxisome Proliferator Activated Receptor Selective Drugs," PPAR Research, vol. 2013, Article ID 938401, Nov. 23, 2012, pp. 1-14 plus final page (15 pages).
Beringhelli et al., "All-Purpose Containers? Lipid-Binding Protein—Drug Interactions," PLoS One, Jul. 13, 2015, e0132096, pp. 1-22 (22 pages).
Chuang et al., "Characterization of the Drug Binding Specificity of Rat Liver Fatty Acid Binding Protein," Journal of Medical Chemistry, vol. 51, Jun. 6, 2008, pp. 3755-3764 (10 pages).
Dobri et al., "A1120, a Nonretinoid RBP4 Antagonist, Inhibits Formation of Cytotoxic Bisretinoids in the Animal Model of Enhanced Retinal Lipofuscinogenesis," Investigative Ophthalmology & Visual Science, vol. 54, No. 1, Jan. 2013, pp. 85-95 (11 pages).
Cioffi et al., "Design, Synthesis, and Evaluation of Nonretinoid Retinol Binding Protein 4 Antagonists for the Potential Treatment of Atrophic Age-Related Macular Degeneration and Stargardt Disease," Journal of Medicinal Chemistry, vol. 57, Sep. 1, 2014, pp. 7731-7757 (27 pages).
Cioffi et al., "Bicyclic [3.3.0]-Octahydrocyclopenta[c]pyrrolo Antagonists of Retinol Binding Protein 4: Potential Treatment of Atrophic Age-Related Macular Degeneration and Stargardt Disease," Journal of Medicinal Chemistry, vol. 58, Jul. 16, 2015, pp. 5863-5888 (26 pages).
Auld et al., "Receptor Binding Assays for HTS and Drug Discovery," Assay Guidance Manual, Oct. 1, 2012, pp. 1-49 (49 pages).
Sittampalam et al., "Assay Guidance Manual," Feb. 1, 2020, pp. 1-1247 (1247 pages (split into 2 parts: Part 1: 633 pages; Part 2: 634 pages).
Qing et al., "Pharmacophore Modeling: Advances, Limitations, and Current Utility in Drug Discovery," Journal of Receptor, Ligand and Channel Research, vol. 2014:7, Nov. 11, 2014, pp. 81-92 (12 pages).
Simeon et al., "In Vitro-engineered Non-antibody Protein Therapeutics," Protein & Cell, Feb. 13, 2017 (12 pages).
Gilbreth et al., "Structural Insights for Engineering Binding Proteins Based on Nonantibody Scaffolds," Current Opinion in Structural Biology 2012, vol. 22, pp. 413-420 (8 pages).
Koide et al., "The Importance of Being Tyrosine: Lessons in Molecular Recognition from Minimalist Synthetic Binding Proteins," ACS Chemical Biology, vol. 4, Issue 5, May 15, 2009, pp. 1-16 (16 pages).
Traxlmayr et al., "Strong Enrichment of Aromatic Residues in Binding Sites from a Charge-neutralized Hyperthermostable Sso7d Scaffold Library," The Journal of Biological Chemistry, vol. 291, No. 43, Oct. 21, 2016, pp. 22496-22508 (14 pages).
Plückthun, "Alternative Scaffolds: Expanding the Options of Antibodies," In: Recombinant Antibodies for Immunotherapy, Melvyn Little, Cambridge University Press, New York, 2009, pp. 243-271 (29 pages).
Chapman et al., "Scratching the Surface: Resurfacing Proteins to Endow New Properties and Function," Cell Chemical Biology, vol. 23, May 19, 2016, pp. 543-553 (11 pages).
Binz et al., "Engineering Novel Binding Proteins from Nonimmunoglobulin Domains," Nature Biotechnology, vol. 23, No. 10, Oct. 2005, pp. 1257-1268 (12 pages).
Vazquez-Lombardi et al., "Challenges and Opportunities for Non-antibody Scaffold Drugs," Drug Discovery Today, vol. 20, No. 10, Oct. 2015, pp. 1271-1283 (13 pages).
Abate-Daga et al., "CAR Models: Next-generation CAR Modifications for Enhanced T-cell Function," Molecular Therapy-Oncolytics, vol. 3, 160143, 2016, pp. 1-7 (7 pages).
Milone et al., "Chimeric Receptors Containing CD137 Signal Transduction Domains Mediate Enhanced Survival of T Cells and Increased Antileukemic Efficacy In Vivo," Molecular Therapy, vol. 17, No. 8, Aug. 2009, pp. 1453-1464 (12 pages).
Gaj et al., "ZFN, Talen, and CRISPR/Cas-based Methods for Genome Engineering," Trends in Biotechnology, vol. 31, No. 7., Jul. 2013, pp. 397-405 (9 pages).

(56) References Cited

OTHER PUBLICATIONS

Ren et al., "Advancing Chimeric Antigen Receptor T Cell Therapy with CRISPR/Cas9," Protein & Cell, 2017, 8, (9), pp. 634-643 (10 pages).

Eyquem et al., "Targeting a CAR to the TRAC Locus with CRISPR/Cas9 Enhances Tumour Rejection," Nature, vol. 543, Mar. 2, 2017, pp. 113-117 (plus 14 pages) (19 pages).

Chen et al., "Engineering Fibronectin-Based Binding Proteins by Yeast Surface Display," Methods in Enzymology, vol. 523, 2013, pp. 303-326 (24 pages).

Wysocka-Kapcinska et al., "Expression and Characterization of Recombinant Human Retinol-binding Protein in Pichia Pastoris," Protein Expression and Purification, vol. 71, 2010, pp. 28-32 (5 pages).

Hackel et al., "Stability and CDR Composition Biases Enrich Binder Functionality Landscapes," Journal of Molecular Biology, vol. 401, Jun. 1, 2010, pp. 84-96 (13 pages).

Chao et al., "Isolating and Engineering Human Antibodies Using Yeast Surface Display," Nature Protocols, vol. 1, No. 2, 2006, pp. 755-768 plus Erratum (15 pages).

Angelini et al., "Protein Engineering and Selection Using Yeast Surface Display," Methods in Molecular Biology, vol. 1319, 2015, pp. 3-36 (34 pages).

Jadoon, A., et al., "Regulation of fatty acid binding proteins by hypoxia inducible factors 1α and 2α in the placenta: Relevance to pre-eclampsia", Prostaglandins, Leukotrienes and Essential Fatty Acids, Feb. 2015, pp. 25-29.

Japanese Office Action dated Jan. 10, 2023 for Japanese Patent Application No. 2020-535059.

Colantuoni et al., Nucleic Acids Research, "Qoning and sequencing of a full length cDNA coding for human retinol-binding protein", Nov. 25, 1983, pp. 7769-7776, vol. 11, No. 22.

Canadian Office Action dated Oct. 27, 2023 for Canadian Patent Application No. 3,086,032.

Schiefner, A., et al., "The Menagerie of Human Lipocalins: A Natural Protein Scaffold for Molecular Recognition of Physiological Compounds", Accounts of Chemical Research, Mar. 10, 2015, pp. 976-985, vol. 48.

Korndorfer, I., et al., "Crystallographic Analysis of an "Anticalin" With Tailored Specificity for Fluorescein Reveals High Structural Plasticity of the Lipocalin Loop Region", Proteins: Structure, Function, and Bioinformatics, Apr. 30, 2003, pp. 121-129, No. 53.

Korndorfer, I., et al., "Structural Mechanism of Specific Ligand Recognition by a Lipocalin Tailored for the Complexationof Digoxigenin", J. Mol. Biol, (2003), pp. 385-396, vol. 330.

Kim, S., et al., Secretome analysis of differentially induced proteins in rice suspension-cultured cells triggered by rice blast fungus and elicitor, Proteomics, 2009, pp. 1302-1313, vol. 9.

Flower, D., et al., "The lipocalin protein family: structural and sequence overview", Biochimica et Biophysica Acta, (2000) pp. 9-24, vol. 1482.

Beste, G., et al., "Small antibody-like proteins with prescribed ligand specificities derived from the lipocalin fold", Proc. Natl. Acad. Sci., Mar. 1999, pp. 1898-1903, vol. 96.

\* cited by examiner

A
Fig. 1
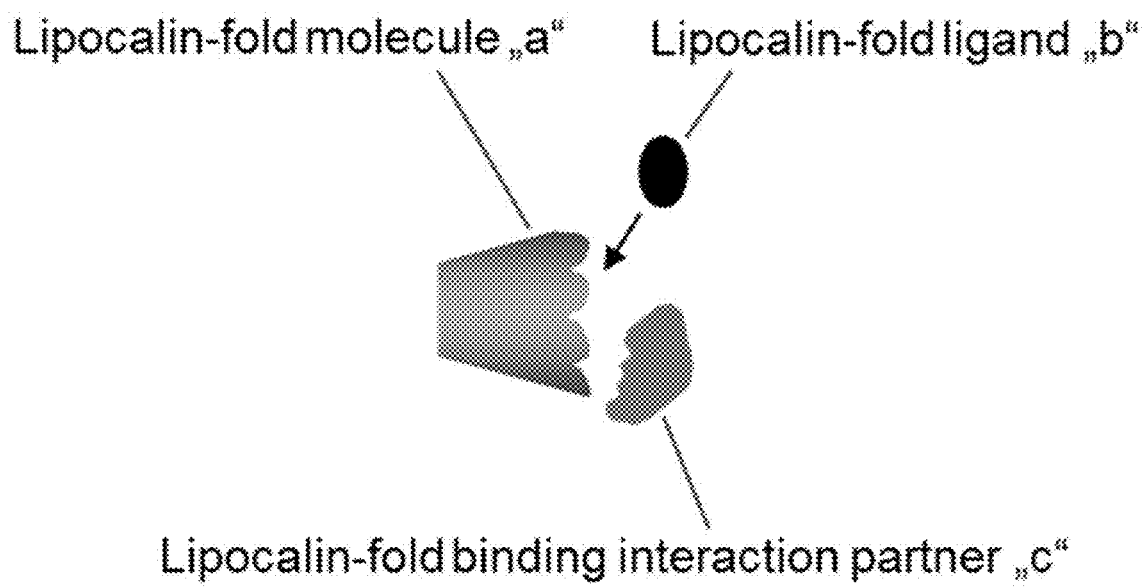
B
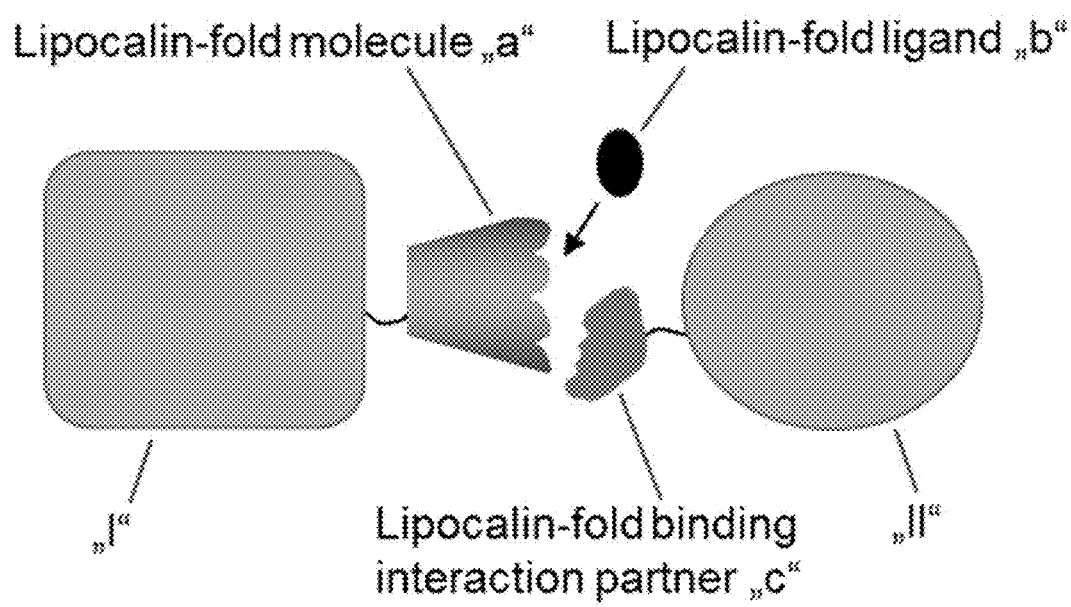

Fig. 5A rcSso7d: 61 amino acids

ATVKFTYQGEEKQVDISKIKWVIRWGQHIAFKYDEGGGAAGYGWVSEKDAPKELLQMLEKQ

RS1:

GCAACCGTGAAATTCACATACCAAGGCGAAGAAGAACAGGTGGATATTAGCAAAATCAAGAAAGTGGCTCGT
TACGGCCAGAACATTTACTTTTCTTATGATGAAGGTGGTGGTGCCTGGGATTATGGTGGCGTGAGCGAAAAAG
ATGCACCGAAAGAACTGCTGCAGATGCTGGAAAAGCAA

ATVKFTYQGEE*Q*VDISKI*K*A*Y*G*N*Y*SYDEGGGA*G*GVSEKDAPKELLQMLEKQ

RS2:

GCAACCGTGAAACTCACATACCAAGGCGAAGAAAAACAGGTGGATATTAGCAAAATCAAGCGTGTGGCTCGT
TACGGCCAGGGTATTTACTTTGACTATGGTGAAGGTGGTGGTGCCTGGGGTTACGGTAGCGTGAGCGAAAAA
GATGCACCGAAAGAACTGCTGCAGATGCTGGAAAAGCAA

ATVK*F*TYQGEEKQVDISKI*R*A*Y*G*G*Y*DYGEGGGA*G*SVSEKDAPKELLQMLEKQ

RS3:

GCAACCGTGAAACTCACATACCAAGGCGAAGAAAAACAGGTGGATATTAGCAAAATCAAGCGTGTGGCTCGT
TACGGCCAGAACATTTACTTTTCTTATGATGAAGGTGGTGGTGCCTATGATTATGGTGCAGTGAGCGAAAAAG
ATGCACCGAAAGAACTGCTGCAGATGCTGGAAAAGCAA

ATVK*F*TYQGEEKQVDISKI*R*A*Y*G*N*Y*SY*E*GGGA*G*AVSEKDAPKELLQMLEKQ

RS4:

GCAACCGCGAAATTCACATACCAAGGCGAAGAAAAACAGGTGGATATTAGCAAAATCAAGCGCGTGGCTCGT
TACGGCCAGGGTATTTACTTTTCTTATGATGAAGGTGGTGGTGCCTATGGTTATGGTAGCGTGAGCGAAAAAG
ATGCACCGAAAGAACTGCTGCAGATGCTGGAAAAGCAA

AT*A*KFTYQGEEKQVDISKI*R*A*Y*G*G*Y*SYDEGGGA*G*SVSEKDAPKELLQMLEKQ

RS5: GCAACCGTGAAATTCACATACCAAGGCGAAGAAAAACAGGTGGATATTAGCAAAATCAAGCGTGTGGCTCGT
TACGGCCAGGGTATTTACTTTGACTATGGTGAAGGTGGTGGTGCCTGGGGTTACGGTAGCGTGAGCGAAGAA
GATGCACCGAAAGAACTGCTGCAGATGCTGGAAAAGCAA

ATVKFTYQGEEKQVDISKIK*V*R*GQ*I*F*Y*EGGGA*G*G*VSE*DAPKELLQMLEKQ

Fig. 5B

FN3 wild type: 102 amino acids
VSDVPRDLEVVAATPTSLLISWDAPAVTVRYYRITYGETGGNSPVQEFTVPGSKSTATISGLKPGVDYTITVYAV
TGRGDSPASSKPISINYRTEIDKPSQ

RF1
GTTTCTGATGTTCCGAGGGACCTGGAAGTTGTTGCTGCGACCCCCACCAGCCTACTGATCAGCTGGTAT
TATCC
CAACGCTAGTCATGCGGGTTATTACAGGGTCACTTACGGAGAAACAGGAGGAAATAGCCCTGTCCAG
GAGTT
CACTGTGCCTTTCTCTATTCGGTATACTATTGCTACCATCAGCGGCCTTAAACCTGGAGTTGATCATACCA
TCAC
TGTGTATGCTGTCACTGACTACGCCTATTACTACCGCTCGTCTGAGCCAATTTCCATTAATTACCGAACA
GAAAT TGACAAACCATCCCAGG

VSDVPRDLEVVAATPTSLLISW░░░░░░░YR░TYGETGGNSPVQEFTVP░░░░T░ATISGLKPGVD░TITV
YAVT░░░░░░░PISINYRTEIDKPSQ

RF2
GTTTCTGATGTTCCGAGGGACCTGGAAGTTGTTGCTGCGACCCCCACCAGCCTACTGATCAGCTGGTAT
TATCC
CAACGCTAGTCATGCGGGTTATTACAGGATCACTTACGGAGAAACAGGAGGAAATAGCCCTGTCCAGG
AGTTC
ACTGTGCCTTTCTCTATTCGGTATACTATTGCTACCATCAGCGGCCTTAAACCTGGAGTTGATTATACCAT
CACT
GTGTATGCTGTCACTGACTACGCCTATTACTACCGCTTGTCTGAGCCAATTTCCATTAATTACCGAACAG
AAATT GACAAACCATCCCAGG

VSDVPRDLEVVAATPTSLLISW░░░░░░░YRITYGETGGNSPVQEFTVP░░░░T░ATISGLKPGVDYTITV
YAVT░░░░░░░PISINYRTEIDKPSQ

RF3
GTTTCTGATGTTCCGAGGGACCTGGAAGTTGTTGCTGCGACCCCCACCAGCCTACTGATCAGCTGGTAT
TATCC
CAACGCTAGTCATGCGGGTTATTACAGGATCACTTACGGAGAAACAGGAGGAAATAGCCCTGTCCAGG
AGTTC
ACTGTGCCTTTCTCTATTCGGTATACTATTGCTACCATCAGCGGCCTTAAACCTGGAGTTGATTATACCAT
CACT
GTGTATGCTGTCACTGCCAGTTGTCAGTATTGCTCTTATCCAATTTCCATTAATTACCGAACAGAAATTG
ACAAA CCATCCCAGG

VSDVPRDLEVVAATPTSLLISW░░░░░░░YYRITYGETGGNSPVQEFTVP░░░░T░ATISGLKPGVDYTITV
YAVT░░░░░PISINYRTEIDKPSQ

Fig. 6A
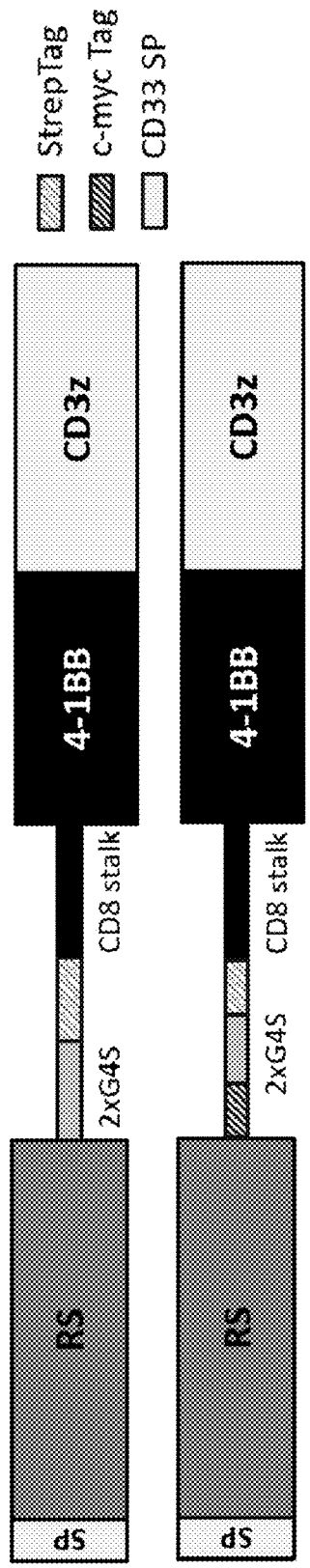
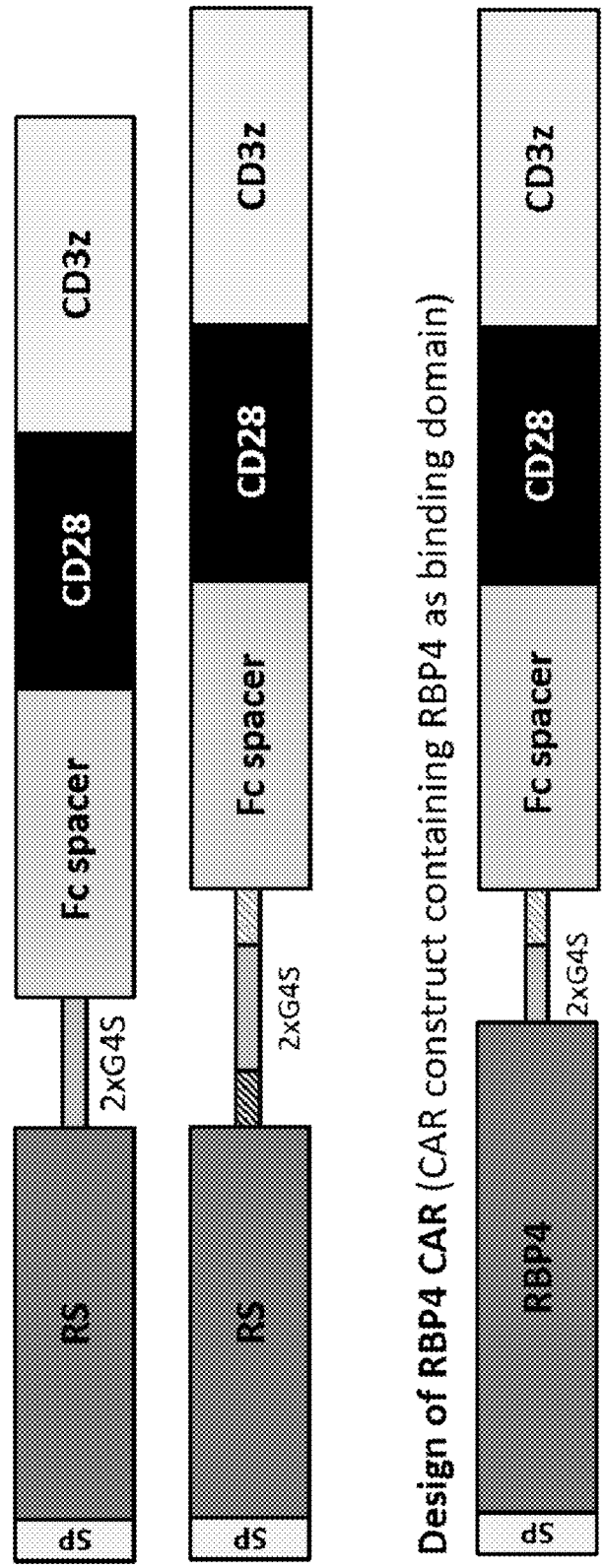

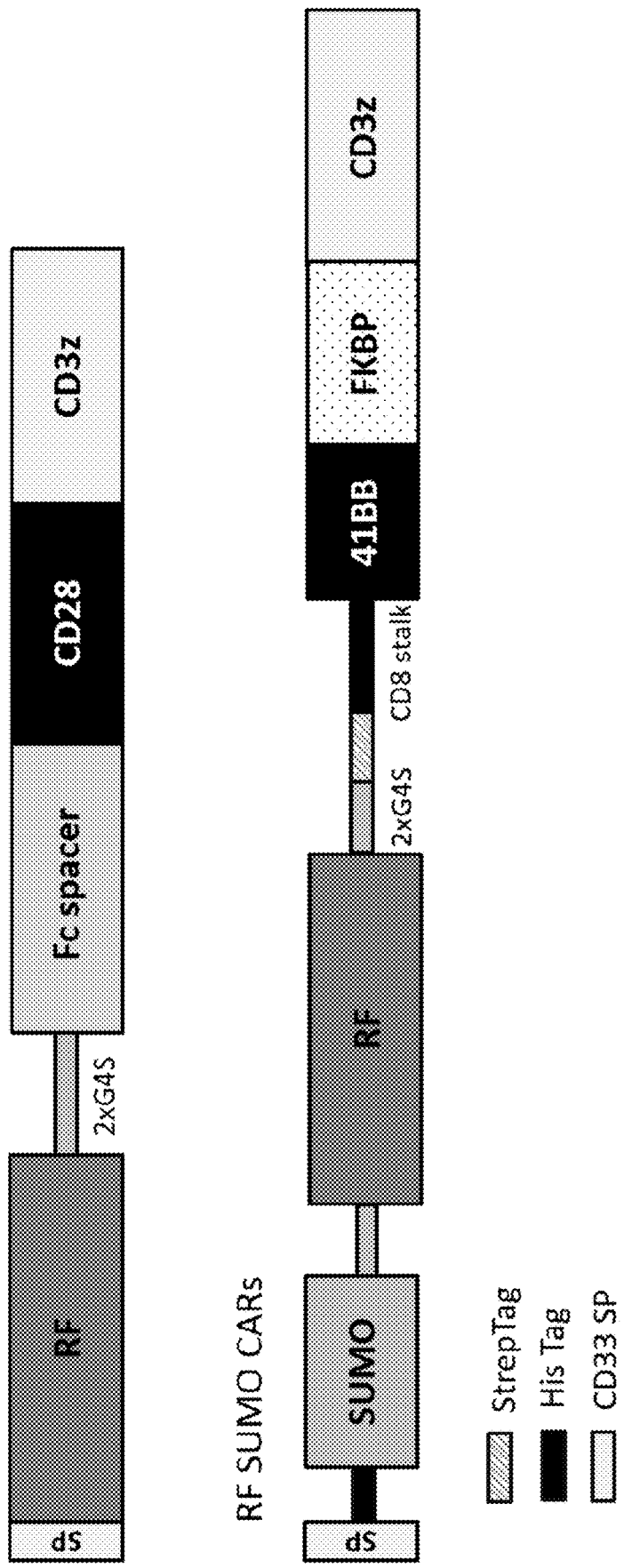

Fig. 7A

Underlined text = signal peptide
Underlined (bold) text = rcSso7d-based RBP4 binder
Dark grey text = c-myc Tag
Underlined (dotted) text = 2x G4S linker
Underlined text = Strep Tag
Bold text = CD8 stalk
*Italic text* = Fc spacer
Light grey = CD28 co-stimulatory domain
Underlined (dotted) text = 41BB domain
Underlined (double) text = CD3 zeta signalling domain RS1 short CAR:

MPLLLLLPLLWAGALAMATVKFTYQGEEEQVDISKIKKVARYGQNIYFSY
DEGGGAWDYGGVSEKDAPKELLQMLEKQGGGGSGGGGSNWSHPQFEK**TTTPAPRPPTPAP
TIASQPLSLRPEACRPAAGGAVHTRGLDFACD**IYIWAPLAGTCGVLLLSLVITLYCKRGR
KKLLYIFKQPFMRPVQTTQEEDGCSCRFPEEEEGGCELRVKFSRSADAPAYKQGQNQLYN
ELNLGRREEYDVLDKRRGRDPEMGGKPRRKNPQEGLYNELQKDKMAEAYSEIGMKGERRR
GKGHDGLYQGLSTATKDTYDALHMQALPPR

RS2 short CAR:

MPLLLLLPLLWAGALAMATVKLTYQGEEKQVDISKIKRVARYGQGIYFDY
GEGGGAWGYGSVSEKDAPKELLQMLEKQGGGGSGGGGSNWSHPQFEK**TTTPAPRPPTPAP
TIASQPLSLRPEACRPAAGGAVHTRGLDFACD**IYIWAPLAGTCGVLLLSLVITLYCKRGR
KKLLYIFKQPFMRPVQTTQEEDGCSCRFPEEEEGGCELRVKFSRSADAPAYKQGQNQLYN
ELNLGRREEYDVLDKRRGRDPEMGGKPRRKNPQEGLYNELQKDKMAEAYSEIGMKGERRR
GKGHDGLYQGLSTATKDTYDALHMQALPPR

RS3 short CAR:

MPLLLLLPLLWAGALAMATVKLTYQGEEKQVDISKIKRVARYGQNIYFSY
DEGGGAYDYGAVSEKDAPKELLQMLEKQGGGGSGGGGSNWSHPQFEK**TTTPAPRPPTPAP
TIASQPLSLRPEACRPAAGGAVHTRGLDFACD**IYIWAPLAGTCGVLLLSLVITLYCKRGR
KKLLYIFKQPFMRPVQTTQEEDGCSCRFPEEEEGGCELRVKFSRSADAPAYKQGQNQLYN
ELNLGRREEYDVLDKRRGRDPEMGGKPRRKNPQEGLYNELQKDKMAEAYSEIGMKGERRR
GKGHDGLYQGLSTATKDTYDALHMQALPPR

Fig. 7B

RS3 c-myc short CAR:

MPLLLLLPLLWAGALAMATVKLTYQGEEKQVDISKIKRVARYGQNIYFSY
DEGGGAYDYGAVSEKDAPKELLQMLEKQEQKLISEEDLGGGGSGGGGSNWSHPQFEK**TTT
PAPRPPTPAPTIASQPLSLRPEACRPAAGGAVHTRGLDFACD**IYIWAPLAGTCGVLLLSL
VITLYCKRGRKKLLYIFKQPFMRPVQTTQEEDGCSCRFPEEEEGGCELRVKFSRSADAPA
YKQGQNQLYNELNLGRREEYDVLDKRRGRDPEMGGKPRRKNPQEGLYNELQKDKMAEAYS
EIGMKGERRRGKGHDGLYQGLSTATKDTYDALHMQALPPR

RS4 short CAR:

MPLLLLLPLLWAGALAMATAKFTYQGEEKQVDISKIKRVARYGQGIYFSY
DEGGGAYGYGSVSEKDAPKELLQMLEKQGGGGSGGGGSNWSHPQFEK**TTTPAPRPPTPAP
TIASQPLSLRPEACRPAAGGAVHTRGLDFACD**IYIWAPLAGTCGVLLLSLVITLYCKRGR
KKLLYIFKQPFMRPVQTTQEEDGCSCRFPEEEEGGCELRVKFSRSADAPAYKQGQNQLYN
ELNLGRREEYDVLDKRRGRDPEMGGKPRRKNPQEGLYNELQKDKMAEAYSEIGMKGERRR
GKGHDGLYQGLSTATKDTYDALHMQALPPR

RS5 short CAR:

MPLLLLLPLLWAGALAMATVKFTYQGEEKQVDISKIKRVARYGQGIYFDY
GEGGGAWGYGSVSEEDAPKELLQMLEKQGGGGSGGGGSNWSHPQFEK**TTTPAPRPPTPAP
TIASQPLSLRPEACRPAAGGAVHTRGLDFACD**IYIWAPLAGTCGVLLLSLVITLYCKRGR
KKLLYIFKQPFMRPVQTTQEEDGCSCRFPEEEEGGCELRVKFSRSADAPAYKQGQNQLYN
ELNLGRREEYDVLDKRRGRDPEMGGKPRRKNPQEGLYNELQKDKMAEAYSEIGMKGERRR
GKGHDGLYQGLSTATKDTYDALHMQALPPR

RS5 c-myc short CAR:

MPLLLLLPLLWAGALAMATVKFTYQGEEKQVDISKIKRVARYGQGIYFDY
GEGGGAWGYGSVSEEDAPKELLQMLEKQEQKLISEEDLGGGGSGGGGSNWSHPQFEK**TTT
PAPRPPTPAPTIASQPLSLRPEACRPAAGGAVHTRGLDFACD**IYIWAPLAGTCGVLLLSL
VITLYCKRGRKKLLYIFKQPFMRPVQTTQEEDGCSCRFPEEEEGGCELRVKFSRSADAPA
YKQGQNQLYNELNLGRREEYDVLDKRRGRDPEMGGKPRRKNPQEGLYNELQKDKMAEAYS
EIGMKGERRRGKGHDGLYQGLSTATKDTYDALHMQALPPR

RS3 c-myc long CAR:

MPLLLLLPLLWAGALAMATVKLTYQGEEKQVDISKIKRVARYGQNIYFSY
DEGGGAYDYGAVSEKDAPKELLQMLEKQEQKLISEEDLGGGGSGGGGSNWSHPQFEK*EPK
SPDKTHTCPPCPAPELLGGPSVFLFPPKPKDTLMISRTPEVTCVVVDVSHEDPEVKFNWY
VDGVEVHNAKTKPREEQYNSTYRVVSVLTVLHQDWLNGKEYKCKVSNKALPAPIEKTISK
AKGQPREPQVYTLPPSRDELTKNQVSLTCLVKGFYPSDIAVEWESNGQPENNYKTTPPVL
DSDGSFFLYSKLTVDKSRWQQGNVFSCSVMHEALHNHYTQKSLSLSPGKKDPK*
RVKFSRSADAPAYQQGQNQLYNELNLGRREEYDVLDKRRGRDPEMGGKPRRKNPQEGL
YNELQKDKMAEAYSEIGMKGERRRGKGHDGLYQGLSTATKDTYDALHMQALPPR

Fig. 7C

RS5 c-myc long CAR:
MPLLLLLPLLWAGALAMATVKFTYQGEEKQVDISKIKRVARYGQGIYFDY
GEGGGAWGYGSVSEEDAPKELLQMLEKQEQKLISEEDLGGGGSGGGGSNWSHPQFEKEPK
SPDKTHTCPPCPAPELLGGPSVFLFPPKPKDTLMISRTPEVTCVVVDVSHEDPEVKFNWY
VDGVEVHNAKTKPREEQYNSTYRVVSVLTVLHQDWLNGKEYKCKVSNKALPAPIEKTISK
AKGQPREPQVYTLPPSRDELTKNQVSLTCLVKGFYPSDIAVEWESNGQPENNYKTTPPVL
DSDGSFFLYSKLTVDKSRWQQGNVFSCSVMHEALHNHYTQKSLSLSPGKKDPKFWVLVVV
GGVLACYSLLVTVAFIIFWVRSKRSRLLHSDYMNMTPRRPGPTRKHYQPYAPPRDFAAYRSL
RVKFSRSADAPAYQQGQNQLYNELNLGRREEYDVLDKRRGRDPEMGGKPRRKNPQEGL
YNELQKDKMAEAYSEIGMKGERRRGKGHDGLYQGLSTATKDTYDALHMQALPPR

RS3 long CAR:
MPLLLLLPLLWAGALAMATVKLTYQGEEKQVDISKIKRVARYGQNIYFSYDEGGAYDYG
AVSEKDAPKELLQMLEKQGGGGSGGGGSNWSHPQFEKEPKSPDKTHTCPPCPAPELLGGP
SVFLFPPKPKDTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQVYTLPPSRDEL
TKNQVSLTCLVKGFYPSDIAVEWESNGQPENNYKTTPPVLDSDGSFFLYSKLTVDKSRWQ
QGNVFSCSVMHEALHNHYTQKSLSLSPGKKDPKFWVLVVVGGVLACYSLLVTVAFIIFWV
RSKRSRLLHSDYMNMTPRRPGPTRKHYQPYAPPRDFAAYRSLRVKFSRSADAPAYQQGQN
QLYNELNLGRREEYDVLDKRRGRDPEMGGKPRRKNPQEGLYNELQKDKMAEAYSEIGMKG
ERRRGKGHDGLYQGLSTATKDTYDALHMQALPPR

RS5 long CAR:
MPLLLLLPLLWAGALAMATVKFTYQGEEKQVDISKIKRVARYGQGIYFDYGEGGGAWGYG
SVSEEDAPKELLQMLEKQGGGGSGGGGSNWSHPQFEKEPKSPDKTHTCPPCPAPELLGGP
SVFLFPPKPKDTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQVYTLPPSRDEL
TKNQVSLTCLVKGFYPSDIAVEWESNGQPENNYKTTPPVLDSDGSFFLYSKLTVDKSRWQ
QGNVFSCSVMHEALHNHYTQKSLSLSPGKKDPKFWVLVVVGGVLACYSLLVTVAFIIFWV
RSKRSRLLHSDYMNMTPRRPGPTRKHYQPYAPPRDFAAYRSLRVKFSRSADAPAYQQGQN
QLYNELNLGRREEYDVLDKRRGRDPEMGGKPRRKNPQEGLYNELQKDKMAEAYSEIGMKG
ERRRGKGHDGLYQGLSTATKDTYDALHMQALPPR

Fig. 7D

RF2 long CAR:
MPLLLLLPLLWAGALAMVSDVPRDLEVVAATPTSLLISWYYPNASHAGYYRITYGETGGN
SPVQEFTVPFSIRYTIATISGLKPGVDYTITVYAVTDYAYYYRLSEPISINYRTGGGGSG
GGGSDPAEPKSPDKTHTCPPCPAPELLGGPSVFLFPPKPKDTLMISRTPEVTCVVVDVSH
EDPEVKFNWYVDGVEVHNAKTKPREEQYNSTYRVVSVLTVLHQDWLNGKEYKCKVSNKAL
PAPIEKTISKAKGQPREPQVYTLPPSRDELTKNQVSLTCLVKGFYPSDIAVEWESNGQPE
NNYKTTPPVLDSDGSFFLYSKLTVDKSRWQQGNVFSCSVMHEALHNHYTQKSLSLSPGKK
DPKFWVLVVVGGVLACYSLLVTVAFIIFWVRSKRSRLLHSDYMNMTPRRPGPTRKHYQPY
APPRDFAAYRSLRVKFSRSADAPAYQQGQNQLYNELNLGRREEYDVLDKRRGRDPEMGGK
PRRKNPQEGLYNELQKDKMAEAYSEIGMKGERRRGKGHDGLYQGLSTATKDTYDALHMQA
LPPR

RF2 SUMO CAR:
METDTLLLWVLLLWVPGSTGDGHHHHHHGSLQDSEVNQEAKPEVKPEVKPETHINLKVSDGS
SEIFFKIKKTTPLRRLMEAFAKRQGKEMDSLTFLYDGIEIQADQTPEDLDMEDNDIIEAHRE
QIGGGGGSGGGGSVSDVPRDLEVVAATPTSLLISWYYPNASHAGYYRITYGETGGNSPVQEF
TVPFSIRYTIATISGLKPGVDYTITVYAVTDYAYYYRLSEPISINYRTGGGGSGGGGSNWSH
PQFEKTTTPAPRPPTPAPTIASQPLSLRPEASRPAAGGAVHTRGLDFASDIYIWAPLAGTCG
VLLLSLVITLYCKRGRKKLLYIFKQPFMRPVQTTQEEDGCSCRFPEEEEGGCELSRGSGSGS
GSMGVQVETISPGDGRTFPKRGQTCVVHYTGMLEDGKKVDSSRDRNKPFKFMLGKQEVIRGW
EEGVAQMSVGQRAKLTISPDYAYGATGHPGIIPPHATLVFDVELLKLEGSGSGSGSSLRVKF
SRSADAPAYKQGQNQLYNELNLGRREEYDVLDKRRGRDPEMGGKPRRKNPQEGLYNELQKDK
MAEAYSEIGMKGERRRGKGHDGLYQGLSTATKDTYDALHMQALPPR

RBP4 Fc CAR: (bold letters indicate RBP4)
MPLLLLLPLLWAGALAMERDCRVSSFRVKENFDKARFSGTWYAMAKKDPE
GLFLQDNIVAEFSVDETGQMSATAKGRVRLLNNWDVCADMVGTFTDTEDPAKFKMKYWGV
ASFLQKGNDDHWIVDTDYDTYAVQYSCRLLNLDGTCADSYSFVFSRDPNGLPPEAQKIVR
QRQEELCLARQYRLIVHNGYCDGRSERNLLGGGGSGGGGSNWSHPQFEK*EPKSPDKTHTC*
*PPCPAPELLGGPSVFLFPPKPKDTLMISRTPEVTCVVVDVSHEDPEVKFNWYVDGVEVHN*
*AKTKPREEQYNSTYRVVSVLTVLHQDWLNGKEYKCKVSNKALPAPIEKTISKAKGQPREP*
*QVYTLPPSRDELTKNQVSLTCLVKGFYPSDIAVEWESNGQPENNYKTTPPVLDSDGSFFL*
*YSKLTVDKSRWQQGNVFSCSVMHEALHNHYTQKSLSLSPGKK*DPKFWVLVVVGGVLACYS
LLVTVAFIIFWVRSKRSRLLHSDYMNMTPRRPGPTRKHYQPYAPPRDFAAYRSLRVKFSR
SADAPAYQQGQNQLYNELNLGRREEYDVLDKRRGRDPEMGGKPRRKNPQEGLYNELQKDK
MAEAYSEIGMKGERRRGKGHDGLYQGLSTATKDTYDALHMQALPPR

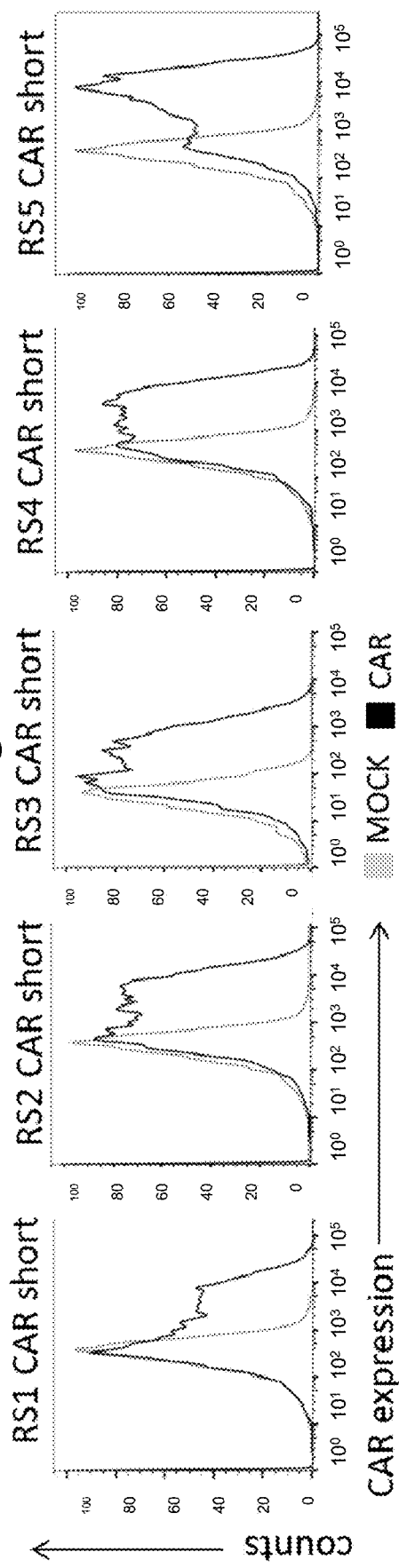
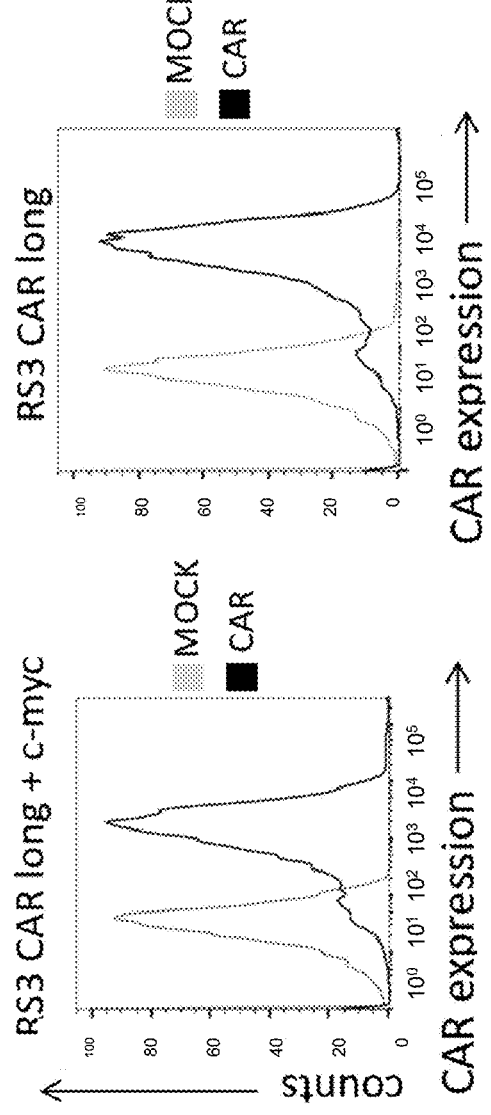
Fig. 8A

Fig. 9
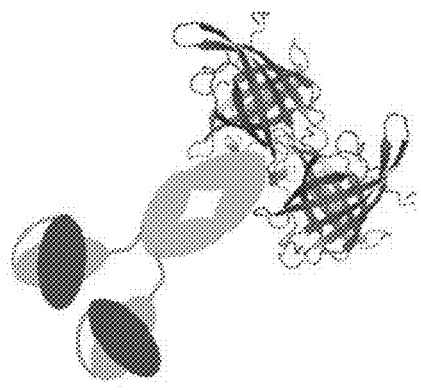
A
RBP4-CD19 scFv fusion
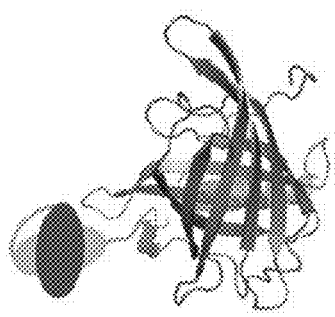
B
RBP4-IgG Fc -

Fig. 10

Underlined text = RBP4 signal peptide (SP)

Underlined (bold) text = CD19 scFv
Dark grey text = G4S linker (GGGGS) linker
Underlined (dotted) text = His-Tag
*Italic text* = Fc domain (IgG)
Underlined (double) text = RBP4
Underlined text = RS3 (rcSso7d-based RBP4-binder)
*Underlined italic text* = rcSso7d-based EGFR-binder

Fusion protein "A"

MKWVWALLLLAALGSGRADIQMTQTTSSLSASLGDRVTISCRASQDISKY
LNWYQQKPDGTVKLLIYHTSRLHSGVPSRFSGSGSGTDYSLTISNLEQEDIATYFCQQGN
TLPYTFGGGTKLEITGSTSGSGKPGSGEGSTKGEVKLQESGPGLVAPSQSLVTCTVSGV
SLPDYGVSWIRQPPRKGLEWLGVIWGSETTYYNSALKSRLTIIKDNSKSQVFLKMNSLQT
DDTAIYYCAKHYYYGGSYAMDYWGQGTSVTVSSGGGGSHHHHHHERDCRVSSFRVKENFD
KARFSGTWYAMAKKDPEGLFLQDNIVAEFSVDETGQMSATAKGRVRLLNNWDVCADMVGT
FTDTEDPAKFKMKYWGVASFLQKGNDDHWIVDTDYDTYAVQYSCRLLNLDGTCADSYSFV
FSRDPNGLPPEAQKIVRQRQEELCLARQYRLIVHNGYCDGRSERNLL

Fusion protein "B"

MKWVWALLLLAALGSGRADIQMTQTTSSLSASLGDRVTISCRASQDISKY
LNWYQQKPDGTVKLLIYHTSRLHSGVPSRFSGSGSGTDYSLTISNLEQEDIATYFCQQGN
TLPYTFGGGTKLEITGSTSGSGKPGSGEGSTKGEVKLQESGPGLVAPSQSLVTCTVSGV
SLPDYGVSWIRQPPRKGLEWLGVIWGSETTYYNSALKSRLTIIKDNSKSQVFLKMNSLQT
DDTAIYYCAKHYYYGGSYAMDYWGQGTSVTVSSGGGGS*EPKSPDKTHTCPPCPAPELLGG
PSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSRDE
LTKNQVSLTCLVKGFYPSDIAVEWESNGQPENNYKTTPPVLDSDGSFFLYSKLTVDKSRW
QQGNVFSCSVMHEALHNHYTQKSLSLSPGK*GGGGSHHHHHHERDCRVSSFRVKENFDKAR
FSGTWYAMAKKDPEGLFLQDNIVAEFSVDETGQMSATAKGRVRLLNNWDVCADMVGTFTD
TEDPAKFKMKYWGVASFLQKGNDDHWIVDTDYDTYAVQYSCRLLNLDGTCADSYSFVFSR
DPNGLPPEAQKIVRQRQEELCLARQYRLIVHNGYCDGRSERNLL

Fig. 10 contin.

Underlined text = RBP4 signal peptide (SP)

Underlined (bold) text = CD19 scFv
Dark grey text = G4S linker (GGGGS) linker
Underlined (dotted) text = His-Tag
*Italic text* = Fc domain (IgG)
Underlined (double) text = RBP4
Underlined text = RS3 (rcSso7d-based RBP4-binder)
*Underlined italic text* = rcSso7d-based EGFR-binder

Fusion protein "C"

MKWVWALLLLAALGSGRADIQMTQTTSSLSASLGDRVTISCRASQDISKY
LNWYQQKPDGTVKLLIYHTSRLHSGVPSRFSGSGSGTDYSLTISNLEQEDIATYFCQQGN
TLPYTFGGGTKLEITGSTSGSGKPGSGEGSTKGEVKLQESGPGLVAPSQSLSVTCTVSGV
SLPDYGVSWIRQPPRKGLEWLGVIWGSETTYYNSALKSRLTIIKDNSKSQVFLKMNSLQT
DDTAIYYCAKHYYYGGSYAMDYWGQGTSVTVSSGGGGSHHHHHHATVKLTYQGEEKQVDI
SKIKRVARYGQNIYFSYDEGGGAYDYGAVSEKDAPKELLQMLEKQEQKLISEEDL

Fusion protein "D"

MKWVWALLLLAALGSGRA*ATVKFTYQGEEKQVDISKIMYVIRGGQRIAFG*
*YDEGDGAWGDGIVSEKDAPKELLQMLEKQ*GGGGSHHHHHH*ERDCRVSSFRVKENFDKARF*
*SGTWYAMAKKDPEGLFLQDNIVAEFSVDETGQMSATAKGRVRLLNNWDVCADMVGTFTDT*
*EDPAKFKMKYWGVASFLQKGNDDHWIVDTDYDTYAVQYSCRLLNLDGTCADSYSFVFSRD*
*PNGLPPEAQKIVRQRQEELCLARQYRLIVHNGYCDGRSERNLL*

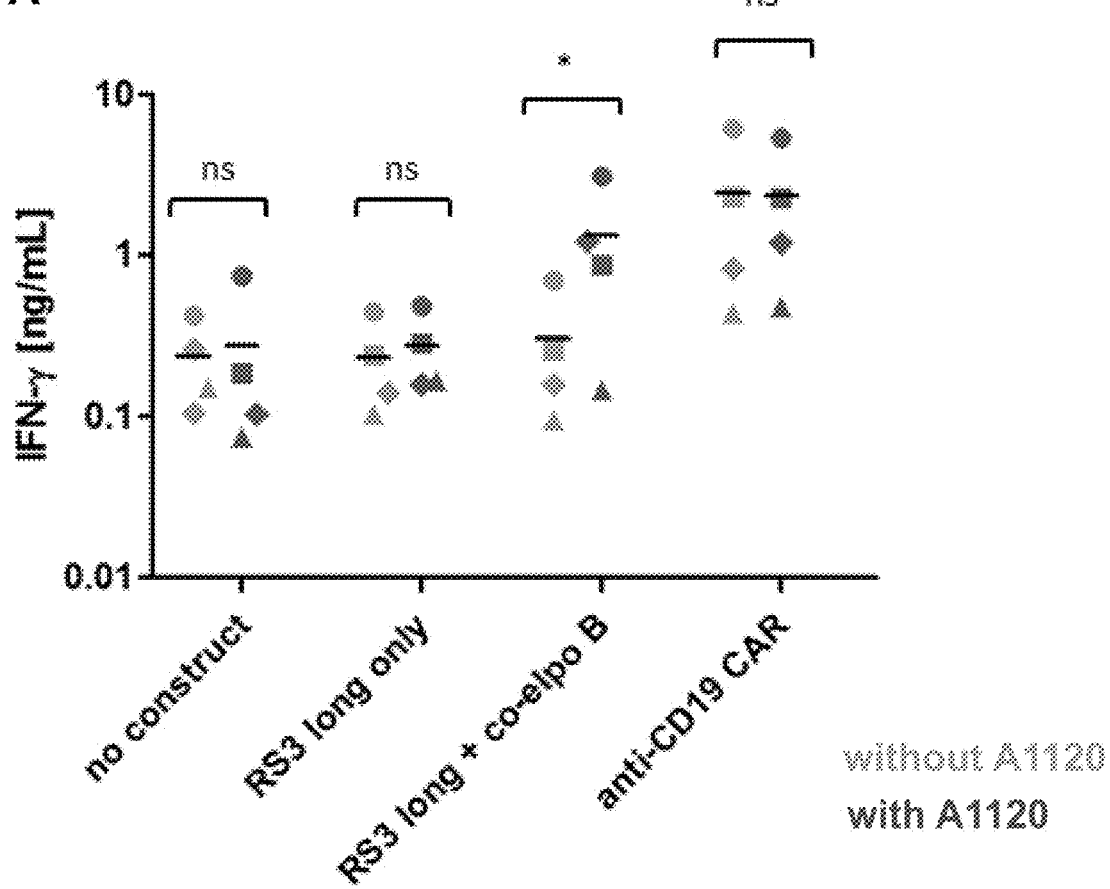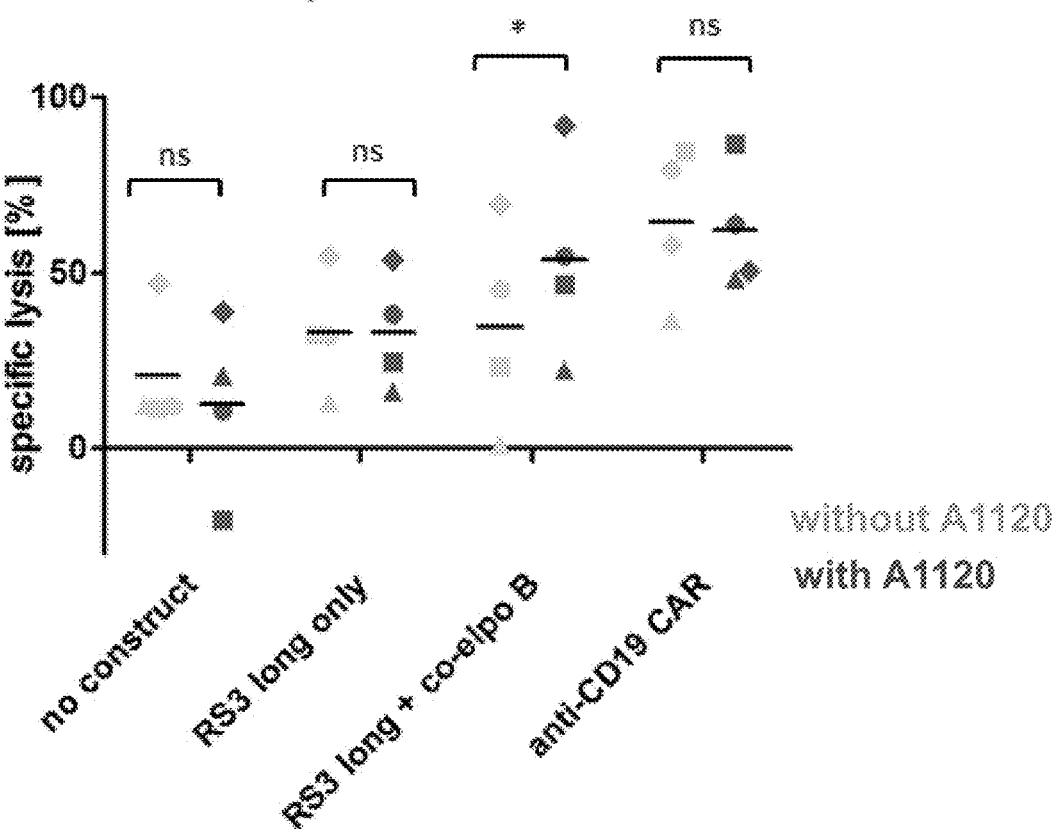
Fig. 13

Fig. 18

| rcSso7d- or FN3-based hRBP4 binding interaction partner | Yeast display $K_D$ (nM; mean ± S.D.) | | ITC $K_D$ (nM; mean ± S.D.) | | $\frac{K_{D,-A1120}}{K_{D,+A1120}}$ | SPR $K_D$ (nM; mean ± S.D.) | | $\frac{K_{D,-A1120}}{K_{D,+A1120}}$ |
|---|---|---|---|---|---|---|---|---|
| | +A1120 | -A1120 | +A1120 | -A1120 | | +A1120 | -A1120 | |
| RS3 | 13 ± 7 | n.a.* | 7 ± 3 | 2690 ± 1290 | 384 | 9 ± 1 | 4950 ± 870 | 550 |
| RS5 | 80 ± 50 | n.a.* | 17 ± 7 | 3778 ± 1156 | 222 | 38 ± 23 | 11004 ± 4330 | 290 |
| RF2 | 65 ± 42 | n.a.* | 279 ± 85 | 4376 ± 2109 | 16 | n.a.* | n.a.* | n.a.* |

SEQUENCE LISTING

```
Sequence total quantity: 42
SEQ ID NO: 1            moltype = DNA   length = 42
FEATURE                 Location/Qualifiers
misc_feature            1..42
                        note = epSSo primer
source                  1..42
                        mol_type = other DNA
                        organism = synthetic construct
SEQUENCE: 1
ggctctggtg gaggcggtag cggaggcgga gggtcggcta gc                      42
```

```
SEQ ID NO: 2              moltype = DNA  length = 42
FEATURE                   Location/Qualifiers
misc_feature              1..42
                          note = epSso primer
source                    1..42
                          mol_type = other DNA
                          organism = synthetic construct
SEQUENCE: 2
ctattacaag tcctcttcag aaataagctt tgttcggat cc                              42

SEQ ID NO: 3              moltype = DNA  length = 25
FEATURE                   Location/Qualifiers
misc_feature              1..25
                          note = picZalpha primer
source                    1..25
                          mol_type = other DNA
                          organism = synthetic construct
SEQUENCE: 3
attgccagca ttgctgctaa agaag                                               25

SEQ ID NO: 4              moltype = DNA  length = 21
FEATURE                   Location/Qualifiers
misc_feature              1..21
                          note = picZalpha primer
source                    1..21
                          mol_type = other DNA
                          organism = synthetic construct
SEQUENCE: 4
gcaaatggca ttctgacatc c                                                   21

SEQ ID NO: 5              moltype = AA  length = 457
FEATURE                   Location/Qualifiers
REGION                    1..457
                          note = fusion protein
source                    1..457
                          mol_type = protein
                          organism = synthetic construct
SEQUENCE: 5
MKWVWALLLL AALGSGRADI QMTQTTSSLS ASLGDRVTIS CRASQDISKY LNWYQQKPDG    60
TVKLLIYHTS RLHSGVPSRF SGSGSGTDYS LTISNLEQED IATYFCQQGN TLPYTFGGGT   120
KLEITGSTSG SGKPGSGEGS TKGEVKLQES GPGLVAPSQS LSVTCTVSGV SLPDYGVSWI   180
RQPPRKGLEW LGVIWGSETT YYNSALKSRL TIIKDNSKSQ VFLKMNSLQT DDTAIYYCAK   240
HYYYGGSYAM DYWGQGTSVT VSSGGGGSHH HHHHERDCRV SSFRVKENFD KARFSGTWYA   300
MAKKDPEGLF LQDNIVAEFS VDETGQMSAT AKGRVRLLNN WDVCADMVGT FTDTEDPAKF   360
KMKYWGVASF LQKGNDDHWI VDTDYDTYAV QYSCRLLNLD GTCADSYSFV FSRDPNGLPP   420
EAQKIVRQRQ EELCLARQYR LIVHNGYCDG RSERNLL                            457

SEQ ID NO: 6              moltype = AA  length = 694
FEATURE                   Location/Qualifiers
REGION                    1..694
                          note = fusion protein
source                    1..694
                          mol_type = protein
                          organism = synthetic construct
SEQUENCE: 6
MKWVWALLLL AALGSGRADI QMTQTTSSLS ASLGDRVTIS CRASQDISKY LNWYQQKPDG    60
TVKLLIYHTS RLHSGVPSRF SGSGSGTDYS LTISNLEQED IATYFCQQGN TLPYTFGGGT   120
KLEITGSTSG SGKPGSGEGS TKGEVKLQES GPGLVAPSQS LSVTCTVSGV SLPDYGVSWI   180
RQPPRKGLEW LGVIWGSETT YYNSALKSRL TIIKDNSKSQ VFLKMNSLQT DDTAIYYCAK   240
HYYYGGSYAM DYWGQGTSVT VSSGGGGSEP KSPDKTHTCP PCPAPELLGG PSVFLFPPKP   300
KDTLMISRTP EVTCVVVDVS HEDPEVKFNW YVDGVEVHNA KTKPREEQYN STYRVVSVLT   360
VLHQDWLNGK EYKCKVSNKA LPAPIEKTIS KAKGQPREPQ VYTLPPSRDE LTKNQVSLTC   420
LVKGFYPSDI AVEWESNGQP ENNYKTTPPV LDSDGSFFLY SKLTVDKSRW QQGNVFSCSV   480
MHEALHNHYT QKSLSLSPGK GGGGSHHHHH HERDCRVSSF RVKENFDKAR FSGTWYAMAK   540
KDPEGLFLQD NIVAEFSVDE TGQMSATAKG RVRLLNNWDV CADMVGTFTD TEDPAKFKMK   600
YWGVASFLQK GNDDHWIVDT DYDTYAVQYS CRLLNLDGTC ADSYSFVFSR DPNGLPPEAQ   660
KIVRQRQEEL CLARQYRLIV HNGYCDGRSE RNLL                              694

SEQ ID NO: 7              moltype = AA  length = 345
FEATURE                   Location/Qualifiers
REGION                    1..345
                          note = fusion protein
source                    1..345
                          mol_type = protein
                          organism = synthetic construct
SEQUENCE: 7
MKWVWALLLL AALGSGRADI QMTQTTSSLS ASLGDRVTIS CRASQDISKY LNWYQQKPDG    60
TVKLLIYHTS RLHSGVPSRF SGSGSGTDYS LTISNLEQED IATYFCQQGN TLPYTFGGGT   120
```

```
KLEITGSTSG SGKPGSGEGS TKGEVKLQES GPGLVAPSQS LSVTCTVSGV SLPDYGVSWI    180
RQPPRKGLEW LGVIWGSETT YYNSALKSRL TIIKDNSKSQ VFLKMNSLQT DDTAIYYCAK    240
HYYYGGSYAM DYWGQGTSVT VSSGGGGSHH HHHHATVKLT YQGEEKQVDI SKIKRVARYG    300
QNIYFSYDEG GAYDYGAVS EKDAPKELLQ MLEKQEQKLI SEEDL                    345

SEQ ID NO: 8              moltype = AA   length = 273
FEATURE                   Location/Qualifiers
REGION                    1..273
                          note = fusion protein
source                    1..273
                          mol_type = protein
                          organism = synthetic construct
SEQUENCE: 8
MKWVWALLLL AALGSGRAAT VKFTYQGEEK QVDISKIMYV IRGGQRIAFG YDEGDGAWGD     60
GIVSEKDAPK ELLQMLEKQG GGGSHHHHHH ERDCRVSSFR VKENFDKARF SGTWYAMAKK    120
DPEGLFLQDN IVAEFSVDET GQMSATAKGR VRLLNNWDVC ADMVGTFTDT EDPAKFKMKY    180
WGVASFLQKG NDDHWIVDTD YDTYAVQYSC RLLNLDGTCA DSYSFVFSRD PNGLPPEAQK    240
IVRQRQEELC LARQYRLIVH NGYCDGRSER NLL                                273

SEQ ID NO: 9              moltype = AA   length = 61
FEATURE                   Location/Qualifiers
REGION                    1..61
                          note = fusion protein
source                    1..61
                          mol_type = protein
                          organism = synthetic construct
SEQUENCE: 9
ATVKFTYQGE EKQVDISKIK WVIRWGQHIA FKYDEGGGAA GYGWVSEKDA PKELLQMLEK     60
Q                                                                    61

SEQ ID NO: 10             moltype = DNA   length = 183
FEATURE                   Location/Qualifiers
misc_feature              1..183
                          note = fusion protein
source                    1..183
                          mol_type = other DNA
                          organism = synthetic construct
SEQUENCE: 10
gcaaccgtga aattcacata ccaaggcgaa gaagaacagg tggatattag caaaatcaag     60
aaagtggctc gttacggcca gaacatttac ttttcttatg atgaaggtgg tggtgcctgg    120
gattatggtg gcgtgagcga aaaagatgca ccgaaagaac tgctgcagat gctggaaaag    180
caa                                                                  183

SEQ ID NO: 11             moltype = AA   length = 61
FEATURE                   Location/Qualifiers
REGION                    1..61
                          note = fusion protein
source                    1..61
                          mol_type = protein
                          organism = synthetic construct
SEQUENCE: 11
ATVKFTYQGE EEQVDISKIK KVARYGQNIY FSYDEGGGAW DYGGVSEKDA PKELLQMLEK     60
Q                                                                    61

SEQ ID NO: 12             moltype = DNA   length = 183
FEATURE                   Location/Qualifiers
misc_feature              1..183
                          note = fusion protein
source                    1..183
                          mol_type = other DNA
                          organism = synthetic construct
SEQUENCE: 12
gcaaccgtga aactcacata ccaaggcgaa gaaaaacagg tggatattag caaaatcaag     60
cgtgtggctc gttacggcca gggtatttac tttgactatg gtgaaggtgg tggtgcctgg    120
ggttacggta gcgtgagcga aaaagatgca ccgaaagaac tgctgcagat gctggaaaag    180
caa                                                                  183

SEQ ID NO: 13             moltype = AA   length = 61
FEATURE                   Location/Qualifiers
REGION                    1..61
                          note = fusion protein
source                    1..61
                          mol_type = protein
                          organism = synthetic construct
SEQUENCE: 13
ATVKLTYQGE EKQVDISKIK RVARYGQGIY FDYGEGGGAW GYGSVSEKDA PKELLQMLEK     60
Q                                                                    61
```

```
SEQ ID NO: 14          moltype = DNA  length = 183
FEATURE                Location/Qualifiers
misc_feature           1..183
                       note = fusion protein
source                 1..183
                       mol_type = other DNA
                       organism = synthetic construct
SEQUENCE: 14
gcaaccgtga aactcacata ccaaggcgaa gaaaaacagg tggatattag caaaatcaag    60
cgtgtggctc gttacggcca gaacatttac tttccttatg atgaaggtgg tggtgcctat   120
gattatggtg cagtgagcga aaaagatgca ccgaaagaac tgctgcagat gctggaaaag   180
caa                                                                 183

SEQ ID NO: 15          moltype = AA  length = 61
FEATURE                Location/Qualifiers
REGION                 1..61
                       note = fusion protein
source                 1..61
                       mol_type = protein
                       organism = synthetic construct
SEQUENCE: 15
ATVKLTYQGE EKQVDISKIK RVARYGQNIY FSYDEGGGAY DYGAVSEKDA PKELLQMLEK    60
Q                                                                   61

SEQ ID NO: 16          moltype = DNA  length = 183
FEATURE                Location/Qualifiers
misc_feature           1..183
                       note = fusion protein
source                 1..183
                       mol_type = other DNA
                       organism = synthetic construct
SEQUENCE: 16
gcaaccgcga aattcacata ccaaggcgaa gaaaaacagg tggatattag caaaatcaag    60
cgcgtggctc gttacggcca gggtatttac tttccttatg atgaaggtgg tggtgcctat   120
ggttatggta gcgtgagcga aaaagatgca ccgaaagaac tgctgcagat gctggaaaag   180
caa                                                                 183

SEQ ID NO: 17          moltype = AA  length = 61
FEATURE                Location/Qualifiers
REGION                 1..61
                       note = fusion protein
source                 1..61
                       mol_type = protein
                       organism = synthetic construct
SEQUENCE: 17
ATAKFTYQGE EKQVDISKIK RVARYGQGIY FSYDEGGGAY GYGSVSEKDA PKELLQMLEK    60
Q                                                                   61

SEQ ID NO: 18          moltype = DNA  length = 183
FEATURE                Location/Qualifiers
misc_feature           1..183
                       note = fusion protein
source                 1..183
                       mol_type = other DNA
                       organism = synthetic construct
SEQUENCE: 18
gcaaccgtga aattcacata ccaaggcgaa gaaaaacagg tggatattag caaaatcaag    60
cgtgtggctc gttacggcca gggtatttac tttgactatg gtgaaggtgg tggtgcctgg   120
ggttacggta gcgtgagcga agaagatgca ccgaaagaac tgctgcagat gctggaaaag   180
caa                                                                 183

SEQ ID NO: 19          moltype = AA  length = 61
FEATURE                Location/Qualifiers
REGION                 1..61
                       note = fusion protein
source                 1..61
                       mol_type = protein
                       organism = synthetic construct
SEQUENCE: 19
ATVKFTYQGE EKQVDISKIK RVARYGQGIY FDYGEGGGAW GYGSVSEEDA PKELLQMLEK    60
Q                                                                   61

SEQ ID NO: 20          moltype = AA  length = 101
FEATURE                Location/Qualifiers
REGION                 1..101
                       note = fusion protein
```

```
                        source                  1..101
                                                mol_type = protein
                                                organism = synthetic construct
SEQUENCE: 20
VSDVPRDLEV VAATPTSLLI SWDAPAVTVR YYRITYGETG GNSPVQEFTV PGSKSTATIS          60
GLKPGVDYTI TVYAVTGRGD SPASSKPISI NYRTEIDKPS Q                             101

SEQ ID NO: 21           moltype = DNA   length = 313
FEATURE                 Location/Qualifiers
misc_feature            1..313
                        note = fusion protein
source                  1..313
                        mol_type = other DNA
                        organism = synthetic construct
SEQUENCE: 21
gtttctgatg ttccgaggga cctggaagtt gttgctgcga ccccaccag cctactgatc           60
agctggtatt atcccaacgc tagtcatgcg ggttattaca gggtcactta cggagaaaca         120
ggaggaaata gccctgtcca ggagttcact gtgccttct ctattcggta tactattgct          180
accatcagcg gccttaaacc tggagttgat cataccatca ctgtgtatgc tgtcactgac         240
tacgccatt actaccgctc gtctgagcca atttccatta attaccgaac agaaattgac          300
aaaccatccc agg                                                            313

SEQ ID NO: 22           moltype = AA    length = 104
FEATURE                 Location/Qualifiers
REGION                  1..104
                        note = fusion protein
source                  1..104
                        mol_type = protein
                        organism = synthetic construct
SEQUENCE: 22
VSDVPRDLEV VAATPTSLLI SWYYPNASHA GYYRVTYGET GGNSPVQEFT VPFSIRYTIA          60
TISGLKPGVD HTITVYAVTD YAYYYRSSEP ISINYRTEID KPSQ                          104

SEQ ID NO: 23           moltype = DNA   length = 313
FEATURE                 Location/Qualifiers
misc_feature            1..313
                        note = fusion protein
source                  1..313
                        mol_type = other DNA
                        organism = synthetic construct
SEQUENCE: 23
gtttctgatg ttccgaggga cctggaagtt gttgctgcga ccccaccag cctactgatc           60
agctggtatt atcccaacgc tagtcatgcg ggttattaca gggtcactta cggagaaaca         120
ggaggaaata gccctgtcca ggagttcact gtgcctttct ctattcggta tactattgct         180
accatcagcg gccttaaacc tggagttgat tataccatca ctgtgtatgc tgtcactgac         240
tacgccatt actaccgctt gtctgagcca atttccatta attaccgaac agaaattgac          300
aaaccatccc agg                                                            313

SEQ ID NO: 24           moltype = AA    length = 104
FEATURE                 Location/Qualifiers
REGION                  1..104
                        note = fusion protein
source                  1..104
                        mol_type = protein
                        organism = synthetic construct
SEQUENCE: 24
VSDVPRDLEV VAATPTSLLI SWYYPNASHA GYYRITYGET GGNSPVQEFT VPFSIRYTIA          60
TISGLKPGVD YTITVYAVTD YAYYYRLSEP ISINYRTEID KPSQ                          104

SEQ ID NO: 25           moltype = DNA   length = 307
FEATURE                 Location/Qualifiers
misc_feature            1..307
                        note = fusion protein
source                  1..307
                        mol_type = other DNA
                        organism = synthetic construct
SEQUENCE: 25
gtttctgatg ttccgaggga cctggaagtt gttgctgcga ccccaccag cctactgatc           60
agctggtatt atcccaacgc tagtcatgcg ggttattaca ggatcactta cggagaaaca         120
ggaggaaata gccctgtcca ggagttcact gtgcctttct ctattcggta tactattgct         180
accatcagcg gccttaaacc tggagttgat tataccatca ctgtgtatgc tgtcactgcc         240
agttgtcagt attgctctta tccaatttcc attaattacc gaacagaaat tgacaaacca         300
tcccagg                                                                   307

SEQ ID NO: 26           moltype = AA    length = 102
FEATURE                 Location/Qualifiers
REGION                  1..102
                        note = fusion protein
```

```
source                        1..102
                              mol_type = protein
                              organism = synthetic construct
SEQUENCE: 26
VSDVPRDLEV VAATPTSLLI SWYYPNASHA GYYRITYGET GGNSPVQEFT VPFSIRYTIA    60
TISGLKPGVD YTITVYAVTA SCQYCSYPIS INYRTEIDKP SQ                     102

SEQ ID NO: 27                 moltype = AA  length = 320
FEATURE                       Location/Qualifiers
REGION                        1..320
                              note = fusion protein
source                        1..320
                              mol_type = protein
                              organism = synthetic construct
SEQUENCE: 27
MPLLLLLPLL WAGALAMATV KFTYQGEEEQ VDISKIKKVA RYGQNIYFSY DEGGGAWDYG    60
GVSEKDAPKE LLQMLEKQGG GGSGGGGSNW SHPQFEKTTT PAPRPPTPAP TIASQPLSLR   120
PEACRPAAGG AVHTRGLDFA CDIYIWAPLA GTCGVLLLSL VITLYCKRGR KKLLYIFKQP   180
FMRPVQTTQE EDGCSCRFPE EEEGGCELRV KFSRSADAPA YKQGQNQLYN ELNLGRREEY   240
DVLDKRRGRD PEMGGKPRRK NPQEGLYNEL QKDKMAEAYS EIGMKGERRR GKGHDGLYQG   300
LSTATKDTYD ALHMQALPPR                                              320

SEQ ID NO: 28                 moltype = AA  length = 320
FEATURE                       Location/Qualifiers
REGION                        1..320
                              note = fusion protein
source                        1..320
                              mol_type = protein
                              organism = synthetic construct
SEQUENCE: 28
MPLLLLLPLL WAGALAMATV KLTYQGEEKQ VDISKIKRVA RYGQGIYFDY GEGGGAWGYG    60
SVSEKDAPKE LLQMLEKQGG GGSGGGGSNW SHPQFEKTTT PAPRPPTPAP TIASQPLSLR   120
PEACRPAAGG AVHTRGLDFA CDIYIWAPLA GTCGVLLLSL VITLYCKRGR KKLLYIFKQP   180
FMRPVQTTQE EDGCSCRFPE EEEGGCELRV KFSRSADAPA YKQGQNQLYN ELNLGRREEY   240
DVLDKRRGRD PEMGGKPRRK NPQEGLYNEL QKDKMAEAYS EIGMKGERRR GKGHDGLYQG   300
LSTATKDTYD ALHMQALPPR                                              320

SEQ ID NO: 29                 moltype = AA  length = 320
FEATURE                       Location/Qualifiers
REGION                        1..320
                              note = fusion protein
source                        1..320
                              mol_type = protein
                              organism = synthetic construct
SEQUENCE: 29
MPLLLLLPLL WAGALAMATV KLTYQGEEKQ VDISKIKRVA RYGQNIYFSY DEGGGAYDYG    60
AVSEKDAPKE LLQMLEKQGG GGSGGGGSNW SHPQFEKTTT PAPRPPTPAP TIASQPLSLR   120
PEACRPAAGG AVHTRGLDFA CDIYIWAPLA GTCGVLLLSL VITLYCKRGR KKLLYIFKQP   180
FMRPVQTTQE EDGCSCRFPE EEEGGCELRV KFSRSADAPA YKQGQNQLYN ELNLGRREEY   240
DVLDKRRGRD PEMGGKPRRK NPQEGLYNEL QKDKMAEAYS EIGMKGERRR GKGHDGLYQG   300
LSTATKDTYD ALHMQALPPR                                              320

SEQ ID NO: 30                 moltype = AA  length = 330
FEATURE                       Location/Qualifiers
REGION                        1..330
                              note = fusio protein
source                        1..330
                              mol_type = protein
                              organism = synthetic construct
SEQUENCE: 30
MPLLLLLPLL WAGALAMATV KLTYQGEEKQ VDISKIKRVA RYGQNIYFSY DEGGGAYDYG    60
AVSEKDAPKE LLQMLEKQEQ KLISEEDLGG GGSGGGGSNW SHPQFEKTTT PAPRPPTPAP   120
TIASQPLSLR PEACRPAAGG AVHTRGLDFA CDIYIWAPLA GTCGVLLLSL VITLYCKRGR   180
KKLLYIFKQP FMRPVQTTQE EDGCSCRFPE EEEGGCELRV KFSRSADAPA YKQGQNQLYN   240
ELNLGRREEY DVLDKRRGRD PEMGGKPRRK NPQEGLYNEL QKDKMAEAYS EIGMKGERRR   300
GKGHDGLYQG LSTATKDTYD ALHMQALPPR                                   330

SEQ ID NO: 31                 moltype = AA  length = 320
FEATURE                       Location/Qualifiers
REGION                        1..320
                              note = fusion protein
source                        1..320
                              mol_type = protein
                              organism = synthetic construct
SEQUENCE: 31
MPLLLLLPLL WAGALAMATA KFTYQGEEKQ VDISKIKRVA RYGQGIYFSY DEGGGAYGYG    60
SVSEKDAPKE LLQMLEKQGG GGSGGGGSNW SHPQFEKTTT PAPRPPTPAP TIASQPLSLR   120
PEACRPAAGG AVHTRGLDFA CDIYIWAPLA GTCGVLLLSL VITLYCKRGR KKLLYIFKQP   180
FMRPVQTTQE EDGCSCRFPE EEEGGCELRV KFSRSADAPA YKQGQNQLYN ELNLGRREEY   240
```

```
DVLDKRRGRD PEMGGKPRRK NPQEGLYNEL QKDKMAEAYS EIGMKGERRR GKGHDGLYQG    300
LSTATKDTYD ALHMQALPPR                                                320

SEQ ID NO: 32           moltype = AA  length = 320
FEATURE                 Location/Qualifiers
REGION                  1..320
                        note = fusion protein
source                  1..320
                        mol_type = protein
                        organism = synthetic construct
SEQUENCE: 32
MPLLLLLPLL WAGALAMATV KFTYQGEEKQ VDISKIKRVA RYGQGIYFDY GEGGGAWGYG     60
SVSEEDAPKE LLQMLEKQGG GGSGGGGSNW SHPQFEKTTT PAPRPPTPAP TIASQPLSLR    120
PEACRPAAGG AVHTRGLDFA CDIYIWAPLA GTCGVLLLSL VITLYCKRGR KKLLYIFKQP    180
FMRPVQTTQE EDGCSCRFPE EEEGGCELRV KFSRSADAPA YKQGQNQLYN ELNLGRREEY    240
DVLDKRRGRD PEMGGKPRRK NPQEGLYNEL QKDKMAEAYS EIGMKGERRR GKGHDGLYQG    300
LSTATKDTYD ALHMQALPPR                                                320

SEQ ID NO: 33           moltype = AA  length = 330
FEATURE                 Location/Qualifiers
REGION                  1..330
                        note = fusion protein
source                  1..330
                        mol_type = protein
                        organism = synthetic construct
SEQUENCE: 33
MPLLLLLPLL WAGALAMATV KFTYQGEEKQ VDISKIKRVA RYGQGIYFDY GEGGGAWGYG     60
SVSEEDAPKE LLQMLEKQEQ KLISEEDLGG GGSGGGGSNW SHPQFEKTTT PAPRPPTPAP    120
TIASQPLSLR PEACRPAAGG AVHTRGLDFA CDIYIWAPLA GTCGVLLLSL VITLYCKRGR    180
KKLLYIFKQP FMRPVQTTQE EDGCSCRFPE EEEGGCELRV KFSRSADAPA YKQGQNQLYN    240
ELNLGRREEY DVLDKRRGRD PEMGGKPRRK NPQEGLYNEL QKDKMAEAYS EIGMKGERRR    300
GKGHDGLYQG LSTATKDTYD ALHMQALPPR                                     330

SEQ ID NO: 34           moltype = AA  length = 524
FEATURE                 Location/Qualifiers
REGION                  1..524
                        note = fusion protein
source                  1..524
                        mol_type = protein
                        organism = synthetic construct
SEQUENCE: 34
MPLLLLLPLL WAGALAMATV KLTYQGEEKQ VDISKIKRVA RYGQNIYFSY DEGGGAYDYG     60
AVSEKDAPKE LLQMLEKQEQ KLISEEDLGG GGSGGGGSNW SHPQFEKEPK SPDKTHTCPP    120
CPAPELLGGP SVFLFPPKPK DTLMISRTPE VTCVVVDVSH EDPEVKFNWY VDGVEVHNAK    180
TKPREEQYNS TYRVVSVLTV LHQDWLNGKE YKCKVSNKAL PAPIEKTISK AKGQPREPQV    240
YTLPPSRDEL TKNQVSLTCL VKGFYPSDIA VEWESNGQPE NNYKTTPPVL DSDGSFFLYS    300
KLTVDKSRWQ QGNVFSCSVM HEALHNHYTQ KSLSLSPGKK DPKFWVLVVV GGVLACYSLL    360
VTVAFIIFWV RSKRSRLLHS DYMNMTPRRP GPTRKHYQPY APPRDFAAYR SLRVKFSRSA    420
DAPAYQQGQN QLYNELNLGR REEYDVLDKR RGRDPEMGGK PRRKNPQEGL YNELQKDKMA    480
EAYSEIGMKG ERRRGKGHDG LYQGLSTATK DTYDALHMQA LPPR                     524

SEQ ID NO: 35           moltype = AA  length = 524
FEATURE                 Location/Qualifiers
REGION                  1..524
                        note = fusion protein
source                  1..524
                        mol_type = protein
                        organism = synthetic construct
SEQUENCE: 35
MPLLLLLPLL WAGALAMATV KFTYQGEEKQ VDISKIKRVA RYGQGIYFDY GEGGGAWGYG     60
SVSEEDAPKE LLQMLEKQEQ KLISEEDLGG GGSGGGGSNW SHPQFEKEPK SPDKTHTCPP    120
CPAPELLGGP SVFLFPPKPK DTLMISRTPE VTCVVVDVSH EDPEVKFNWY VDGVEVHNAK    180
TKPREEQYNS TYRVVSVLTV LHQDWLNGKE YKCKVSNKAL PAPIEKTISK AKGQPREPQV    240
YTLPPSRDEL TKNQVSLTCL VKGFYPSDIA VEWESNGQPE NNYKTTPPVL DSDGSFFLYS    300
KLTVDKSRWQ QGNVFSCSVM HEALHNHYTQ KSLSLSPGKK DPKFWVLVVV GGVLACYSLL    360
VTVAFIIFWV RSKRSRLLHS DYMNMTPRRP GPTRKHYQPY APPRDFAAYR SLRVKFSRSA    420
DAPAYQQGQN QLYNELNLGR REEYDVLDKR RGRDPEMGGK PRRKNPQEGL YNELQKDKMA    480
EAYSEIGMKG ERRRGKGHDG LYQGLSTATK DTYDALHMQA LPPR                     524

SEQ ID NO: 36           moltype = AA  length = 514
FEATURE                 Location/Qualifiers
REGION                  1..514
                        note = fusion protein
source                  1..514
                        mol_type = protein
                        organism = synthetic construct
SEQUENCE: 36
MPLLLLLPLL WAGALAMATV KLTYQGEEKQ VDISKIKRVA RYGQNIYFSY DEGGGAYDYG     60
AVSEKDAPKE LLQMLEKQGG GGSGGGGSNW SHPQFEKEPK SPDKTHTCPP CPAPELLGGP    120
```

```
SVFLFPPKPK DTLMISRTPE VTCVVVDVSH EDPEVKFNWY VDGVEVHNAK TKPREEQYNS    180
TYRVVSVLTV LHQDWLNGKE YKCKVSNKAL PAPIEKTISK AKGQPREPQV YTLPPSRDEL    240
TKNQVSLTCL VKGFYPSDIA VEWESNGQPE NNYKTTPPVL DSDGSFFLYS KLTVDKSRWQ    300
QGNVFSCSVM HEALHNHYTQ KSLSLSPGKK DPKFWVLVVV GGVLACYSLL VTVAFIIFWV    360
RSKRSLLHS DYMNMTPRRP GPTRKHYQPY APPRDFAAYR SLRVKFSRSA DAPAYQQGQN     420
QLYNELNLGR REEYDVLDKR RGRDPEMGGK PRRKNPQEGL YNELQKDKMA EAYSEIGMKG    480
ERRRGKGHDG LYQGLSTATK DTYDALHMQA LPPR                                514

SEQ ID NO: 37              moltype = AA   length = 514
FEATURE                    Location/Qualifiers
REGION                     1..514
                           note = fusion protein
source                     1..514
                           mol_type = protein
                           organism = synthetic construct
SEQUENCE: 37
MPLLLLLPLL WAGALAMATV KFTYQGEEKQ VDISKIKRVA RYGQGIYFDY GEGGGAWGYG     60
SVSEEDAPKE LLQMLEKQGG GGSGGGGSNW SHPQFEKEPK SPDKTHTCPP CPAPELLGGP    120
SVFLFPPKPK DTLMISRTPE VTCVVVDVSH EDPEVKFNWY VDGVEVHNAK TKPREEQYNS    180
TYRVVSVLTV LHQDWLNGKE YKCKVSNKAL PAPIEKTISK AKGQPREPQV YTLPPSRDEL    240
TKNQVSLTCL VKGFYPSDIA VEWESNGQPE NNYKTTPPVL DSDGSFFLYS KLTVDKSRWQ    300
QGNVFSCSVM HEALHNHYTQ KSLSLSPGKK DPKFWVLVVV GGVLACYSLL VTVAFIIFWV    360
RSKRSLLHS DYMNMTPRRP GPTRKHYQPY APPRDFAAYR SLRVKFSRSA DAPAYQQGQN     420
QLYNELNLGR REEYDVLDKR RGRDPEMGGK PRRKNPQEGL YNELQKDKMA EAYSEIGMKG    480
ERRRGKGHDG LYQGLSTATK DTYDALHMQA LPPR                                514

SEQ ID NO: 38              moltype = AA   length = 544
FEATURE                    Location/Qualifiers
REGION                     1..544
                           note = fusion protein
source                     1..544
                           mol_type = protein
                           organism = synthetic construct
SEQUENCE: 38
MPLLLLLPLL WAGALAMVSD VPRDLEVVAA TPTSLLISWY YPNASHAGYY RITYGETGGN     60
SPVQEFTVPF SIRYTIATIS GLKPGVDYTI TVYAVTDYAY YYRLSEPISI NYRTGGGGSG    120
GGGSDPAEPK SPDKTHTCPP CPAPELLGGP SVFLFPPKPK DTLMISRTPE VTCVVVDVSH    180
EDPEVKFNWY VDGVEVHNAK TKPREEQYNS TYRVVSVLTV LHQDWLNGKE YKCKVSNKAL    240
PAPIEKTISK AKGQPREPQV YTLPPSRDEL TKNQVSLTCL VKGFYPSDIA VEWESNGQPE    300
NNYKTTPPVL DSDGSFFLYS KLTVDKSRWQ QGNVFSCSVM HEALHNHYTQ KSLSLSPGKK    360
DPKFWVLVVV GGVLACYSLL VTVAFIIFWV RSKRSLLHS DYMNMTPRRP GPTRKHYQPY     420
APPRDFAAYR SLRVKFSRSA DAPAYQQGQN QLYNELNLGR REEYDVLDKR RGRDPEMGGK    480
PRRKNPQEGL YNELQKDKMA EAYSEIGMKG ERRRGKGHDG LYQGLSTATK DTYDALHMQA    540
LPPR                                                                 544

SEQ ID NO: 39              moltype = AA   length = 604
FEATURE                    Location/Qualifiers
REGION                     1..604
                           note = fusion protein
source                     1..604
                           mol_type = protein
                           organism = synthetic construct
SEQUENCE: 39
METDTLLLWV LLLWVPGSTG DGHHHHHHGS LQDSEVNQEA KPEVKPEVKP ETHINLKVSD     60
GSSEIFFKIK KTTPLRRLME AFAKRQGKEM DSLTFLYDGI EIQADQTPED LDMEDNDIIE    120
AHREQIGGGG GSGGGGSVSD VPRDLEVVAA TPTSLLISWY YPNASHAGYY RITYGETGGN    180
SPVQEFTVPF SIRYTIATIS GLKPGVDYTI TVYAVTDYAY YYRLSEPISI NYRTGGGGSG    240
GGGSNWSHPQ FEKTTTPAPR PPTPAPTIAS QPLSLRPEAS RPAAGGAVHT RGLDFASDIY    300
IWAPLAGTCG VLLLSLVITL YCKRGRKKLL YIFKQPFMRP VQTTQEEDGC SCRFPEEEEG    360
GCELSRGSGS GSGSMGVQVE TISPGDGRTF PKRGQTCVVH YTGMLEDGKK VDSSRDRNKP    420
FKFMLGKQEV IRGWEEGVAQ MSVGQRAKLT ISPDYAYGAT GHPGIIPPHA TLVFDVELLK    480
LEGSGSGSGS SLRVKFSRSA DAPAYKQGQN QLYNELNLGR REEYDVLDKR RGRDPEMGGK    540
PRRKNPQEGL YNELQKDKMA EAYSEIGMKG ERRRGKGHDG LYQGLSTATK DTYDALHMQA    600
LPPR                                                                 604

SEQ ID NO: 40              moltype = AA   length = 636
FEATURE                    Location/Qualifiers
REGION                     1..636
                           note = fusion protein
source                     1..636
                           mol_type = protein
                           organism = synthetic construct
SEQUENCE: 40
MPLLLLLPLL WAGALAMERD CRVSSFRVKE NFDKARFSGT WYAMAKKDPE GLFLQDNIVA     60
EFSVDETGQM SATAKGRVRL LNNWDVCADM VGTFTDTEDP AKFKMKYWGV ASFLQKGNDD    120
HWIVDTDYDT YAVQYSCRLL NLDGTCADSY SFVFSRDPNG LPPEAQKIVR QRQEELCLAR    180
QYRLIVHNGY CDGRSERNLL GGGGSGGGGS NWSHPQFEKE PKSPDKTHTC PPCPAPELLG    240
```

```
GPSVFLFPPK PKDTLMISRT PEVTCVVVDV SHEDPEVKFN WYVDGVEVHN AKTKPREEQY    300
NSTYRVVSVL TVLHQDWLNG KEYKCKVSNK ALPAPIEKTI SKAKGQPREP QVYTLPPSRD    360
ELTKNQVSLT CLVKGFYPSD IAVEWESNGQ PENNYKTTPP VLDSDGSFFL YSKLTVDKSR    420
WQQGNVFSCS VMHEALHNHY TQKSLSLSPG KKDPKFWVLV VVGGVLACYS LLVTVAFIIF    480
WVRSKRSRLL HSDYMNMTPR RPGPTRKHYQ PYAPPRDFAA YRSLRVKFSR SADAPAYQQG    540
QNQLYNELNL GRREEYDVLD KRRGRDPEMG GKPRRKNPQE GLYNELQKDK MAEAYSEIGM    600
KGERRRGKGH DGLYQGLSTA TKDTYDALHM QALPPR                              636

SEQ ID NO: 41          moltype = DNA  length = 50
FEATURE                Location/Qualifiers
misc_feature           1..50
                       note = FN3 primer
source                 1..50
                       mol_type = other DNA
                       organism = synthetic construct
SEQUENCE: 41
cgacgattga aggtagatac ccatacgacg ttccagacta cgctctgcag              50

SEQ ID NO: 42          moltype = DNA  length = 50
FEATURE                Location/Qualifiers
misc_feature           1..50
                       note = FN3 primer
source                 1..50
                       mol_type = other DNA
                       organism = synthetic construct
SEQUENCE: 42
atctcgagct attacaagtc ctcttcagaa ataagctttt gttcggatcc              50
```

LIGAND REGULATED PROTEIN-PROTEIN INTERACTION SYSTEM

RELATED APPLICATIONS

This application is a continuation of, and claims priority under 35 U.S.C. 120 from U.S. application Ser. No. 16/954,914, filed Jun. 17, 2020, which claims the benefit of International Patent Application No. PCT/EP2018/086299 filed on Dec. 20, 2018, and which claims the benefit of European Application Nos. EP17208924.5, filed Dec. 20, 2017; EP18160863.9, filed Mar. 9, 2018; and EP18202544.5, filed Oct. 25, 2018, all of which are incorporated by reference.

INCORPORATION BY REFERENCE OF SEQUENCE LISTING XML

Sequence Listing XML file "1DD3262.xml" created on Aug. 26, 2023, having the size of 8,100 bytes is herein incorporated into this application.

BACKGROUND

The present invention discloses ligand regulated protein-protein interaction systems and their use in diagnosis and therapy, especially in tumour therapy.

Protein-protein interactions (PPIs) are the physical contacts of high specificity established between two or more protein molecules as a result of biochemical events steered by electrostatic forces including the hydrophobic effect. Many are physical contacts with molecular associations between chains that occur in a cell or in a living organism in a specific biomolecular context. PPIs have also been used in the prior art for establishing screening systems or defined switches for pharmaceutical purposes, especially in human medicine.

A specific example of PPIs is dimerization, especially chemically induced dimerization (CID) by small molecules. There are several systems for CID of proteins by small molecules. In these systems PPIs, i.e. homo- or heterodimerization, can only occur in the presence of a small molecule, which thus acts as a chemical dimerizer. In most cases, the dimerizing proteins, or respective domains thereof, are expressed as parts of fusion constructs containing the proteins of interest. Some of the systems are functional not only inside cells but also in the oxidative environment outside from cells. Until now CID systems mainly have been used for, e.g., regulating enzyme function, signal transduction, gene transcription, genome editing (by e.g. CRISPR/Cas), protein stability, and for generating logic gates. CID systems are also increasingly considered for clinical applications, as e.g., for regulating the function of T cells modified with a chimeric antigen receptor. The most frequently used system is based on FRB/FBKP-domains for heterodimerization or a mutant FKBP-domain for homodimerization. Several rapamycin derivatives have been developed, but they have not yet solved the problem of simultaneously regulating two processes in the same cell. Such functionality has been introduced by the more recent development of CID systems, which are based on different proteins and also different small molecules. These systems work well in vitro, however, their use in vivo is limited. A much higher impact would have the development of CID systems that are suited for in vivo and even clinical application and for simultaneous control of multiple processes. The current systems are not suited for this purpose, since they are based on xenogeneic proteins and are thus expected to be highly immunogenic, and/or since the small molecules are not suited for in vivo application.

The FKBP-based system for homodimerization is the most advanced system and has been in clinical use for several years for inducing apoptosis in administered T cells. It is based on a human protein, depends on an inert molecule and is fully orthogonalized, i.e., the dimerizer does not bind to endogenous proteins and the mutated FKBP domain binds only the synthetic dimerizer. This process of insulating a protein ligand pair, called "orthogonalization", prevents unwanted interaction in both directions and is essential for the use of CID systems in cellular systems. In the case of heterodimerization even the most advanced human protein based system (FKBP/FRB-system) is still not fully orthogonal. Engineering of the protein binding pocket and complementarily of the small molecule was performed only for the interaction of the rapalog with FRB but not with FKBP, which is still based on the wildtype FBKP domain. Due to the binding mode of rapalogues to FRB and FKBP (see PDB 1NSG for the structure), redesigning the rapalogues for orthogonalization and for pharmacokinetic optimization poses a serious obstacle. Furthermore, the synthesis of rapalogues is difficult, potential contamination with rapamycin is a danger, and the molecules are not clinically approved.

Examples for CID systems have been disclosed in WO 2014/127261 A1 and WO 2017/032777 A1. Voss et al. (Curr. Op. Chem. Biol. 28 (2015): 194-201) disclose chemically induced dimerization systems, mainly rapamycin-based CID systems, and their reversible and spatiotemporal control of protein function in cells by using such CIDs. As a result, however, it was reported that these current CID systems, even these advanced rapamycin-based CID systems, can still induce undesired heterodimerization of FKBP and FRB. DeRose et al. (Europ. J. Physiol. 465 (2013): 409-417) review CID techniques to resolve problems in cell biology.

It is an object of the present invention to provide ligand regulated PPI systems (LRPPI) that can be regulated by small molecules for inducing dimerization of interaction partners and which are advantageous compared to existing systems. More specifically, novel LRPPI systems should be applicable in vivo, especially for the treatment of human patients, without the risk of adverse reactions or at least with reduced adverse reactions. It is a further object to provide means for tumour treatment, especially immunotherapy concepts for the treatment of tumours.

SUMMARY

Therefore, the present invention provides a ligand regulated protein-protein interaction system based on a lipocalin-fold molecule comprising:
  (a) a lipocalin-fold molecule
  (b) a lipocalin-fold ligand with a low molecular weight of 1500 Da or below, and
  (c) a lipocalin-fold binding interaction partner,
  wherein the lipocalin-fold molecule can bind to the lipocalin-fold ligand; and
  wherein the lipocalin-fold molecule bound to the lipocalin-fold ligand binds to the lipocalin-fold binding interaction partner with an affinity which is at least 10-fold higher than the affinity of the lipocalin-fold molecule not bound to the lipocalin-fold ligand,
  and wherein the lipocalin-fold binding interaction partner is not a naturally occurring protein which has an affinity of <10 µM to any naturally occurring lipocalin-fold molecule in the presence of any lipocalin-fold ligand.

The present invention also refers to a ligand regulated protein-protein interaction system based on a lipocalin-fold molecule comprising:
(a) a lipocalin-fold molecule
(b) a lipocalin-fold ligand with a low molecular weight of 1500 Da or below, and
(c) a lipocalin-fold binding interaction partner,
wherein the lipocalin-fold molecule has at least a first conformation when the lipocalin-fold ligand is not bound to the lipocalin-fold molecule and at least a second conformation when the lipocalin-fold ligand is bound to the lipocalin-fold molecule; and
wherein the lipocalin-fold molecule bound to the lipocalin-fold ligand in the second conformation binds to the lipocalin-fold binding interaction partner with an affinity which is at least 10-fold higher than the affinity of the lipocalin-fold molecule not bound to the lipocalin-fold ligand in the first conformation,
and wherein the lipocalin-fold binding interaction partner is not a naturally occurring protein which has an affinity of <10 µM to any naturally occurring lipocalin-fold molecule in the presence of any lipocalin-fold ligand.

The present invention is based on the high flexibility of the lipocalin-fold molecule system for binding to its binding partners ("lipocalin-fold binding interaction partner") with and without involvements of other molecules, especially small molecules which can be used as pharmaceutical agents. Although the system is based on naturally occurring counterparts, the systems of the present invention are artificial. This means that the lipocalin-fold molecule and/or the lipocalin-fold binding interaction partner may be derived from naturally occurring scaffolds by adapting the binding affinities and specificities of the three essential components of the present system (lipocalin-fold molecule, lipocalin-fold ligand and the lipocalin-fold binding interaction partner) to the binding specificities needed, especially those which are required in a targeted and specific pharmaceutical intervention on human patients.

The feature that the lipocalin-fold binding interaction partner is not a naturally occurring binding partner of a naturally occurring lipocalin-fold molecule is important for reducing or avoiding significant cross-reactivity (which is disadvantageous for the intended use of the present invention for pharmaceutical application). Such cross-reactivity could lead to side-effects which can eventually become severe (such side effects could also be hard to predict, if naturally occurring lipocalin-fold binding interaction partners were part of the "on-switch" system based on a lipocalin-fold molecule).

In the course of the present invention, it was found out that LRPPI systems based on lipocalin-fold molecules have surprisingly advantageous properties which make them excellently suitable for establishing LRPPI systems which have also the capability of working in vivo in human pharmaceutical therapy. This is not only based on the fact that lipocalin-fold molecule affinities for lipocalin-fold ligands are easily "tunable", specifically in the micro- and nanomolar range, but also due to the robust architecture of the central structure of the lipocalin-fold molecule (see further disclosure to the "lipocalin-fold", below) and the ability of some lipocalin-fold ligands to bind in the lipocalin-fold molecule. Due to these excellent properties, the LRPPI systems according to the present invention can be designed very specific, robust and sensitive to allow use in human medicine.

The present LRPPI system is therefore based on three essential components: the lipocalin-fold molecule ("a" in FIG. 1), the lipocalin-fold ligand ("b" in FIG. 1) and the lipocalin-fold binding interaction partner ("c" in FIG. 1).

The "lipocalin-fold molecule" according to the present invention can be any naturally occurring lipocalin-fold molecule or derived version thereof that is part of the "lipocalin-fold" superfamily of proteins according to the Structural Classification of Proteins (SCOP) database (version 1.75) (Murzin et al. J Mol Biol. 1995; 247(4):536-540). It is this structural motif of the "lipocalin-fold" proteins that allows the generation of the flexible LRPPI systems according to the present invention. Including the lipocalin-fold molecules in the LRPPI system according to the present invention was thus a crucial step towards enabling flexible engineering of orthogonal LRPPI systems for clinical use. In the course of the present invention, this lipocalin-fold was identified as a uniquely shaped scaffold that can inherently bind a large variety of structurally different small molecules ("lipocalin-fold ligands" (or "ligands") according to the present invention) and can be engineered even for binding of small molecules that initially cannot be captured. A lipocalin-fold protein contains a small characteristic 8- or 10-stranded up-and-down β-barrel motif, in which the antiparallel β-strands are arranged in a +1 topology and which has evolved to wrap around mostly hydrophobic small molecule ligands (Lakshmi et al. PLoS One. 2015; 10 (8): e0135507; Zhang et al., PLoS One. 2012; 7 (5): e36772; Smathers et al., Hum Genomics. 2011; 5(3):170-191; Grzyb et al., J Plant Physiol. 2006; 163(9):895-915; Flower et al., Biochim Biophys Acta. 2000; 1482 (1-2):9-24; Schiefner et al., Acc Chem Res. 2015; 48 (4):976-985). In the SCOP database (version 1.75) the lipocalin-fold comprises only the lipocalin superfamily (Lakshmi et al. PLoS One. 2015; 10 (8): e0135507). Among the 9 families that are assigned to the lipocalin superfamily, retinol binding protein-like and fatty acid binding protein-like proteins comprise the lipocalins (LCNs) and intracellular lipid binding proteins (iLBPs), respectively, and are the most relevant families. LCNs are 8-stranded β-barrel proteins (molecular mass roughly 20 kDa) (Schiefner et al., Acc Chem Res. 2015; 48 (4):976-985) and iLBPs are 10-stranded β-barrel proteins (molecular mass roughly 15 kDa) that comprise FABPs (fatty acid binding proteins), CRBPs (cellular retinol binding proteins) and CRABPs (cellular retinoic acid binding proteins) (Smathers et al., Hum Genomics. 2011; 5(3):170-191). It is assumed that lipocalin-fold proteins have evolved from a common ancestor by gene duplication and evolutionary divergence for adapting to capture a multitude of different small molecules. LCNs have already evolved in bacteria (>600 LCNs have been described among species; the human genome encodes at least 15 members), and iLBPs have likely evolved in animals after divergence from fungi and plants (the human genome encodes 10 FABPs and 6 retinoid binding proteins; Lakshmi et al. PLoS One. 2015; 10 (8): e0135507; Zhang et al., PLoS One. 2012; 7 (5): e36772; Smathers et al., Hum Genomics. 2011; 5(3):170-191). All these proteins have maintained a striking structural homology despite very low sequence homology (for some FABPs around 20% and for many LCNs below 30%), which illustrates the extraordinary high tolerance of the β-barrel structure of the lipocalin superfamily to mutations in virtually all regions of the structure for adaption to binding of different ligands. In fact, it has not been possible to define any sequence motif that is common to all members of the lipocalin superfamily, i.e. especially the lipocalins and iLBPs (Flower et al., Biochim Biophys Acta. 2000; 1482 (1-2):9-24).

This extraordinary flexible β-barrel structure of the lipocalin-fold is used according to the present invention as a broad platform (based on the "lipocalin-fold molecule") for generating a novel family of LRPPI systems that can be regulated by ligands which insert into the hydrophobic pocket of the lipocalin-fold. Such regulating lipocalin-fold ligands can be chosen from a large pool of possible molecules with different characteristics. The ligand-bound lipocalin-fold molecule can be used as a target molecule that is recognized by another engineered protein, i.e. the lipocalin-fold binding interaction partner, in a ligand-dependent manner. That is, in this embodiment, the lipocalin-fold binding interaction partner is engineered to specifically recognize the lipocalin-fold molecule with higher affinity if the ligand is inserted into the hydrophobic pocket. This other engineered protein can be, but is not limited to, an antibody, an antibody fragment or any other protein that can be engineered for antigen binding. Alternatively, the ligand-bound lipocalin-fold molecule, i.e. the lipocalin-fold thereof, may be engineered for binding to another molecule, i.e. the lipocalin-fold binding interaction partner (e.g. a protein, carbohydrate, lipid, among others) in a ligand-dependent manner. That is, in this embodiment, in the ligand-bound state the engineered lipocalin-fold molecule is able to bind to the other interaction partner with strongly enhanced affinity. As a consequence, the ligand can be used for regulating the interaction of the lipocalin-fold molecule with the lipocalin-fold binding interaction partner.

These regulating lipocalin-fold ligands can include clinically applicable molecules with beneficial pharmacokinetics. Moreover, it is possible to select lipocalin-fold ligands that are orthogonal to each other, thereby even enabling separate regulation of multiple processes in parallel. All this founds firstly on the capacity of this β-barrel structure to inherently accommodate a multitude of different ligands in its calyx-like binding pocket and secondly on its unique tolerance to mutations, which enables engineering of high affinity and specificity to a broad spectrum of non-natural ligands as previously disclosed (e.g. DE 19742706 A1, WO 99/016873 A1, EP 1 017 814 B1, WO 2012/065978 A1, WO 2016/113203 A1, Skerra, Biochim Biophys Acta. 2000; 1482 (1-2):337-350; Korndorfer et al., Proteins 2003; 53(1): 121-129; Korndorfer et al., J Mol Biol. 2003; 330(2):385-396; Kim et al., J Am Chem Soc. 2009; 131(10):3565-3576; Schlehuber et al., Biophys Chem. 2002; 96 (2-3):213-228). Just these two unique features of the β-barrel structure enable orthogonalization by engineering of the binding pocket for binding the ligands with high affinity and specificity, instead of redesigning the ligands, which significantly reduces the clinical entry barrier and allows for choosing molecules from a large pool of possible candidates. An additional degree of flexibility and specificity may be introduced by lipocalin-fold binding interaction partners that are engineered for specifically recognizing the β-barrel containing lipocalin-fold molecules in the ligand-bound state. For this purpose, the ligand-loaded β-barrels (i.e. the ligand-loaded lipocalin-fold molecules) may be used as antigens for binder screening from appropriate libraries. Alternatively, the lipocalin-fold can also be engineered as ligand-dependent binders. The latter is based on the fact that lipocalin-fold molecules can not only be engineered for small molecule binding but also for binding of large proteins. This has been meanwhile exemplified in the form of so-called "anticalins" or "muteins of lipocalin" with a range of protein antigens and has been applied for generating soluble blocking agents and novel tumour binding moieties in chimeric antigen receptors (e.g. DE 19742706 A1, WO 99/016873 A1, EP 1 017 814 B1, WO 2012/065978 A1, WO 2016/113203 A1, Richter et al., FEBS Lett. 2014; 588 (2):213-218; Schonfeld et al., Proc Natl Acad Sci USA. 2009; 106(20):8198-8203; Gebauer et al., J Mol Biol 2013; 425 (4):780-802; Barinka et al., Protein Eng Des Sel. 2016; 29(3):105-115). Accordingly, there are already numerous examples of lipocalin-fold molecules available in the prior art which may be applied in the LRPPI system according to the present invention, such as the naturally occurring lipocalins and engineered lipocalins ("anticalins", "muteins of lipocalin", etc.). In contrast to the previous strategies provided on the basis of engineering LCN-based binder scaffolds, the present invention provides the engineering of lipocalin-fold based LRPPI systems for regulating PPIs by addition of small molecules.

Accordingly, any molecule comprising the lipocalin-fold as the central structural element may be used or adapted to be used in the LRPPI system according to the present invention. The LRPPI systems according to the present invention can easily be optimised and tuned with respect to affinity of the lipocalin-fold molecules to lipocalin-fold ligands and also with respect to differences in the affinity of lipocalin-fold molecules to lipocalin-fold binding interaction partners in absence and presence of lipocalin-fold ligands. In the present invention the "bound" or "unbound" state of the LRPPI system, i.e., a lipocalin-fold molecule "bound" or "unbound" to a lipocalin-fold ligand, is referred to a difference in affinity of the lipocalin-fold molecule to the lipocalin-fold binding interaction partner of at least ten-fold. However, preferred embodiments apply an even more significant affinity difference between the (at least) two states of the lipocalin-fold molecules in absence and presence of lipocalin-fold ligands. This is why the difference in affinity is preferably at least 20-fold, especially at least 50-fold. The present invention allows differences in affinity to be designed and tuned even further, e.g. at least 100-fold, at least 200-fold, at least 500-fold or at least 1000-fold. This increase in affinity difference may be specifically advantageous in the human therapy environment, especially as a safety measure to exclude unwanted side effects or toxicity.

Although the LRPPI systems according to the present invention are based on the advantageous properties of the naturally occurring lipocalin-fold molecules, the LRPPI systems according to the present invention are artificial systems which are designed to provide a suitable pharmaceutical system. This means that the LRPPI systems according to the present invention cannot have a naturally occurring counterpart (because this could not be used for the purpose intended by the present invention (since the natural systems have to fulfil their naturally intended purpose)). In this context, it is important to note here that in the course of the present invention the surprising observation was made that the LRPPI systems according to the present invention are highly flexible regarding the type (i.e. the structure (or fold)) of the lipocalin-fold binding interaction partner. The LRPPI systems described in Example 1 of the present invention demonstrate that different types of proteins with structurally very different binding sites (located on either rigid β-strands or loop regions, respectively) can be used as lipocalin-fold binding interaction partners. Moreover, the proteins used as lipocalin-fold binding interaction partners in Example 1 are not (and are not mutants of) any naturally occurring lipocalin-fold binding interaction partners. Instead, the lipocalin-fold binding interaction partners used in Example 1 are either mutated versions of the protein Sso7d (a DNA-binding protein from the archaeon *Sulfolobus solfataricus*) or mutated versions of the $10^{th}$ type III domain of human fibronectin (FN3), demonstrating that structurally distinct proteins (or protein domains) derived from molecules with completely different original function can efficiently act as lipocalin-fold binding interaction partners according to the present invention. Accordingly, to create LRPPI systems which are more independent from naturally occurring PPI systems and to reduce the risk of disadvantageous cross-reactivity with endogenous lipocalin-fold binding interaction partners, the lipocalin-fold binding interaction partners in the LRPPI systems according to the present invention are not (and are preferably also not derived from) naturally occurring lipocalin-fold binding interaction partners. More precisely, the lipocalin-fold binding interaction partner (or any domain of it that mediates binding to the lipocalin-fold molecule) is not and is preferably also not derived from a naturally occurring protein which has an affinity of <10 µM to any naturally occurring lipocalin-fold molecule (in the presence of any lipocalin-fold ligand), wherein "being derived from" is defined as containing at least one segment of at least 50 consecutive amino acids with an amino acid sequence that is at least 98% identical with the amino acid sequence of any segment of that naturally occurring protein and which has an affinity of <10 µM to any naturally occurring lipocalin-fold molecule (in the presence of any lipocalin-fold ligand).

Accordingly, a preferred embodiment of the LRPPI system according to the present invention employs a lipocalin-fold binding interaction partner that does not contain a segment of at least 50 consecutive amino acids with an amino acid sequence that is at least 98% identical with the amino acid sequence of any segment of a naturally occurring protein and which has an affinity of <400 nM, preferably <2 µM, especially <10 µM to any naturally occurring lipocalin-fold molecule, especially in the presence of a lipocalin-fold ligand. Preferably, the lipocalin-fold binding interaction partner does not contain a domain of a naturally occurring protein that mediates binding to a naturally occurring lipocalin-fold molecule. This further safeguards lack of cross-reactivity. Preferably, the affinity of the lipocalin-fold binding interaction partner (used in the LRPPI systems according to the present invention) to the lipocalin-fold molecule when bound to the lipocalin-fold ligand or in the second conformation, respectively, is below 10 µM, preferably below 2 µM, especially below 400 nM.

In order to further lowering the risk of immunogenicity in a human patient, the ligand regulated protein-protein interaction system according to the present invention preferably comprises a lipocalin-fold binding interaction partner that is not a homolog of a different species than human of a naturally occurring human lipocalin-fold binding interaction partner. Even more preferred, the lipocalin-fold molecule is not even a homolog of a different species than human of a naturally occurring human lipocalin-fold molecule.

Preferred ligand regulated protein-protein interaction systems according to the present invention apply molecules as lipocalin-fold ligands which are useable in a pharmaceutical environment, preferably molecules which are suitable and appropriate to be applied to humans. Accordingly, preferred embodiments of the present invention comprise a lipocalin-fold ligand which is a pharmaceutically active molecule, especially a pharmaceutically active molecule with a therapeutic activity in human patients. In this connection, molecules are preferred as lipocalin-fold ligands which can be effectively administered orally. This means that such molecules are suitable for oral administration and are taken up by the individual to whom the molecule is administered through intestinal absorption. Also molecules are preferred as lipocalin-fold ligands which can be effectively administered intravenously. This means that the molecule can be administered intravenously without significant side effects to a patient. Specifically preferred lipocalin-fold ligands are suitable for effective administration in both manners, intravenously and orally, to a human patient. Preferred lipocalin-fold ligands are therefore molecules which are (or have been) registered drugs for human use for which e.g. a valid marketing authorisation is present, e.g. in either the EU or the US, or both.

This artificial character of the LRPPI systems according to the present invention enables the proper regulation of the system (e.g. by the small molecule ligand) also in vivo (as needed to solve the object of the present invention). In a specifically preferred embodiment, both main system components of the ligand regulated protein-protein interaction system according to the present invention, namely, the lipocalin-fold molecule and the lipocalin-fold binding interaction partner and/or any domain of them that mediates binding to each other with an affinity (in the presence of a lipocalin-fold ligand) of <10 µM, preferably <2 µM, especially <400 nM, are not part of a naturally occurring LRPPI system, i.e. a biological pathway, wherein the physiological function is performed by such a system. Accordingly, in such a preferred embodiment, both the lipocalin-fold molecule and the lipocalin-fold binding interaction partner are therefore not naturally occurring proteins, but mutated or artificially designed non-natural proteins (i.e. proteins with no native counterpart existing in nature).

Moreover, in order to design an LRPPI system that is independent from naturally occurring LRPPI or PPI systems, the LRPPI systems according to the present invention are artificial systems in which preferably the lipocalin-fold molecule and the lipocalin-fold binding interaction partner are not derived from naturally occurring molecules that bind to each other with an affinity of <10 µM. This means that (1) if the lipocalin-fold molecule used in a given LRPPI system according to the present invention is engineered, the naturally occurring lipocalin-fold molecule, that it is derived from, does not bind with an affinity of <10 µM to the lipocalin-fold binding interaction partner used in that LRPPI system; or (2) if the lipocalin-fold binding interaction partner used in a given LRPPI system according to the present invention is engineered, the naturally occurring molecule, that this lipocalin-fold binding interaction partner is derived from, does not bind with an affinity of <10 µM to the lipocalin-fold molecule used in that LRPPI system; or (3) if both the lipocalin-fold molecule and the lipocalin-fold binding interaction partner used in a given LRPPI system according to the present invention are engineered, the naturally occurring molecules, which the lipocalin-fold molecule and the lipocalin-fold binding interaction partner are derived from, respectively, do not bind to each other with an affinity of <10 µM.

Moreover, to avoid any disadvantageous cross-reactivity, the lipocalin-fold binding interaction partner used in a given LRPPI system according to the present invention preferably does not bind with an affinity of <1 µM (neither in the presence nor in the absence of a lipocalin-fold ligand) to any naturally occurring lipocalin-fold molecule except for (1) the naturally occurring lipocalin-fold molecule used in that LRPPI system (if a naturally occurring lipocalin-fold molecule is used in that LRPPI system) or the naturally occurring lipocalin-fold molecule that the β-barrel sequence of the engineered lipocalin-fold molecule used in that LRPPI system was derived from and except for (2) the naturally occurring lipocalin-fold molecules which are homologs (i.e.

homologous lipocalin-fold molecules from other species) of the naturally occurring lipocalin-fold molecule used in that LRPPI system (if a naturally occurring lipocalin-fold molecule is used in that LRPPI system) or the naturally occurring lipocalin-fold molecules which are homologs of the naturally occurring lipocalin-fold molecule that the β-barrel sequence of the engineered lipocalin-fold molecule used in that LRPPI system was derived from.

A highly attractive field for clinical application of LRPPI systems based on lipocalin-fold molecules according to the present invention is for regulating the function of T cells modified with chimeric antigen receptors (CARs) instead of using the FKBP-based systems for homo- and heterodimerization for regulating the CAR T cell function. Importantly, the function of currently applied CARs cannot be regulated in a clinically applicable manner. Instead, inducing apoptosis in the CAR expressing effector cells is the only clinically applicable safety mechanism in the CAR field until now (Jones et al., Front Pharmacol. 2014; 5:254). The most advanced strategies for regulating the function of the CAR molecule itself employ the FRB/FKBP-based system in different versions either for LRPPI (WO 2014/127261 A1, WO 2015/017214 A1, EP 3 087 101 A1, US 2017/0081411 A1) or for regulating protein stability (WO 2017/032777 A1). As mentioned above, however, the FRB/FKBP system is associated with severe problems in any potential clinical application (Sun et al., Cell Res. 2015; 25(12):1281-1282). Thus, alternatively, the lipocalin-fold molecule based LRPPI systems according to the present invention are highly attractive for integration into CARs in order to control T cell activation upon CAR mediated target antigen recognition by administering small molecules. In contrast to the rather problematic FRB/FBKP-system the lipocalin-fold based LRPPI systems according to the present invention can pave the way for broad clinical application of switchable CARs.

The LRPPI system according to the present invention and shown in FIG. 1 can be engineered using two strategies in principle: In strategy A, the lipocalin-fold binding interaction partner "c" (which may preferably be fused (+/−flexible linker) to a protein "II") is a binder, which binds to the barrel-containing structure of the lipocalin-fold molecule "a" with higher affinity when lipocalin-fold ligand "b" is present. The lipocalin-fold binding interaction partner "c" can e.g. be generated either by immunization of animals with ligand ("b")-loaded lipocalin-fold molecule, or by state of the art protein engineering methods such as phage display, yeast display, bacterial display, mammalian cell display, ribosome display, mRNA display or covalent DNA display, among others (Sergeeva et al., Advanced Drug Delivery Reviews 2006; 58:1622-1654). In strategy B, the lipocalin-fold molecule "a" itself can be engineered as a binder that after loading with a lipocalin-fold ligand "b" can bind with higher affinity to a chosen lipocalin-fold binding interaction partner "c" (which again can (according to a preferred embodiment) be fused to protein "II" or itself is a protein or non-protein antigen "II" (e.g. a tumor associated antigen)). The lipocalin-fold molecule "a" and the lipocalin-fold binding interaction partner "c" can be fused to the N- or C-termini or also internal sites of proteins "I" and "II" (see FIG. 1B). The lipocalin-fold molecule "a" may be engineered for increasing the affinity to a chosen small molecule lipocalin-fold ligand "b" and/or for decreasing the affinity towards endogenous natural lipocalin-fold ligands. Furthermore, the lipocalin-fold structure of lipocalin-fold molecule "a" may also be engineered for preventing or reducing interaction with natural interaction partners.

Preferably, the lipocalin-fold ligand induces a conformational change in the lipocalin-fold molecule "a", which facilitates the selection of a ligand-dependent binder (lipocalin-fold binding interaction partner) "c" (or also the selection of a ligand-dependent lipocalin-fold molecule "a" when in turn used as a binder). The lipocalin-fold ligand "b" can, but does not need to, interact directly with "c" or protein "II". However, in cases where binding of molecule "b" results only in rigidification of the structure of the lipocalin-fold molecule "a" with rather limited conformational selection, any direct contribution of molecule "b" for increasing the affinity of the interaction of "a" and "c" is beneficial.

Depending on the application, the LRPPI system can—according to a specific embodiment—be further employed in a strategic variant for regulating dimerization of two identical or different lipocalin-fold molecules (the first one being the lipocalin-fold molecule "a" according to the present invention, the second one being a "lipocalin-fold binding interaction partner" in the system according to the present invention (although being a "lipocalin-fold molecule", such second lipocalin-fold molecule would serve as the binding partner of the first lipocalin-fold molecule according to the present invention)). Accordingly, this specific embodiment uses lipocalin-fold ligands "b" with two identical or different head groups, respectively, to form a LRPPI with two lipocalin-fold molecules (different or the same (i.e. homodimerization or heterodimerization)), in analogy to existing LRPPI systems (Rutkowska et al., Angew Chem Int Ed Engl. 2012; 51(33):8166-8176). One of the two lipocalin-fold molecules serves then (formally) as a "lipocalin-fold binding interaction partner" within the definitions in the system according to the present invention.

As already outlined above, the lipocalin-fold molecule according to the present invention may be any suitable molecule comprising the structural element of a lipocalin-fold. The lipocalin-fold of the lipocalin-fold molecule according to the present invention ("a") can be derived from the β-barrel of any known member of the LCN protein family or from the β-barrel of the iLBP protein family. This also includes LCN- and iLBP-variants, which deviate in the numbers of β-strands from the prototypic architecture as has been reported, e.g., for some LCNs (Papiz et al., Nature. 1986; 324(6095):383-385; Spinelli et al., Eur J Biochem. 2002; 269(10):2449-2456; Sevvana et al., J Mol Biol. 2010; 404(3):363-371). As LCNs have evolved for extracellular transport of small molecules and iLBPs have evolved for intracellular transport of many of the same molecules, the two β-barrel variants offer different advantages for application in oxidizing versus reducing environments outside and inside of cells. In principle, the lipocalin-fold of both families are suited for the flexible LRPPI systems according to the present invention as they have very similar structure and all can accommodate a large variety of lipocalin-fold ligands in their binding pocket with high affinity. However, lipocalin-fold molecules with known lipocalin-fold ligand induced conformational adaption and variants enabling a direct contribution of the lipocalin-fold ligand "b" in the interaction with the lipocalin-fold binding interaction partner "c" are preferred. The organisms of origin of the lipocalin-fold molecule can be selected according to the target organisms, in which the proteins are supposed to be expressed at maximum levels and with correct posttranslational modification. In this context LCNs have the advantage that they have evolved already in bacteria. However, the intended primary advantage of the β-barrel based LRPPI systems is their clinical applicability, thus, lipocalin-fold molecules of human protein origin are preferred.

Currently, human LCNs comprise 15 well characterized proteins and a couple of yet elusive members (Schiefner et al., Acc Chem Res. 2015; 48 (4):976-985). For the well characterized LCNs a large diversity in the size and shape of the binding pockets has been described as well as an accordingly highly diverse spectrum of lipocalin-fold ligands such as, e.g., simple fatty acids, glyco- and phospholipids, all-trans retinol, cholesterol, vanillin, imatinib, staurosporine, or even large, complex molecules such as bacillibactin and heme. This adaptiveness has been found to particularly depend on the length and the sequence of the four loops at the entry site of the β-barrel (Schiefner et al., Acc Chem Res. 2015; 48(4):976-985; Skerra, Biochim Biophys Acta. 2000; 1482 (1-2):337-350; Korndorfer et al., Proteins 2003; 53(1):121-129; Korndorfer et al., J Mol Biol. 2003; 330(2):385-396; Kim et al., J Am Chem Soc. 2009; 131(10):3565-3576; Schlehuber et al., Biophys Chem. 2002; 96 (2-3):213-228; Richter et al., FEBS Lett. 2014; 588 (2):213-218). Extensive conformational changes upon binding of different lipocalin-fold ligands so far have been reported for human and bovine retinol binding protein 4 (RBP4), human tear lipocalin (TLC) and human apolipoprotein M (ApoM) (Berni et al., FEBS Lett. 1992; 308(1): 43-45; Zanotti et al., J Biol Chem. 1993; 268(33):24873-24879; Zanotti et al., J Biol Chem. 1994; 269(47):29613-29620; Pattanayek et al., Protein Sci. 1999; 8(10):2027-2032; Motani et al., J Biol Chem. 2009; 284(12):7673-7680; Gasymov et al., Biochim Biophys Acta. 1998; 1386(1):145-156; Breustedt et al., Acta Crystallogr D Biol Crystallogr. 2009; 65 (Pt 10):1118-1125; Gasymov et al., Biochemistry. 2012; 51(14):2991-3002; Zhang et al., Sci Rep. 2016; 6:30655; Christoffersen et al., Proc Natl Acad Sci USA. 2011; 108 (23):9613-9618). Among them, human TLC is characterized by elevated conformational flexibility and an extraordinary flexible binding behavior compared to other LCNs (Schiefner et al., Acc Chem Res. 2015; 48 (4):976-985; Breustedt et al., Acta Crystallogr D Biol Crystallogr. 2009; 65 (Pt 10):1118-1125; Gasymov et al., Biochemistry. 2012; 51(14):2991-3002). In the case of the particularly well characterized native human RBP4 there are two loop regions, which undergo conformational alteration upon lipocalin-fold ligand binding and are involved in interaction with natural interaction partners transthyretin (TTR) (via EF loop, residues 89-101) and the receptor STRA6 (via CD loop, residues 59-68; Redondo et al., FASEB J. 2008; 22 (4):1043-1054). Meanwhile, several natural and synthetic retinoid and non-retinoid lipocalin-fold ligands for human RBP4 have been described (i.e., Fenretinide, N-Ethylretinamide, all-trans retinoic acid, retinyl acetate, axerophthene, A1120 (PubChem CID 25138295)), which induce conformational changes resulting in dissociation from TTR (Berni et al., FEBS Lett. 1992; 308(1):43-45; Zanotti et al., J Biol Chem. 1993; 268 (33):24873-24879; Zanotti et al., J Biol Chem. 1994; 269(47):29613-29620; Motani et al., J Biol Chem. 2009; 284(12):7673-7680; Coward et al., Anal Biochem. 2009; 384(2):312-320; Sharif et al., Anal Biochem. 2009; 392 (2):162-168). Reported crystal structures for human RBP4 illustrate that different lipocalin-fold ligands can induce different conformations in distinct loop regions of the LCN (e.g., protein data bank (PDB) 1RBP, 3FMZ and 2WR6 for retinol, A1120 and linoleic acid, respectively). Similar effects have been reported for ApoM (PDB 2YG2 and 2WEW for sphingosine-1-phosphate versus myristic acid; Christoffersen et al., Proc Natl Acad Sci USA. 2011; 108 (23):9613-9618).

For selecting appropriate lipocalin-fold molecules according to the present invention, differences with regard to existence of glycosylation sites, free cysteines, disulfide bridges, oligomerization behavior, ligand spectrum etc., and the necessity for removing more or less characterized interaction sites for preventing interaction with natural protein partners or lipid membranes can be considered (Schiefner et al., Acc Chem Res. 2015; 48(4):976-985). Among the human LCNs, RBP4, TLC and ApoM (UniProt IDs P02753, P31025, and 095445, respectively) are characterized by already known lipocalin-fold ligand induced conformational adaption and are thus preferred members of the lipocalin family for generating LRPPI systems according to the present invention. One additional preferred lipocalin molecule is the human neutrophil gelatinase-associated lipocalin (NGAL) (UniProt ID P80188), for which a very detailed structural knowledge with respect to interacting amino acid residues and binding pocket engineering has accumulated (Kim et al., J Am Chem Soc. 2009; 131(10):3565-3576; Schonfeld et al., Proc Natl Acad Sci USA. 2009; 106(20): 8198-8203; Barinka et al., Protein Eng Des Sel. 2016; 29(3):105-115; Gebauer et al., J Mol Biol 2013; 425(4):780-802; Bao et al., RSC Adv. 2015; 5(126):104363-104374; Eggenstein et al., J Struct Biol. 2014; 185(2):203-214). This is in particular due to the fact that its ligand binding pocket can easily be modified and was the basis of structurally resolved anticalins engineered for high affinity binding against different ligands.

Importantly, β-barrels of LCNs are not only an option for extracellular use but also for intracellular use of the LRPPI systems. This is based on the fact that, although all human LCNs have at least one disulfide bridge in their β-barrel structure, the β-barrel of, e.g., human TLC is functional and sufficiently stable also in the fully reduced state (Gasymov et al., Biochim Biophys Acta. 2011; 1814(5):671-683). Other LCNs could be more affected under reducing conditions, however, these proteins can be stabilized by e.g. inserting stabilizing mutations. The latter has been exemplified for a zinc-binding mutant of human RBP4, which was stabilized by introducing the five mutations A43L, A55V, A57I, H104W and Q117I (Skerra; Biochim Biophys Acta. 2000; 1482 (1-2):337-35049; Schmidt, Untersuchungen zur Proteinfaltung durch Protein-Design am Retinol-Bindungsprotein. Vol. ISBN 3-89675-314-2. München: Herbert Utz Verlag; 1998).

The LCN-derived β-barrels preferably represent the full-length coding sequences; signal peptides can be replaced; both, the N- and the C-terminal ends of the full length or trimmed β-barrels (i.e. lipocalin molecules) are suited for fusion to protein partners (with or without linker sequences), protein domains, peptides or single amino acids since the termini of the β-barrels are not involved in ligand binding (Skerra; Biochim Biophys Acta. 2000; 1482 (1-2):337-35049).

Possible sequence modifications can comprise:
a) Preferably, the engineering of the binding pocket of the lipocalin-fold molecules for increasing the affinity to a chosen ligand "b" and/or lowering the affinity to other lipocalin-fold ligands by directed evolution including any sort of random mutagenesis and subsequent selection or screening processes, such as phage display, yeast display, bacterial display, mammalian cell display, ribosome display, mRNA display or covalent DNA display, among others (Sergeeva et al., Advanced Drug Delivery Reviews 2006; 58:1622-1654). Alternatively, mutations can be based on in silico calculations and subsequently be introduced by site-directed mutagenesis (Whitehead et al., Methods Enzymol. 2013; 523:1-19; Strauch et al., Proc Natl Acad Sci USA 2014

Jan. 14; 111(2):675-80). Such engineering processes can require only limited mutagenesis at specific sites. If small molecules are chosen that initially do not bind the lipocalin-fold, then more extensive mutagenesis in or nearby the center of the binding pocket of the β-barrel may be required for generating mutants with binding capability (as described in DE 19742706 A1 and exemplified for several small molecules in Korndorfer et al., Proteins 2003; 53(1):121-129; Korndorfer et al., J Mol Biol. 2003; 330 (2):385-396; Kim et al., J Am Chem Soc. 2009; 131(10):3565-3576; Schlehuber et al., Biophys Chem. 2002; 96 (2-3):213-228). In the preferred case, this process is compatible with screening for lipocalin-fold ligand induced conformational changes. Such a screening process is feasible by employing proteins that can bind to these lipocalin-fold molecules in the absence of any ligand but dissociate upon lipocalin-fold ligand binding for selecting lipocalin-fold molecule mutants, which have maintained conformational switch behaviour. Such a protein can be the natural protein TTR in the case of RBP4 or other natural binding partners that bind to the respective lipocalin-fold molecule. Alternatively, binders, which have been separately engineered for binding to a chosen lipocalin-fold molecule in the absence of a ligand, may also be used for such a screening process. In a typical screening process, the lipocalin-fold molecule libraries are alternately screened for mutants that are capable for binding to these proteins in the absence of any ligand. Then the capability for lipocalin-fold ligand binding and conformational switching of the lipocalin-fold molecule is concomitantly selected by screening of the lipocalin-fold molecule libraries for non-binding to these proteins, or binding with lower affinity, in the presence of the lipocalin-fold ligand.

b) Additional mutagenesis (possibly, but not necessarily, after engineering of the binding pocket of the lipocalin-fold molecule for lipocalin-fold ligand binding) with a focus on the loop regions (as described in DE 19742706 A1), if the lipocalin-fold molecule is intended for use as a binder in the LRPPI system (instead of using it as an antigen); preferably, the lipocalin-fold molecule is engineered by directed evolution including any sort of random mutagenesis and subsequent selection or screening processes, such as phage display, yeast display, bacterial display, mammalian cell display, ribosome display, mRNA display or covalent DNA display, among others (Sergeeva et al., Advanced Drug Delivery Reviews 2006; 58:1622-1654). Maintenance of the capability for small molecule binding of the lipocalin-fold molecules may be warranted by alternating screening for antigen binding of the lipocalin-fold molecules in presence of the lipocalin-fold ligand and for non-binding (or binding with lower affinity) in the absence of the lipocalin-fold ligand.

c) Mutation/deletion/insertion of residues for preventing dimerization or interaction with other proteins or lipid membranes (e.g., free cysteines, unprocessed signal peptide in ApoM, loop CD residues 59-68 in RBP4, etc.; see e.g. Skerra, Biochim Biophys Acta. 2000; 1482 (1-2):337-350; Zhang et al., Sci Rep. 2016; 6:30655; Redondo et al., FASEB J. 2008; 22 (4):1043-1054).

d) Mutation/deletion/insertion of residues for preventing post translational protein modification.

e) Engineering the lipocalin-fold molecule for improved stability, e.g., under reducing conditions in the cytoplasm as has been demonstrated for antibody fragments (Worn et al., J Biol Chem. 2000; 275(4):2795-2803). This can be achieved, for example, by rational design of stabilizing mutations or by directed evolution experiments which select for improved stability (Traxlmayr et al, Biochim Biophys Acta. 2012; 1824(4):542-549). However, also any other method for stabilization of proteins is possible.

The human intracellular iLBP protein family comprises a group of 6 retinoid binding proteins termed CRBPs and CRABPs, and the group of 10 fatty acid binding proteins (FABPs). Although iLBPs are intracellular proteins, some of them, e.g., FABP4 may have a function also in the extracellular space (Hotamisligil et al., Nat Rev Endocrinol. 2015; 11(10):592-605). All iLBPs have the same architecture with 10 anti-parallel β-strands connected by more or less elongated loops with the exception of an intervening helix-turn-helix motif between strands βA and βB (Lakshmi et al. PLoS One. 2015; 10 (8): e0135507; Zhang et al., PLoS One. 2012; 7 (5): e36772; Smathers et al., Hum Genomics. 2011; 5(3):170-191). Compared to LCNs their barrel structure is more compact and their ligands are hardly exposed to the solvent due to shielding by the helix-turn-helix motif at the entrance. However, like LCNs iLBPs have adapted to binding of a diverse spectrum of partially shared ligands and they also have in common the high tolerance to mutagenesis. The latter includes even the complete deletion of the helix-turn-helix motif at the barrel entrance and substitution by a simple loop (Curto et al., Protein Sci. 2009; 18 (4):735-746; Ogbay et al., Protein Sci. 2004; 13(5):1227-1237). Among the iLBPs, FABP1 and FABP6 are characterized by higher backbone flexibility and a larger ligand entrance, resulting in their unique capacity to accommodate bulky molecules and two of each. Binding of the so far tested ligands generally revealed only small conformational changes due to ligand induced rigidification (Yu et al., Sci Rep. 2016; 6:34171; Sharma et al., J Biol Chem. 2011; 286(36):31924-31928; Cai et al., Biophys J. 2012; 102(11):2585-2594; Franzoni et al., J Lipid Res. 2010; 51(6):1332-1343; Vaezeslami et al., J Mol Biol. 2006; 363(3):687-701; Gillilan et al., J Mol Biol. 2007; 372(5):1246-1260; Menozzi et al., J Struct Biol. 2017; 197(3):330-339; Long et al., Biophys J. 2010; 98(12):3054-3061). Obviously, these changes are sufficient to control interaction with other proteins and to mediate, e.g., nuclear transport and interaction with nuclear receptors, as well as, e.g., shuttling retinoids within the cell by mediating interaction with the receptor STRA6 in the cytoplasmic membrane in the case of CRBP-I (Gillilan et al., J Mol Biol. 2007; 372(5):1246-1260; Armstrong et al., J Biol Chem. 2014; 289(21):14941-14954; Amber-Vitos et al., PLoS One. 2015; 10 (8):e0132138; Berry et al., Mol Cell Biol. 2012; 32(15):3164-3175; Sessler et al., Mol Cell. 2005; 18(3):343-353; Hofer et al., J Biol Chem. 2015; 290(30):18438-18453; Furuhashi et al., Nat Rev Drug Discov. 2008; 7(6):489-503). Some iLBPs thereby interact via the formation/selection of a structural nuclear location signal (NLS) within the α2-helix at the entry of the calyx, which is elicited by some but not all of their small molecule ligands (Furuhashi et al., Nat Rev Drug Discov. 2008; 7(6):489-503).

Like with LCNs, the human variants of iLBPs are preferred for use in a LRPPI system if applied in humans in vivo. Among them the retinoid binding proteins, in particular the very well characterized CRABP-II (UniProt ID P29373), are preferred due to their retinoid ligand specificity (Zhang et al., PLoS One. 2012; 7 (5): e36772; Franzoni et al., J Lipid Res. 2010; 51(6):1332-1343; Vaezeslami et al., J Mol Biol. 2006; 363(3):687-701; Menozzi et al., J Struct Biol. 2017; 197(3):330-339). Furthermore, FABP2 (P12104), for which the helix-turn-helix substitution was exemplified, and FABP1 (P07148) due to their known low affinity to several clinically approved lipophilic drugs are also attractive iLBP members for engineering the binding pocket for recognition of clinically applicable ligands (Smathers et al., Hum Genomics. 2011; 5(3):170-191; Curto et al., Protein Sci. 2009; 18(4):735-746; Ogbay et al., Protein Sci. 2004; 13(5):1227-1237; Velkov T, Chem Biol. 2007; 14(4):453-465; Velkov T. PPAR Res. 2013; 2013:938401; Beringhelli T, PLoS One. 2015; 10 (7):e0132096; Chuang S, J Med Chem. 2008; 51(13):3755-3764).

For integration into the LRPPI system according to the present invention, fusion of the β-barrels of iLBPs to protein partners (with or without linker sequences), protein domains, peptides or single amino acids is possible via the N- and the C-terminal ends (of full length or trimmed iLBP proteins). The sequences are preferably modified for preventing unwanted interaction with their natural protein partners in the cytoplasm by modifying or deleting the respective interacting sequence elements (e.g., the helix-turn-helix motif containing the hidden structural NLS in the α2-helix and other interaction sites; Gillilan et al., J Mol Biol. 2007; 372(5):1246-1260; Armstrong et al., J Biol Chem. 2014; 289(21):14941-14954; Amber-Vitos et al., PLoS One. 2015; 10 (8):e0132138; Berry et al., Mol Cell Biol. 2012; 32(15): 3164-3175; Sessler et al., Mol Cell. 2005; 18(3):343-353). For increasing the affinity to selected lipocalin-fold ligands ("b") and/or for decreasing the affinity to their endogenous small molecule ligands, the iLBPs may be engineered similarly to LCNs. To facilitate the engineering of lipocalin-fold ligand dependent recognition, it is possible to substitute the helix-turn-helix motif by a loop sequence (as exemplified by Curto et al. and Ogbay et al. (Curto et al., Protein Sci. 2009; 18 (4):735-746; Ogbay et al., Protein Sci. 2004; 13(5):1227-1237).

The rationale of developing the LRPPI system according to the present invention (i.e. based on the "lipocalin-fold" of the lipocalin-fold molecule) is to maximize the freedom of choice in selecting the lipocalin-fold ligands ("b"). The crucial innovation for enabling this freedom is based on proteins of the superfamily of lipocalin proteins that contain the "lipocalin-fold" structure. Their key feature, i.e., the characteristic deep binding pocket with a calyx like shape and high structural flexibility is crucial for the flexibility and reliability of the present invention. As a consequence, these binding pockets can be engineered by relatively few mutations for binding to a broad range of small molecule ligands with diverse structural and biophysical characteristics. This has been exemplified with the proteins BBP and NGAL, which were engineered by substitution of 12 to 17 amino acid residues for high affinity binding to originally non-binding small molecules such as fluorescein, digoxigenin, digitoxigenin and a diamine-pentaacetic acid (DTPA) based chelator (Korndorfer et al., Proteins 2003; 53(1):121-129; Korndorfer et al., J Mol Biol. 2003; 330(2):385-396; Kim et al., J Am Chem Soc. 2009; 131(10):3565-3576). Thus, contrary to existing LRPPI systems, the novel system according to the present invention is defined by employing lipocalin-fold containing proteins (i.e., lipocalin-fold molecules) and neither by any definitive list of possible small molecules (i.e., lipocalin-fold ligands) nor by any specific structural and chemical properties of such molecules.

The lipocalin-fold ligand "b" according to the present invention is a "small molecule", e.g. "small" compared to polypeptides and proteins, such as the lipocalin-fold molecule. Accordingly, the lipocalin-fold ligand according to the present invention has a molecular weight of 1500 Da or less, preferably 1000 Da or less, especially 750 Da or less. It may be as small as, e.g. glycine (75 Da) or even below, provided that it allows a specific binding within the LRPPI system according to the present invention (i.e. binding to the lipocalin-fold molecule). Accordingly, preferred Mw ranges of the lipocalin-fold ligand of the present invention are 50 to 1500 Da, preferably 75 to 1500 Da, especially 150 to 750 Da. Preferably, the lipocalin-fold ligand can bind in the calyx of the lipocalin-fold molecule formed by the barrel and the loop regions of the lipocalin-fold structure. The lipocalin-fold ligand has a substantial and specific affinity to the lipocalin-fold molecule (in at least one conformation of the lipocalin-fold molecule) which may be 1 mM or lower, preferably 100 µM or lower, especially 10 µM or lower. Such affinity can be increased by directed evolution of the binding pocket of the lipocalin-fold molecules. Although up to 30 mutations or more may be applied to a given lipocalin-fold molecule (see, for example, Schonfeld et al., Proc Natl Acad Sci USA. 2009; 106(20):8198-8203), it is usually not necessary to exchange more than 25 or more than 20 to significantly increase the affinity to a given lipocalin-fold ligand (see, for example, Kim et al., J Am Chem Soc. 2009; 131(10):3565-3576; Korndorfer et al., Proteins 2003; 53(1): 121-129; Korndorfer et al., J Mol Biol. 2003; 330(2):385-396; Gebauer et al., J Mol Biol 2013; 425(4):780-802). Methods for generating lipocalin-fold molecules with an improved affinity towards the lipocalin-fold ligand are well available in the art (see above). Usually, only a few mutations are necessary for a significant increase in affinity towards a given lipocalin-fold ligand, for example only one, two or less, three or less, four or less, five or less, six or less, seven or less, eight or less, nine or less, or ten or less. The capability of a lipocalin-fold ligand "b" to induce a conformational alteration in the lipocalin-fold molecule "a" and/or to positively affect the affinity of a lipocalin-fold binding interaction partner "c" by direct interaction can be predicted to some extent using pharmacophores from existing small molecule ligands with such function. Additionally, this functional capability can be screened for by employing binding proteins, which have a conformation specific binding affinity for the lipocalin-fold molecule (detailed in Example 2, below, and in Coward et al. Anal Biochem. 2009; 384 (2):312-320, Sharif et al., Anal Biochem. 2009; 392 (2):162-168 and Dobri et al., Invest Ophthalmol Vis Sci. 2013; 54(1):85-95). In the case of RBP4, e.g., TTR can be used as a naturally occurring conformation specific binding protein. If there is no such protein available, as for example for TLC or ApoM, which have also been reported to undergo lipocalin-fold ligand dependent conformational switching (Gasymov et al., Biochim Biophys Acta. 1998; 1386(1):145-156; Breustedt et al., Acta Crystallogr D Biol Crystallogr. 2009; 65 (Pt 10):1118-1125; Zhang et al., Sci Rep. 2016; 6:30655; Christoffersen et al., Proc Natl Acad Sci USA. 2011; 108 (23):9613-9618), then it is possible to first generate a protein-based binder that interacts with the unloaded lipocalin-fold molecule, i.e. in the absence of lipocalin-fold ligands, by a process of alternating selection for binding to the lipocalin-fold molecule in the absence and nonbinding (or binding with reduced affinity) in the presence of lipocalin-fold ligands known to shift conformational states of the lipocalin-fold molecule. This alternating selection strategy ensures that a binder is selected, which specifically recognizes the unloaded (i.e. not loaded with any lipocalin-fold ligand) state of the lipocalin-fold molecule. In Example 1 we exemplified this process of alternating screening in presence and absence of a lipocalin-fold ligand (A1120) in opposite direction for selecting a lipocalin-fold binding interaction partner, i.e., a protein that binds RBP4 (i.e. the lipocalin-fold molecule) with increased affinity in presence of the lipocalin-fold ligand A1120.

Typically, the process of selecting lipocalin-fold ligand molecules can start from:
1. any given molecule with or without initial binding affinity
2. any existing compound libraries for high throughput screening for binding affinity and/or function
3. any structural databases of compounds that can be used in virtual screening for binding and/or function Ad 1: Initial binding affinity is not required in this approach, since the binding pocket of the lipocalin-fold molecule can be engineered for binding (see e.g. DE 19742706 A1). The feasibility of engineering of lipocalin-fold molecules for high affinity binding to arbitrary, initially non-binding, molecules has been exemplified by engineering of BBP and NGAL for binding of fluorescein, digoxigenin and a DTPA-based chelator (Korndorfer et al., Proteins 2003; 53(1):121-129; Korndorfer et al., J Mol Biol. 2003; 330(2):385-396; Kim et al., J Am Chem Soc. 2009; 131(10):3565-3576). Hence, clinically attractive lipocalin-fold ligand "b" candidates can be selected regardless of initial binding affinity, just considering pharmacological properties as, e.g., tolerability, bioavailability, plasma levels, pharmacokinetics, tissue penetrance etc. Such molecules could be, for example, Indicaxanthin and Vulgaxanthin, which are pharmacologically well investigated and tolerated and are contained in sufficiently high amounts in a narrow segment of edible plants. There are, however, numerous examples of clinically approved drugs which have already been demonstrated to bind to certain lipocalin-fold molecules (e.g., human FABP1; Smathers et al., Hum Genomics. 2011; 5(3):170-191; Velkov et al., Chem Biol. 2007; 14(4):453-465; Velkov T., PPAR Res. 2013; 2013:938401; Beringhelli et al., PLoS One. 2015; 10 (7):e0132096; Chuang at al., J Med Chem. 2008; 51(13):3755-3764). Of course, such molecules are attractive starting points. The most attractive molecules are non-natural ligands, for which conformational effects have been proven and which have clinical application potential. For RBP4, for example, these ligands are A1120 and numerous derivatives as well as synthetic retinoids such as, e.g., fenretinide, N-Ethylretinamide, all-trans retinoic acid, retinyl acetate and axerophthene (Berni et al., FEBS Lett. 1992; 308(1):43-45; Zanotti et al., J Biol Chem. 1993; 268 (33):24873-24879; Zanotti et al., J Biol Chem. 1994; 269(47):29613-29620; Motani et al., J Biol Chem. 2009; 284(12):7673-7680; Cioffi et al., J Med Chem. 2014; 57(18):7731-7757; Cioffi et al., J Med Chem. 2015; 58(15):5863-5888).

Ad 2: High throughput screening of molecule libraries for molecules with binding affinity can be performed by various assays (reviewed in Auld et al., Receptor Binding Assays for HTS and Drug Discovery. In: Sittampalam et al., eds. Assay Guidance Manual. Bethesda MD: Eli Lilly & Company and the National Center for Advancing Translational Sciences; 2004). Screening of molecule libraries was, e.g., employed for identifying A1120 as a high affinity ligand for RBP4 (Motani et al., J Biol Chem. 2009; 284(12):7673-7680). A consequence of this strategy is that the identified lipocalin-fold ligands display already some binding affinity and thus can be further assayed for mediating ligand-dependent binding or dissociation of a binder "c" without requirement of prior binding pocket engineering of the lipocalin-fold molecule. Of note, there are possibilities that enable high throughput screening for binding and function, like inducing conformational switching, in a single step. In the case of RBP4 this could be done, for example, by FRET based assays for detecting the conformation dependent interaction with TTR (Coward et al., Anal Biochem. 2009; 384(2):312-320; Sharif et al., Anal Biochem. 2009; 392(2):162-168; Dobri et al., Invest Ophthalmol Vis Sci. 2013; 54(1):85-95)). If desired, the affinity of the respective lipocalin-fold ligand to the lipocalin-fold molecule can be further increased by engineering (i.e. mutagenesis) of the binding pocket of the lipocalin-fold molecule.

Ad 3: Virtual screening of compound databases is attractive when there are known small molecule ligands, which mediate conformational alterations in a lipocalin-fold molecule. Then a modeled pharmacophore of the small molecule can be used to screen for molecules, which might similarly interact with the lipocalin-fold molecule and thereby show similar function (see Qing et al., Journal of Receptor, Ligand and Channel Research 2014; 7:81-92 for a review on virtual screening using pharmacophore modeling). In the optimal case, the crystal structure of the lipocalin-fold molecule charged with the modeled small molecule ligand is also known, since this helps to improve the accuracy of the prediction algorithms. There are several examples of known structures for lipocalin-fold molecules bound to a small molecule ligand (Berni et al., FEBS Lett. 1992; 308(1):43-45; Zanotti et al., J Biol Chem. 1993; 268 (33):24873-24879; Zanotti et al., J Biol Chem. 1994; 269(47):29613-29620; Pattanayek et al., Protein Sci. 1999; 8(10):2027-2032; Motani et al., J Biol Chem. 2009; 284(12):7673-7680; Gasymov et al., Biochim Biophys Acta. 1998; 1386(1):145-156; Breustedt et al., Acta Crystallogr D Biol Crystallogr. 2009; 65 (Pt 10):1118-1125; Gasymov et al., Biochemistry. 2012; 51(14):2991-3002; Zhang et al., Sci Rep. 2016; 6:30655; Christoffersen et al., Proc Natl Acad Sci USA. 2011; 108 (23):9613-9618; Coward et al., Anal Biochem. 2009; 384 (2):312-320). This strategy is exemplified in the example section below with RBP4 charged with A1120, for which a pharmacophore model was generated in order to identify and prioritize molecules for functional testing and for engineering of the binding pocket of RBP4 (described in Example 2, below). Importantly, the pharmacophore approach does not deliver a final complete list of potentially conformation inducing molecules due to limitations of pharmacophore methods (reviewed in Qing et al., Journal of Receptor, Ligand and Channel Research 2014; 7:81-92) and due to incomplete and not updated databases etc. Moreover, there are other molecules also known to alter the conformation of RBP4, e.g., fenretinide, for which a pharmacophore based approach would lead to identification of yet another set of molecules in the chemical space. In fact, in preferred embodiments, in silico filtering of millions of molecules for function together with directed evolution of the highly flexible binding pocket of the lipocalin-fold structure in the lipocalin-fold molecules according to the present invention is a perfect combination and a crucial strength of the novel LRPPI system. Of note, virtual screening also enables identifying functional molecules, which do not have sufficient initial binding affinity, which is not a problem, since affinity can easily be generated by engineering of the lipocalin-fold molecule. In this case, lipocalin-fold molecule mutants are selected by use of a conformation specific binding protein that binds to the lipocalin-fold molecule mutatants in the absence but not in the presence of a known conformation inducing ligand. Thus, the dissociation of this conformation specific binding protein enables the identification of lipocalin-fold ligand candidates that bind to the lipocalin-fold molecule and that at the same time induce conformational alterations (detailed in Example 2, below).

Principally, the lipocalin-fold binding interaction partner "c" can be provided or engineered based on any available molecular binder scaffold including antibodies, antibody fragments [e.g. single-chain variable fragments (scFv), antigen binding fragments (Fabs), nanobodies, among others] and non-antibody based scaffolds such as affibodies, a further (or the same) lipocalin-fold molecule, preferably LCNs, especially anticalins; avimers, DARPins, fynomers, Kunitz domains, knottins, monobodies, binders based on Sso7d, reduced charge Sso7d (rcSso7d) or Sac7d, among many others (Simeon et al., Protein Cell. 2017; Gilbreth et al., Curr Opin Struct Biol. 2012; 22(4):413-420; Koide et al., ACS Chem Biol. 2009; 4(5):325-334; Traxlmayr et al., J Biol Chem. 2016; 291(43):22496-22508). Meanwhile, many more non-antibody binding proteins have been reported (Pluckthun, Alternative Scaffolds: Expanding the options of antibodies. In: Little M, ed. New York: Cambridge University Press; 2009:244-271; Chapman et al., Cell Chem Biol. 2016; 23(5):543-553; Binz et al., Nat Biotechnol. 2005; 23(10):1257-1268; Vazquez-Lombardi et al., Drug Discov Today. 2015; 20(10):1271-1283), and, in fact, synthetic library design and selection can be applied to any protein which then can potentially serve as lipocalin-fold binding interaction partner "c", too (Plückthun, Alternative Scaffolds: Expanding the options of antibodies. In: Little M, ed. New York: Cambridge University Press; 2009:244-271). With the aim of clinical applicability of the LRPPI systems according to the present invention, lipocalin-fold binding interaction partners "c" are preferably derived from small human single protein domains (e.g., fibronectin type III domain (FN3) based Monobodies) with a minimized number of mutated amino acids for keeping immunogenicity as low as possible. It is of course also possible to attach such further molecules and scaffolds to the lipocalin-fold molecule (or to a lipocalin-fold binding interaction partner).

Accordingly, the lipocalin-fold molecule according to the present invention may be any protein that contains the structural motif of a lipocalin-fold to which (or in which) the lipocalin-fold ligand binds and which enables binding of the lipocalin-fold molecule to the lipocalin-fold binding interaction partner. Usually, the lipocalin-fold molecule according to the present invention is adapted to the specific needs for the lipocalin-fold molecule "a"/lipocalin-fold ligand "b"/lipocalin-fold binding interaction partner "c" triangle by providing a "starting" lipocalin-fold molecule which may already have a certain affinity to a given lipocalin-fold ligand and/or for which clinically attractive ligands with functional activity could be identified by virtual screening. This starting lipocalin-fold molecule may then be engineered by one or more amino acid exchanges, insertions and/or deletions to optimize lipocalin-fold ligand binding, and in the case of strategy B of the lipocalin-fold based LRPPI system also for binding to a lipocalin-fold binding interaction partner "c". In strategy A the lipocalin-fold binding interaction partner "c" is generated by engineering of a protein (that is originally not able to bind to any naturally occurring lipocalin-fold molecule with an affinity of <10 µM in the presence of any lipocalin-fold ligand) for binding to the (starting and/or engineered) lipocalin-fold molecule (bound to the lipocalin-fold ligand). Such sequence optimization of a protein for generating a lipocalin-fold ligand dependent lipocalin-fold binding interaction partner is shown in the example section of the present invention and well available for a person skilled in the art with the disclosure contained herein. In fact, it is established in the art of protein engineering that protein scaffolds (especially well-established scaffolds, such as antibodies and non-antibody-based scaffolds, especially lipocalins) can be adapted so that virtually any biological molecules (especially proteins) can be bound (see e.g. (for non-antibody scaffolds) Vasquez-Lombardi et al., Drug Discov. Today 20 (2015), 1271-1283; Plückthun, Alternative Scaffolds: Expanding the Options of Antibodies. In: Recombinant Antibodies for Immunotherapy, Melvyn Little, Cambridge University Press, New York (2009), pp. 244-271).

The (starting) lipocalin-fold molecule therefore preferably contains the structural lipocalin-fold of a naturally occurring protein of the lipocalin-fold superfamily (for clinical applications in human patients: preferably a naturally occurring human lipocalin-fold molecule) or a known variant thereof (e.g. an "anticalin" or "mutein of lipocalin" and the like; a vast number of such variants have already been disclosed in the prior art). The lipocalin-fold molecule to be used in the LRPPI system according to the present invention may then be adapted to the specificities of the lipocalin-fold ligand/lipocalin-fold binding interaction partner by the introduction of modifications, as disclosed above (e.g. a) to e)), by engineering (i.e. amino acid changes, insertions and/or deletions) of the binding pocket, amino acid positions in the β-barrel structure, and/or amino acid positions in the regions adjoining the β-strands of the β-barrel structure, mutation/deletion/insertion of residues for preventing dimerization or interaction with other molecules or for preventing post-translational protein modification and/or engineering of the lipocalin-fold for improved stability.

As already stated above, the lipocalin-fold architecture is very robust and has high sequence flexibility, as demonstrated by the fact that it has not been possible to define any sequence motif that is common to all naturally occurring members of the lipocalin superfamily, including LCNs and iLBPs (Lakshmi et al. PLoS One. 2015; 10 (8): e0135507; Flower et al., Biochim Biophys Acta. 2000; 1482 (1-2):9-24). Apart from the generally high sequence variation in naturally occurring members of the lipocalin superfamily, the regions adjoining the structurally conserved β-strands not only show high variation in sequence, but also in structure (Flower et al., Biochim Biophys Acta. 2000; 1482 (1-2):9-24; Schiefner et al., Acc Chem Res. 2015; 48 (4): 976-985). Given the extensive sequence variation among naturally occurring lipocalin superfamily members and/or structural variation in the regions adjoining the β-strands, it is not surprising that in the past lipocalin molecules have been successfully engineered by mutating more than 30 amino acid positions, corresponding to more than 15% of all amino acid positions in the respective protein, without any major structural changes in the structurally conserved β-strands of the characteristic β-barrel structure (Schonfeld et al., Proc Natl Acad Sci USA. 2009; 106(20):8198-8203). Thus, it is well-established in the field that lipocalin-fold molecules can be extensively mutated without impairing the overall β-barrel fold (i.e. particularly the loop regions but also the β-strands of the β-barrel can be designed by exchanging, inserting and/or deleting a considerable number of amino acids). Therefore, in the present invention, which describes the usage of the lipocalin-fold structure in LRPPI systems, a lipocalin-fold molecule is defined as any naturally occurring molecule classified into the lipocalin superfamily in the SCOP database (version 1.75), or a mutant thereof. However, it is preferred to exchange only a limited number of amino acids. The LRPPI system according to the present invention therefore preferably comprises (1) a lipocalin-fold molecule being identical to a naturally occurring member of the lipocalin superfamily or (2) an already existing variant thereof (e.g. an already existing anticalin, lipocalin mutein, iLBP with complete deletion of the helix-turn-helix motif at the barrel entrance etc.) or (3) a derivative of (1) or (2) with at least 70%, preferably at least 80%, especially at least 90% sequence identity to its counterpart that it derives from.

According to a preferred embodiment, the lipocalin-fold molecule is a derivative of a naturally occurring or otherwise disclosed (by its amino acid sequence) lipocalin-fold molecule with at least 70%, preferably at least 80%, especially at least 90% sequence identity in the β-barrel structure, whereby this β-barrel structure is defined as the regions which correspond structurally to amino acid positions 21-30, 41-47, 52-58, 71-78, 85-88, 102-109, 114-120 and 132-138 in human RBP4 (according to the amino acid residue numbering scheme in the PDB entry 1RBP); or to the amino acid positions 14-23, 37-43, 48-54, 62-69, 76-79, 84-91, 96-102 and 111-117 in human tear lipocalin (TLC; as defined by Schiefner et al., Acc Chem Res. 2015; 48(4):976-985); or to the amino acid positions 44-53, 69-75, 81-87, 96-103, 110-113, 119-126, 131-137 and 142-148 in human apolipoprotein M (ApoM; as defined by Schiefner et al., Acc Chem Res. 2015; 48(4):976-985); or to the amino acid positions 5-12, 41-45, 50-54, 61-65, 71-73, 81-87, 93-96, 108-112, 119-124 and 129-135 in human cellular retinoic acid binding protein II (CRABPII; according to the amino acid residue numbering scheme in PDB entry 2FS6); or to the amino acid positions 5-12, 39-43, 48-52, 59-63, 69-71, 79-85, 91-94, 99-103, 109-114 and 119-125 in human fatty acid binding protein 1 (FABP1; according to the amino acid residue numbering scheme in PDB entry 2F73).

Preferred embodiments of the lipocalin-fold molecule according to the present invention also include lipocalin-fold molecules which comprise 1-30 amino acid exchanges and/or 1-50 amino acid deletions and/or 1-50 amino acid insertions of (1), (2) or (3) which (at least) contain the lipocalin-fold and are able to bind to the lipocalin-fold ligand and the lipocalin-fold binding interaction partner. Accordingly, the ligand regulated protein-protein interaction system preferably comprises as lipocalin-fold molecule a molecule identical with a naturally occurring iLBP (intracellular lipid binding protein), a naturally occurring lipocalin or an anticalin, and derivatives of any of these molecules with 1-30 amino acid exchanges and/or 1-50 amino acid deletions and/or 1-50 amino acid insertions.

Alternatively, the LRPPI system according to the present invention may also comprise a (4) fragment of (1) or (2) or (3) with a length of at least 80, preferably at least 100, especially at least 120, amino acids in the case of LCNs [or with a length of at least 80, preferably at least 85, especially at least 90, amino acids in the case of iLBPs (which are generally smaller proteins than LCNs)] covering at least the structurally conserved β-barrel structure of the lipocalin-fold. This structurally conserved β-barrel structure comprises or consists of amino acid positions which correspond structurally to the amino acid positions 21-30, 41-47, 52-58, 71-78, 85-88, 102-109, 114-120 and 132-138 in human RBP4 (according to the amino acid residue numbering scheme in the PDB entry 1RBP); or to the amino acid positions 14-23, 37-43, 48-54, 62-69, 76-79, 84-91, 96-102 and 111-117 in human tear lipocalin (TLC; as defined by Schiefner et al., Acc Chem Res. 2015; 48 (4):976-985); or to the amino acid positions 44-53, 69-75, 81-87, 96-103, 110-113, 119-126, 131-137 and 142-148 in human apolipoprotein M (ApoM; as defined by Schiefner et al., Acc Chem Res. 2015; 48 (4):976-985); or to the amino acid positions 5-12, 41-45, 50-54, 61-65, 71-73, 81-87, 93-96, 108-112, 119-124 and 129-135 in human cellular retinoic acid binding protein II (CRABPII; according to the amino acid residue numbering scheme in PDB entry 2FS6); or to the amino acid positions 5-12, 39-43, 48-52, 59-63, 69-71, 79-85, 91-94, 99-103, 109-114 and 119-125 in human fatty acid binding protein 1 (FABP1; according to the amino acid residue numbering scheme in PDB entry 2F73).

Further preferred lipocalin-fold molecules in the LRPPI system according to the present invention are derivatives of a naturally occurring lipocalin or iLBP with up to 15, up to 30, or up to 50 amino acid deletions and/or up to 15, up to 30, or up to 50 amino acid insertions outside of the structurally conserved β-barrel structure. Outside the structurally conserved β-barrel structure these molecules are very flexible to amino acid changes and therefore combinations of mutations, deletions and insertions are possible in these regions which correspond structurally to amino acid residues 1-20, 31-40, 48-51, 59-70, 79-84, 89-101, 110-113, 121-131 and 139-183 in human RBP4 (according to the amino acid residue numbering scheme in the PDB entry 1RBP), which define the regions adjoining the structurally conserved β-strands in human RBP4; or corresponding structurally to the regions of amino acid residues 1-13, 24-36, 44-47, 55-61, 70-75, 80-83, 92-95, 103-110 and 118-158 in human TLC (according to the amino acid residue numbering scheme in Schiefner et al., Acc Chem Res. 2015; 48 (4):976-985), which define the regions adjoining the structurally conserved β-strands in human TLC; or corresponding structurally to the regions of amino acid residues 1-43, 54-68, 76-80, 88-95, 104-109, 114-118, 127-130, 138-141 and 149-188 in human ApoM (according to the amino acid residue numbering scheme in Schiefner et al., Acc Chem Res. 2015; 48 (4):976-985), which define the regions adjoining the structurally conserved β-strands in human ApoM; or corresponding structurally to the regions of amino acid residues 1-4, 13-40, 46-49, 55-60, 66-70, 74-80, 88-92, 97-107, 113-118, 125-128 and 136-137 in human CRABPII (according to the amino acid residue numbering scheme in PDB entry 2FS6), which define the regions adjoining the structurally conserved β-strands in human CRABPII; or corresponding structurally to the regions of amino acid residues 1-4, 13-38, 44-47, 53-58, 64-68, 72-78, 86-90, 95-98, 104-108, 115-118 and 126-127 in human FABP1 (according to the amino acid residue numbering scheme in PDB entry 2F73), which define the regions adjoining the structurally conserved β-strands in human FABP1.

In a preferred embodiment, the LRPPI system according to the present invention comprises as lipocalin-fold molecule a derivative of a naturally occurring member of the lipocalin superfamily with at least one, two, three, four, five, six, seven, eight, nine, ten, eleven, twelve, 13, 14, 15, 16, 17, 18, 19, 20, 21, 22, 23, 24, 25, 26, 27, 28, 29, or 30 amino acid exchanges.

According to a further preferred embodiment, the lipocalin-fold molecule used in the LRPPI system according to the present invention is a lipocalin, i.e., a protein containing an eight-stranded up-and-down β-barrel arranged in a +1 topology, followed by an α-helix after the C-terminal end of the eighth β-strand, or a derivative of a lipocalin with 1-30 amino acid exchanges and/or 1-50 amino acid deletions and/or 1-50 amino acid insertions.

In designing the lipocalin-fold molecule according to the present invention, one parameter which may be significantly improved in the derivatization/mutation process from a starting lipocalin-fold molecule to a molecule actually optimized for a given LRPPI system, is affinity to the lipocalin-fold ligand "b". Additionally or alternatively, in the case in which the lipocalin-fold molecule itself is engineered as a binder instead of the lipocalin-fold binding interaction partner, the parameter to improve is increasing the affinity difference between the two statuses of the lipocalin-fold molecule (bound or not bound to the lipocalin-fold ligand) for binding to the lipocalin-fold binding interaction partner "c". Selection of lipocalin-fold molecule/lipocalin-fold ligand pairs that are preferentially characterized by structural differences between the bound and unbound statuses (preferably resulting from conformational alterations) is the basis for maximum affinity differences of the two lipocalin-fold molecule statuses for a lipocalin-fold binding interaction partner "c". In the case, in which the lipocalin-fold molecule is used as an antigen (i.e. strategy A of the lipocalin-fold based LRPPI system), the lipocalin-fold binding interaction partner "c" can be subsequently engineered for maximum selectivity between the two statuses of the lipocalin-fold molecule, i.e., maximum affinity difference. The engineering of the lipocalin-fold binding interaction partner and/or the lipocalin-fold molecule leads to LRPPI systems wherein the affinity of the lipocalin-fold binding interaction partner to the lipocalin-fold molecule in the lipocalin-fold ligand-bound state is at least 10-fold higher, preferably at least 20-fold higher, especially at least 50-fold higher than the affinity of the lipocalin-fold binding interaction partner to the lipocalin-fold molecule in the unbound state (i.e. in the absence of the lipocalin-fold ligand). In the course of the present invention, the human lipocalin RBP4, which is known to undergo conformational alteration upon binding of some ligands, has been investigated in more detail to prove the concept of the present invention in principle. Similarly to RBP4, the human lipocalins TLC and ApoM are also known to undergo significant ligand induced conformational alterations and it is thus preferred to use one of these three lipocalins as lipocalin-fold molecule or as starting lipocalin-fold molecule for the generation of a LRPPI system according to the present invention.

A preferred embodiment of the LRPPI system according to the present invention therefore applies a lipocalin-fold molecule that has a sequence identity with the native versions of human RBP4, TLC or ApoM of at least 70%, preferably at least 80%, especially at least 90%.

According to a preferred embodiment, the lipocalin-fold molecule according to the present invention has a sequence identity with human RBP4 of at least 70%, preferably of at least 80%, especially of at least 90% in the structurally conserved β-barrel structure including the regions of amino acid residues 21-30, 41-47, 52-58, 71-78, 85-88, 102-109, 114-120 and 132-138 according to the amino acid residue numbering scheme in the PDB entry 1RBP, or a fragment thereof with at least 80, preferably at least 100, especially at least 120 amino acid residues and comprising the regions corresponding to amino acid residues 21-30, 41-47, 52-58, 71-78, 85-88, 102-109, 114-120 and 132-138 of human RBP4 (according to the amino acid residue numbering scheme in the PDB entry 1RBP); or (2) the lipocalin-fold molecule has a sequence identity with human tear lipocalin (TLC) of at least 70%, preferably of at least 80%, especially of at least 90% in the structurally conserved β-barrel structure including the regions of amino acid residues 14-23, 37-43, 48-54, 62-69, 76-79, 84-91, 96-102 and 111-117 in human TLC as defined by Schiefner et al., Acc Chem Res. 2015; 48 (4):976-985, or a fragment thereof with at least 80, preferably at least 100, especially at least 120 amino acid residues and comprising the regions corresponding to amino acid residues 14-23, 37-43, 48-54, 62-69, 76-79, 84-91, 96-102 and 111-117 of human TLC; or (3) the lipocalin-fold molecule has a sequence identity with human apolipoprotein M (ApoM) of at least 70%, preferably of at least 80%, especially of at least 90% in the structurally conserved β-barrel structure including the regions of amino acid residues 44-53, 69-75, 81-87, 96-103, 110-113, 119-126, 131-137 and 142-148 in human ApoM as defined by Schiefner et al., Acc Chem Res. 2015; 48(4):976-985, or a fragment thereof with at least 80, preferably at least 100, especially at least 120 amino acid residues and comprising the regions corresponding to amino acid residues 44-53, 69-75, 81-87, 96-103, 110-113, 119-126, 131-137 and 142-148 of human ApoM.

In a preferred embodiment, the lipocalin-fold molecule of the LRPPI system according to the present invention has a sequence identity with human RBP4 of at least 95%, or a sequence identity with human tear lipocalin (TLC) of at least 95%, or a sequence identity with human apolipoprotein M (ApoM) of at least 95%.

The LRPPI system according to the present invention consists of the central lipocalin-fold molecule "a"/lipocalin-fold ligand "b"/lipocalin-fold binding interaction partner "c" triangle (see FIG. 1A). However, this triangle can be further functionalized by linking further moieties to the lipocalin-fold molecule "a" and/or the lipocalin-fold binding interaction partner "c" (see e.g. FIG. 1B). The LRPPI triangle according to the present invention can therefore be expanded into various architectures, e.g. as CARs (as disclosed below). Again, it may be emphasised that the "triangles" according to the present invention differ from any naturally occurring (physiological) triangle, because the lipocalin-fold binding interaction partner (or any domain of it that mediates binding to the lipocalin-fold molecule) is not a naturally occurring lipocalin-fold binding interaction partner (i.e. a protein which has an affinity of <10 µM to any naturally occurring lipocalin-fold molecule in the presence of any lipocalin-fold ligand). Preferably, the lipocalin-fold binding interaction partner is also not derived from a naturally occurring lipocalin-fold binding interaction partner. "Being derived from" is defined as containing at least one segment of at least 50 consecutive amino acids with an amino acid sequence that is at least 98% identical with the amino acid sequence of any segment of that naturally occurring protein and which has an affinity of <10 µM to any naturally occurring lipocalin-fold molecule (in the presence of any lipocalin-fold ligand). Preferably both the lipocalin-fold molecule and the lipocalin-fold binding interaction partner are not naturally occurring molecules but artificially designed molecules (e.g. designed by recombinant technology and/or directed evolution). In a preferred embodiment, the lipocalin-fold binding interaction partner is or comprises a lipocalin-fold molecule and/or the lipocalin-fold binding interaction partner comprises an antigen, a cell surface receptor, an antibody, etc.

For the LRPPI system according to the present invention, it is also preferred that the affinity of the lipocalin-fold ligand to the lipocalin-fold molecule is in a range that allows binding of the lipocalin-fold ligand to the lipocalin-fold molecule at lipocalin-fold ligand concentrations that can be achieved in the physiological environment in the human body. Accordingly, it is preferred that the lipocalin-fold ligand has an affinity to the lipocalin-fold molecule of below 1 mM, preferably of below 100 µM, especially of below 10 µM. This affinity between the lipocalin-fold ligand and the lipocalin-fold molecule is defined as a $K_d$ (dissociation constant) value and preferably determined by isothermal titration calorimetry (ITC) using an automated MicroCal PEAQ-ITC instrument (Malvern Instruments).

The LRPPI system according to the present invention generally relies on a substantial difference in the affinities of the lipocalin-fold molecule "a" to the lipocalin-fold binding interaction partner "c" depending on whether the lipocalin-fold ligand "b" is bound or not. It is also preferred that this affinity window (i.e. the affinities of the lipocalin-fold binding interaction partner to the lipocalin-fold molecule bound or not bound to the lipocalin-fold ligand, respectively) is present in a reasonable affinity range which allows for regulation of this LRPPI system under physiological conditions. Therefore, it is preferred that the affinity of the lipocalin-fold binding interaction partner to the lipocalin-fold molecule in the ligand-bound state is below 10 µM, preferably below 2 µM, especially below 400 nM. This affinity between the lipocalin-fold binding interaction partner and the lipocalin-fold molecule in the ligand-bound state is defined as a $K_d$ value and preferably determined by surface plasmon resonance (SPR) using a BiacoreT200 instrument (GE healthcare).

For the LRPPI system according to the present invention, the affinity difference of the lipocalin-fold molecule binding to the lipocalin-fold binding interaction partner between the states bound/unbound to the lipocalin-fold ligand should be as high as possible. This can be achieved by directed evolution of the interaction partner and screening for suitable affinity differences (for increased affinity differences). For being applicable in an in vivo environment, the lipocalin-fold molecule has to have a sufficiently high affinity to the lipocalin-fold ligand. This enables functioning of the LRPPI system according to the present invention also in a patient in vivo. Here, it has also to be considered that drug concentrations in plasma (e.g. for the lipocalin-fold ligand) is usually a few µM. Accordingly, the affinity of the lipocalin-fold ligand to the lipocalin-fold molecule has to be sufficiently high that such plasma concentrations can achieve appropriate binding of the ligand to the lipocalin-fold molecule. Moreover, the LRPPI system according to the present invention should be designed to minimize relevant binding of other substances to the lipocalin-fold molecules (which could elicit adverse reactions or hinder effectiveness of in vivo functioning of the system (e.g. by competing with binding to the lipocalin-fold molecule)).

The lipocalin-fold based LRPPI system enables the highest flexibility with respect to choosing the lipocalin-fold ligand used for controlling PPI. Whereas certain embodiments of the present invention work with substances already known to have a certain affinity to (certain) lipocalin-fold molecule(s), also the lipocalin-fold molecule may be designed to bind a small molecule of interest, thereby enabling the small molecule to become a lipocalin-fold ligand by such engineering of a lipocalin-fold molecule. Accordingly, any interesting small molecule, interesting for pharmaceutical purposes and thus preferred to be used as a lipocalin-fold ligand "b" according to the present invention (i.e. a substance enabling the binding of the lipocalin-fold molecule to the lipocalin-fold binding interaction partner) can be included in a LRPPI system according to the present invention. According to a preferred embodiment of the present invention, the lipocalin-fold ligand is fenretinide (PubChem CID: 5288209), N-Ethylretinamide (PubChem CID: 5288173), all-trans retinoic acid (PubChem CID: 444795), axerophthene (PubChem CID: 5287722), A1120 (PubChem CID 25138295), derivatives of A1120 (Cioffi et al., J Med Chem. 2014; 57(18):7731-7757; Cioffi et al., J Med Chem. 2015; 58(15):5863-5888)), 1,4-butanediol (Pubchem CID: 8064), sphingosine-1-phosphate (Pubchem CID: 5283560), tetradecanoic acid (Pubchem CID: 11005), indicaxanthin (Pubchem CID: 6096870 and 12310796), vulgaxanthin I (Pubchem CID: 5281217), Montelukast (Pubchem CID: 5281040), Cyclandelate (Pubchem CID: 2893), Oxolamine (Pubchem CID: 13738), Mazaticol (Pubchem-CID: 4019), Butoctamid (Pubchem CID: 65780), Tonabersat (Pubchem CID: 6918324), Novazin (Pubchem CID: 65734), Diphenidol (Pubchem CID: 3055), Neobornyval, Erlotinib (Pubchem CID: 92131336), Tanespimycin (Pubchem CID: 6505803), LMI070 (Pubchem CID: 85471316), Alloclamide (Pubchem CID: 71837), Diacetolol (Pubchem CID: 50894), Acotiamide (Pubchem CID: 5282338), Acoziborole (Pubchem CID: 44178354), Acumapimod (Pubchem CID: 11338127), Apalutamide (Pubchem CID: 24872560), ASP3026 (Pubchem CID: 25134326), AZD1480 (Pubchem CID: 16659841), BIIB021 (Pubchem CID: 16736529), Branaplam (Pubchem CID: 89971189), Brequinar (Pubchem CID: 57030), Chlorproguanil (Pubchem CID: 9571037), Clindamycin (Pubchem CID: 446598), Emricasan (Pubchem CID: 12000240), Enasidenib (Pubchem CID: 89683805), Enolicam (Pubchem CID: 54679203), Flurazepam (Pubchem CID: 3393), ILX-295501 (Pubchem CID: 127737), Indibulin (Pubchem CID: 2929), Metoclopramide (Pubchem CID: 12598248), Mevastatin (Pubchem CID: 64715), MGGBYMDAPCCKCT-UHFFFAOYSA-N (Pubchem CID: 25134326, having the structure_2-N-[2-methoxy-4-[4-(4-methylpiperazin-1-yl)piperidin-1-yl]phenyl]-4-N-(2-propan-2-ylsulfonylphenyl)-1,3,5-triazine-2,4-diamine), MK0686 (Pubchem CID: 16102897), Navarixin (Pubchem CID: 71587743), Nefazodone hydrochloride (Pubchem CID: 54911), Pantoprazole (Pubchem CID: 4679), Pavinetant (Pubchem CID: 23649245), Proxazole (Pubchem CID: 8590),Siccanin (Pubchem CID: 71902), Sulfaguanole (Pubchem CID: 9571041), Sunitinib (Pubchem CID: 5329102), Suvorexant (Pubchem CID: 24965990), Tiapride (Pubchem CID: 5467), Tonabersat (Pubchem CID: 6918324), VNBRGSXVFBYQNN-UHFFFAOYSA-N(Pubchem CID: 24794418, having the structure N-[4-(2-amino-3-chloropyridin-4-yl)oxy-3-fluorophenyl]-4-ethoxy-1-(4-fluorophenyl)-2-oxopyridine-3-carboxamide), YUHNXUAATAMVKD-PZJWPPBQSA-N(Pubchem CID: 44548240, having the structure [(1R)-2-[(3S)-3-[[5-chloro-2-(tetrazol-1-yl)phenyl]methylcarbamoyl]-3,4-dihydropyrazol-2-yl]-1-(4-fluorophenyl)-2-oxoethyl] propanoate), Ulimorelin (Pubchem CID: 11526696), Xipamide (Pubchem CID: 26618), Tropesin (Pubchem CID: 47530), Triclabendazole (Pubchem CID: 50248), Triclabendazole sulfoxide (Pubchem CID: 127657), Triclabendazole sulfone (Pubchem CID: 10340439) and Trametinib (Pubchem CID: 11707110) etc. Preferred substances are also provided in Table 1, below.

An unmet need in the field of cellular immunotherapy is the reversible control of CAR function by clinically applicable small molecules. Thus, in a preferred application the LRPPI system of the present invention is integrated into a CAR which is expressed in T cells or other effector cells such as, e.g., NK cells. The preferred version of the LRPPI system for controlling CAR function is where the lipocalin-fold ligand ("b")-loaded lipocalin-fold molecule "a" is used as antigen for a binder "c" (see schematic representation in FIGS. 2A and B). In this version, the CAR construct that mediates binding to the target cell is separated from the CAR construct that mediates signal transduction, whereby the CAR construct that mediates binding to the target cell can be secreted by the effector cell or can be administered/added exogenously as soluble protein (LRPPI-CAR strategy A) or can be membrane-anchored (LRPPI-CAR strategy B). If the target cell-binding CAR construct is membrane-anchored, it may also contain one or more intracellular signal transducing domains. Addition of lipocalin-fold ligand "b" induces interaction of the two constructs (containing the lipocalin-fold molecule "a" and the lipocalin-fold binding interaction partner "c"). The components "a" and "c" of the LRPPI system can be extracellularly (preferred) or intracellularly integrated (with or without linker sequences) into the two CAR constructs. Shown in FIGS. 2A and 2B is the fusion of the lipocalin-fold molecule "a" to the CAR construct that mediates target cell binding and fusion of the lipocalin-fold binding interaction partner "c" to the signal transducing construct, which, however, could also be reverse. Binding to the target cell can be mediated by any protein capable of binding to a chosen antigen on the target cell surface. In an alternative version (LRPPI-CAR strategy C) the lipocalin-fold molecule itself can directly bind to the antigen, whereby the antigen then is part of the LRPPI system and acts as lipocalin-fold binding interaction partner "c". The lipocalin-fold molecule "a" in this case is engineered by in vitro directed evolution using protein engineering technologies and subsequent selection for lipocalin-fold ligand-dependent binding to the lipocalin-fold binding interaction partner "c", which in this case is an antigen of a target cell.

Examples of CAR architectures are well-known in the art (e.g. reviewed by Abate-Daga et al., Mol Ther Oncolytics. 2016; 3:16014, and see e.g. WO 2014/127261 A1 and WO 2015017214 A1). In an embodiment, the signal transducing construct usually comprises one or two of the costimulatory signaling domains of the receptors CD27, CD28, CD134, CD137, ICOS, DAP12, activating NK cell receptors etc. (in any order from N- to C-terminus), with or without a domain for transmitting signal 1 (e.g. CD3 zeta), or alternatively comprises the inhibitory cytoplasmic domains of the inhibitory receptors PD1, CTLA4, LAG3, TIM3, inhibitory NK cell receptors etc. Transmembrane domains and extracellular membrane anchors can be derived from these receptors or from other proteins such as, e.g., CD3 zeta, CD8alpha, CD28 etc.

In LRPPI-CAR strategy B (FIG. 2B), the signal transducing domain(s) do not need to be necessarily confined to one of the two constructs, but instead could be separated from each other by fusing them to the two different CAR constructs separately (not shown). Further diversity arises due to the fact that both CAR constructs, the antigen binding and/or the signal transducing chain, can contain spacer domains comprised of fragments of the signal transducing proteins or of, e.g., IgG-Fc domains. Moreover, the antigen binding domains can be based on single-chain Fv fragments, endogenous receptor- or ligand domains (e.g., NKG2D, IL13 etc.) or any other available binder scaffold (Simeon et al., Protein Cell. 2017; DOI 10.1007/s13238-017-0386-). If the lipocalin-fold molecule itself is the binding domain engineered for binding to a chosen target antigen (LRPPI-CAR strategy C, FIG. 2C), the antigen on the target cell itself is part of the LRPPI system, i.e., representing the lipocalin-fold binding interaction partner "c". Principally, the binding domains of the CAR can be directed to any antigen, including non-protein antigens.

Accordingly, a preferred embodiment of the LRPPI system according to the present invention is a system, wherein the lipocalin-fold molecule is part of an ectodomain of a chimeric antigen receptor and wherein the lipocalin-fold binding interaction partner is a cell surface antigen.

Due to the nature of the present invention, the lipocalin-fold molecule and the lipocalin-fold binding interaction partner are preferably provided as polypeptides, especially polypeptides obtained by recombinant technologies. The molecules according to the present invention can—at least theoretically—also be provided by chemical syntheses; however, molecular biology techniques are, of course, the practically most relevant techniques for providing the lipocalin-fold molecule and the lipocalin-fold binding interaction partner. On the other hand, the lipocalin-fold ligand is preferably produced by chemical synthesis or by extraction from natural sources.

Accordingly, another aspect of the present invention relates to nucleic acid molecules comprising nucleotide sequences encoding the lipocalin-fold molecule and/or the lipocalin-fold binding interaction partner according to the present invention. The nucleic acid according to the present invention will in some embodiments be DNA or RNA, including, e.g., a recombinant expression vector. The nucleic acid molecules according to the present invention may also be provided in other form, e.g. in viral vectors. The nucleic acid molecules may be active or conditionally active in cells and be present or presents in some embodiments as RNA, e.g., in vitro or in vivo synthesized RNA or RNA packaged in a retrovirus, preferably RNA packaged in a lentivirus.

In some cases, the nucleic acid molecule of the present invention comprises a nucleotide sequence encoding only the lipocalin-fold molecule (and not the lipocalin-fold binding interaction partner). In some cases, the nucleic acid molecule of the present invention comprises a nucleotide sequence encoding only the lipocalin-fold binding interaction partner (and not the lipocalin-fold molecule). In some cases, the nucleic acid molecule of the present disclosure comprises a nucleotide sequence (or two separate nucleotide sequences) encoding both the lipocalin-fold molecule and the lipocalin-fold binding interaction partner of the present invention.

In the case where the lipocalin-fold molecule and the lipocalin-fold binding interaction partner are encoded by different nucleic acid molecules, the present invention provides a kit of at least two nucleic acid molecules, wherein the first nucleic acid molecule comprises nucleotide sequences encoding the lipocalin-fold molecule according to the present invention and wherein the second nucleic acid molecule comprises sequences encoding the lipocalin-fold binding interaction partner according to the present invention, wherein, again, the nucleic acids are preferably selected from DNA or RNA, more preferably in vitro transcribed RNA or RNA packaged in a retrovirus, especially RNA packaged in a lentivirus.

The present invention also provides a vector, e.g. a recombinant expression vector, comprising the nucleic acid molecules according to the present invention (i.e. encoding the lipocalin-fold molecule and/or the lipocalin-fold binding interaction partner) and/or the kit of nucleic acid molecules (encoding the lipocalin-fold molecule and the lipocalin-fold binding interaction partner).

Such a vector can include a selectable marker, an origin of replication, and other features that provide for replication and/or maintenance of the vector. Suitable vectors include, e.g., plasmids, viral vectors, and the like. Large numbers of suitable vectors and promoters are known to those of skill in the art; many are commercially available for generating the recombinant constructs according to the present invention. The following vectors are provided by way of example. Bacterial: pBs, phagescript, PsiX 174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden).

Eukaryotic: pWLneo, pSV2 cat, pOG44, PXR1, pSG (Stratagene) pSVK3, pBPV, pMSG and pSVL (Pharmacia). Vectors generally can have convenient restriction sites located near the promoter sequence to provide for the insertion of nucleic acid sequences encoding heterologous proteins. A selectable marker operative in the expression host may be present. Suitable vectors include viral vectors (e.g. viral vectors based on vaccinia virus, poliovirus, adenovirus, adeno-associated virus, SV40, herpes simplex virus, human immunodeficiency virus, a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus); and the like). Preferred vectors, due to the ability of efficiently integrating into the genome of the transduced cells, are retroviral vectors, especially gamma-retroviral vectors and lentiviral vectors, i.e. vectors derived from at least a portion of a retrovirus genome. An example of a preferred retroviral vector is a self-inactivating lentiviral vector (as provided in Milone et al., Mol Ther. 2009; 17(8):1453-1464). Other examples of lentivirus vectors that may be used in the clinic include, e.g., the LENTIVECTOR® gene delivery technology from Oxford BioMedica, the LENTIMAX™ vector System from Lentigen and the like. Nonclinical types of lentiviral vectors are also available and would be known to one skilled in the art. Other types of preferred vectors that can efficiently integrate into the genome of transfected cells are transposon vectors, preferably PiggyBAC-based vectors and Sleeping beauty-based vectors. Further important non-viral strategies for integrating a gene of interest into the genome of a cell are based on site-specific nuclease technologies (e.g., based on Zinc-finger nucleases (ZFNs) or transcription activator-like effector nucleases (TALENs)) or on CRISPR/Cas-technology (as described, e.g., by Gaj et al., Trends Biotechnol. 2013; 31(7):397-405; and Ren et al., Protein Cell 2017; 8(9):634-643). These technologies allow for integration of defined nucleotide sequences from any DNA molecule (single stranded DNA or double stranded DNA; in the form of a vector, PCR amplicon etc.) and are attractive because the gene of interest can be integrated into the genome downstream of endogenous promoters (as described, e.g., by Eyquem et al., Nature. 2017; 543(7643):113-117).

The present invention also provides a kit of at least two vectors, wherein the first vector comprises a nucleic acid molecule encoding the lipocalin-fold molecule according to the present invention and wherein the second vector comprises a nucleic acid molecule encoding the lipocalin-fold binding interaction partner according to the present invention. The two vectors may be provided with the same or different regulation sequences in order to achieve expression in the same or different host systems (e.g. suitable cells where the vectors express the lipocalin-fold molecule and/or the lipocalin-fold binding interaction partner after transformation with the vector or propagation).

In the vector or kit of vectors of the present invention, the nucleic acid molecules encoding the lipocalin-fold molecule and/or the lipocalin-fold binding interaction partner can be operably linked to a transcriptional control element, yielding an expression vector. Such a transcriptional control element can be e.g. a promoter, an enhancer, etc., wherein suitable promoter and enhancer elements are known in the art. For expression in a bacterial cell, suitable promoters include lacI, lacZ, T3, T7, gpt, lambda P and trc. For expression in a eukaryotic cell, suitable promoters include light and/or heavy chain immunoglobulin gene promoter and enhancer elements, cytomegalovirus immediate early promoter, herpes simplex virus thymidine kinase promoter, early and late SV40 promoters, promoter present in long terminal repeats from a retrovirus (e.g. the 5'-LTR of a gamma retrovirus or a promoter sequence comprising subelements R and U3 of the 5'-LTR of the Moloney murine leukaemia virus (MMLV)), promoter present in the murine stem cell virus (MSCV), mouse metallothionein-I promoter, EF1-alpha with or without intron, promoter of phosphoglycerate kinase (PGK), and various art-known tissue specific promoters. Suitable reversible promoters, including reversible inducible promoters are known in the art. Such reversible promoters may be isolated and derived from many organisms, e.g. eukaryotes and prokaryotes. Modification of reversible promoters derived from a first organism for use in a second organism, e.g. a first prokaryote and a second a eukaryote, a first eukaryote and a second a prokaryote, etc., is well known in the art. Such reversible promoters, and systems based on such reversible promoters but also comprising additional control proteins, include alcohol regulated promoters (e.g. alcohol dehydrogenase I (alcA) gene promoter, promoters responsive to alcohol transactivator proteins (AlcR), etc.), tetracycline regulated promoters, (e.g. promoter systems including TetActivators, TetON, TetOFF, etc.), steroid regulated promoters (e.g. rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g. metallothionein promoter systems, etc.), pathogenesis-related regulated promoters (e.g. salicylic acid regulated promoters, ethylene regulated promoters, benzothiadiazole regulated promoters, etc.), temperature regulated promoters (e.g., heat shock inducible promoters (e.g. HSP-70, HSP90, soybean heat shock promoter, etc.), light regulated promoters, synthetic inducible promoters, and the like.

In some instances, the locus or construct or transgene containing the suitable promoter can be irreversibly switched through the induction of an inducible system. Suitable systems for induction of an irreversible switch are well known in the art, e.g., induction of an irreversible switch may make use of a Cre-lox-mediated recombination. Any suitable combination of recombinase, endonuclease, ligase, recombination sites, etc. known to the art may be used in generating an irreversibly switchable promoter. Methods, mechanisms, and requirements for performing site-specific recombination, described elsewhere herein, find use in generating irreversibly switched promoters and are well known in the art. In some cases, the promoter is a CD8 cell-specific promoter, a CD4 cell-specific promoter, a neutrophil-specific promoter, or an NK-specific promoter. For example, a CD4 gene promoter can be used. As another example, a CD8 gene promoter can be used. NK cell-specific expression can be achieved by use of a Neri (p46) promoter. In some embodiments, e.g. for expression in a yeast cell, a suitable promoter is a constitutive promoter such as an ADH1 promoter, a PGK 1 promoter, an ENO promoter, a PYK 1 promoter and the like; or a regulatable promoter such as a GAL1 promoter, a GAL1O promoter, an ADH2 promoter, a PH05 promoter, a CUP1 promoter, a GAL7 promoter, a MET25 promoter, a MET3 promoter, a CYC1 promoter, a HIS3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX 1 (e.g. for use in *Pichia*). Selection of the appropriate vector and promoter is well within the level of ordinary skill in the art.

Suitable promoters for use in prokaryotic host cells include a bacteriophage T7 RNA polymerase promoter; a trp promoter; a lac operon promoter; a hybrid promoter, e.g. a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter, a pagC promoter, a nirB promoter, and the like; a sigma70 promoter, e.g. a consensus sigma70 promoter (see, e.g., GenBank Accession Nos. AX798980, AX798961, and AX798183); a stationary phase promoter, e.g. a dps promoter, an spv promoter, and the like; a promoter derived from the pathogenicity island SPI-2; an actA promoter; an rpsM promoter; a tet promoter; an SP6 promoter; and the like. Suitable strong promoters for use in prokaryotes such as *Escherichia coli* include Trc, Tac, T5, T7, and PLambda. Examples of operators for use in bacterial host cells include a lactose promoter operator (Laci repressor protein changes conformation when contacted with lactose, thereby preventing the Laci repressor protein from binding to the operator), a tryptophan promoter operator (when complexed with tryptophan, TrpR repressor protein has a conformation that binds the operator; in the absence of tryptophan, the TrpR repressor protein has a conformation that does not bind to the operator), and a tac promoter operator.

According to a preferred embodiment of the present invention, the vector or the kit of at least two vectors, or at least one, preferably a least two, of the vectors (in the kit) comprise a T lymphocyte-specific promoter or an NK cell-specific promoter operably linked to the nucleotide sequences encoding the lipocalin-fold molecule and/or the lipocalin-fold binding interaction partner.

According to a further aspect, the present invention also relates to a genetically modified cell which has been modified to produce the lipocalin-fold molecule and/or the lipocalin-fold binding interaction partner according to the present invention. Preferably, a cell is provided which has been modified to produce both, the lipocalin-fold molecule and the lipocalin-fold binding interaction partner according to the present invention. As an alternative, the present invention also provides a kit of at least two cells, wherein the first cell is genetically modified to produce the lipocalin-fold molecule according to the present invention and wherein the second cell is genetically modified to produce the lipocalin-fold binding interaction partner according to the present invention.

The cells according to the present invention are designed to be capable of expressing the lipocalin-fold molecule and/or the lipocalin-fold binding interaction partner. With the ligand regulated protein-protein interaction system according to the present invention, protein interaction can be regulated and steered within such a cell. As a research tool, all cells (which are in principle capable of being transformed with the nucleic acid molecules according to the present invention) as well as organisms comprising such cells may be designed with the ligand regulated protein-protein interaction system according to the present invention to address versatile biological and biochemical questions. The cells of the present invention may also be used to produce the vectors of the present invention (e.g. as virus or plasmid supernatant) from where they may then be further purified and provide these vectors in amplified and purified form.

According to a preferred embodiment, the cell (or the cells of the kit) are mammalian cells which are genetically modified to produce the lipocalin-fold molecule and/or the lipocalin-fold binding interaction partner according to the present invention. Preferred mammalian cells are stem cells, progenitor cells, or cells derived from a stem cell or a progenitor cell. Further preferred cells to be genetically modified according to the present invention are primary cells and immortalized cell lines. For pharmaceutical uses, human primary cells and human transformed cell lines are specifically preferred. However, also non-human cells and cell lines may be suitable cell types, especially for addressing scientific questions with the system according to the present invention, e.g. non-human primate cell lines, rodent (e.g., mouse, rat) cell lines, and the like.

Further preferred cells according to the present invention may be HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL1O), PC12 cells (ATCC No. CRL1721), COS cells, COS-7 cells (ATCC No. CRL1651), RAT1 cells, mouse L cells (ATCC No. CCL1.3), human embryonic kidney (HEK) cells (ATCC No. CRL1573), HLHepG2 cells, Hut-78, Jurkat, HL-60, NK cell lines (e.g., NKL, NK92, and YTS), and the like. In some preferred instances, the cell according to the present invention is not an immortalized cell line, but is instead a cell (e.g. a primary cell) obtained from an individual. For example, in some cases, the cell is an immune cell obtained from an individual. As an example, the cell is a T lymphocyte obtained from an individual. As another example, the cell is a cytotoxic cell obtained from an individual. As another example, the cell is a stem cell or progenitor cell obtained from an individual.

According to a specifically preferred embodiment, the mammalian cell according to the present invention, which is transformed with a vector or a kit of at least two vectors encoding the lipocalin-fold molecule and/or the lipocalin-fold binding interaction partner according to the present invention, is a T cell or an NK cell.

According to a further aspect, the present invention relates to a pharmaceutical preparation which comprises a nucleic acid molecule or a kit of nucleic acid molecules according to the present invention, a kit according to the present invention, a vector or a kit of vectors according to the present invention, or a cell or a kit of cells according to the present invention.

According to another aspect, the present invention also relates to a non-human animal comprising a cell (or cells) according to the present invention, which is capable of expressing the lipocalin-fold molecule and the lipocalin-fold binding interaction partner and which is therefore able to provide the system according to the present invention by e.g. the external addition of the lipocalin-fold ligand. With such a transgenic animal model, the ligand regulated protein-protein interaction system can be used in an in vivo model for addressing various biological questions both, scientifically and as test system for various industrial uses. Preferred animal models are those that are typically used in scientific research, such as primates, pigs, sheep, rodents, especially mice, rabbits and rats; chicken, frog (*Xenopus laevis*), insects, such as drosophila; zebrafish, etc. Specifically preferred animal models are those with an immune system which is similar to the human immune system, especially if the system according to the present invention is established as CAR (see above). Establishment of the ligand regulated protein-protein interaction system is also possible in plant cells. Accordingly, another aspect of the present invention relates to a plant comprising a cell (or cells) according to the present invention, which is also capable of expressing the lipocalin-fold molecule and the lipocalin-fold binding interaction partner and which is therefore also able to provide the system according to the present invention. Preferred plants wherein the system according to the present invention can be established are *Arabidopsis*, but also crop plants, such as corn, wheat, potato, tomato, soy, etc. Other preferred organisms are yeast and bacteria.

BRIEF DESCRIPTION OF THE DRAWINGS

The present invention is further described by the following examples and the figures, yet without being limited thereto.

FIG. 1 shows the schematics of the present invention as an LRPPI system based on a lipocalin-fold (A) and a preferred embodiment thereof (B). (A) lipocalin-fold molecule ("a") can accommodate in its calyx a small molecule lipocalin-fold ligand ("b") and can bind to a lipocalin-fold binding interaction partner "c" with higher affinity in the presence of "b"; (B) the lipocalin-fold molecule ("a") may be fused (+/−flexible linker) to terminal or internal sites of a protein "I" and also accommodates in its calyx a small molecule lipocalin-fold ligand ("b") and can bind to a lipocalin-fold binding interaction partner "c", which may be preferably a protein (that may be fused (+/−flexible linker) to terminal or internal sites of a further protein), with higher affinity in the presence of "b".

FIGS. 5A and 5B show sequences of rcSso7d- and FN3-based lipocalin-fold binding interaction partners. The amino acids differing from the original rcSso7d or FN3 sequence are highlighted in blue.

FIGS. 6A and 6B show schematics of the signal transducing constructs, i.e. the part of the CAR, in which either the lipocalin-fold molecule or the lipocalin-fold binding interaction partner is fused to the signaling domains.

FIGS. 7A, 7B, 7C and 7D show sequences of the signal transducing CAR constructs containing rcSso7d- and FN3-based RBP4 binding interaction partners.

FIGS. 8A and 8B show expression of the signal transducing CAR constructs in primary T cells: (A) Expression of constructs containing different rcSso7d-based RBP4 binding interaction partners; (B) Expression of constructs containing different FN3-based RBP4 binding interaction partners or alternatively RBP4 fused to the signaling domains.

FIG. 9 shows schematics of different antigen binding CAR constructs, i.e., the part of the CAR, in which an antigen binding domain is fused to lipocalin-fold molecule or the lipocalin-fold binding interaction partner. In the shown example either a scFv directed against CD19 or an rcSso7d directed against EGFR was used as antigen binding domain.

FIG. 10 shows sequences of the antigen binding CAR constructs.

FIG. 13 shows lipocalin-fold ligand (in this case 5 μM A1120) dependent function of the soluble fusion protein B when co-expressed in primary T cells together with CAR construct "RS3 long" ("RS3 long+co-elpo B"). T cells without CAR ("no construct") and T cells expressing only the signal transducing construct but no antigen binding construct ("RS3 long only") served as negative controls. T cells expressing an anti-CD19 CAR served as positive control. Depicted in (A) and (B) is the capacity for triggering IFN-γ production and cytotoxicity, respectively. Statistical significance was calculated using the paired two-tailed and the ratio paired two-tailed Student's t test for specific lysis and IFN-γ levels, respectively (*=p<0.05; ns=p>0.05).

FIG. 18 shows the overview of all performed affinity measurements for the RBP4 binding interaction partners RS3, RS5 and RF2 for binding to RBP4 in the presence and absence of A1120 with three different methods (*n.a., not analyzable).

FIG. 19 in panel B shows binding of TTR to yeast-displayed RBP4 in the presence (50 µM) or absence (PBSA) of different potential lipocalin-fold ligands.

DETAILED DESCRIPTION

Examples

Example 1: RBP4-Based LRPPI System

Figure 2:
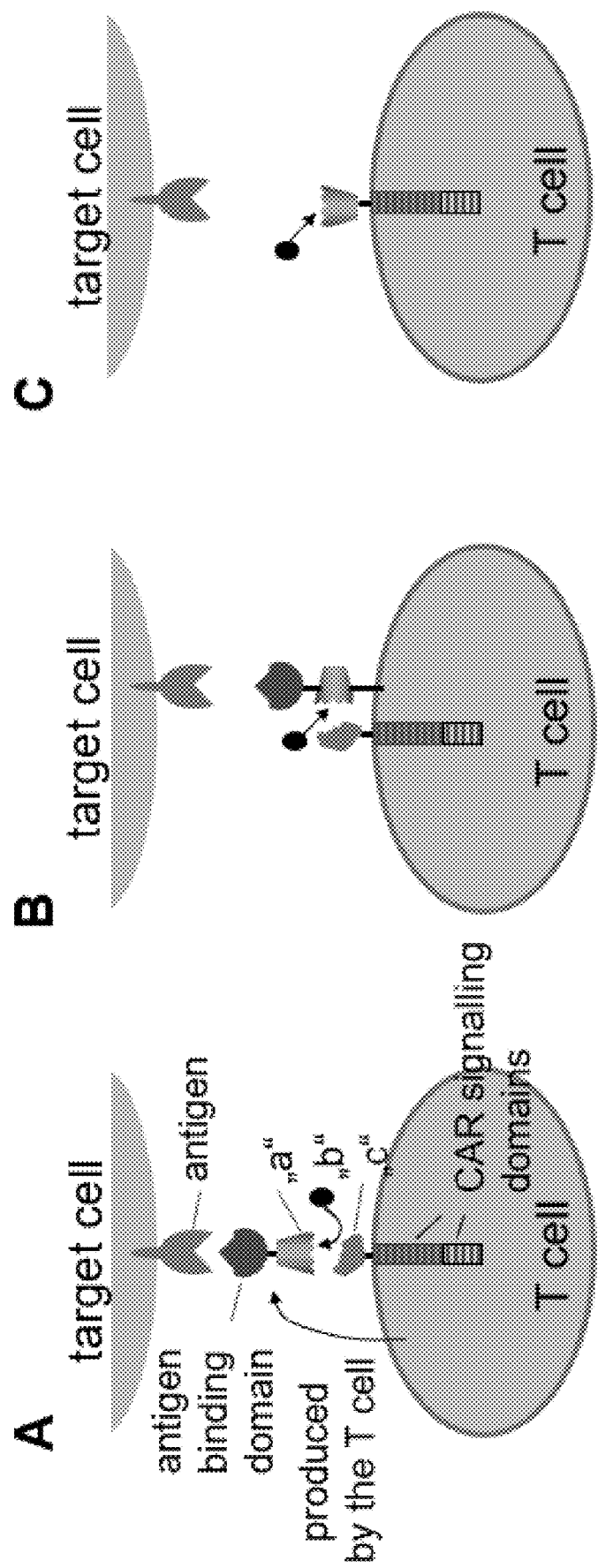
FIG. 2 shows a schematic example of lipocalin-fold molecule-based LRPPI systems according to the present invention integrated into CARs. "a" can be part of a soluble protein (secreted or exogenously added) or of a transmembrane construct and "c" can be part of a signal transducing construct (shown in A and B). Of course, "a" and "c" can be integrated in the constructs vice versa (not shown). There are many more possible arrangements (not shown). For example, the signal transducing domains do not need to be necessarily confined to one of the two constructs, and "a" and "c" can alternatively be part of the cytoplasmic domains of the constructs. (C) shows an example in which "c" is an antigen.
Figure 3:
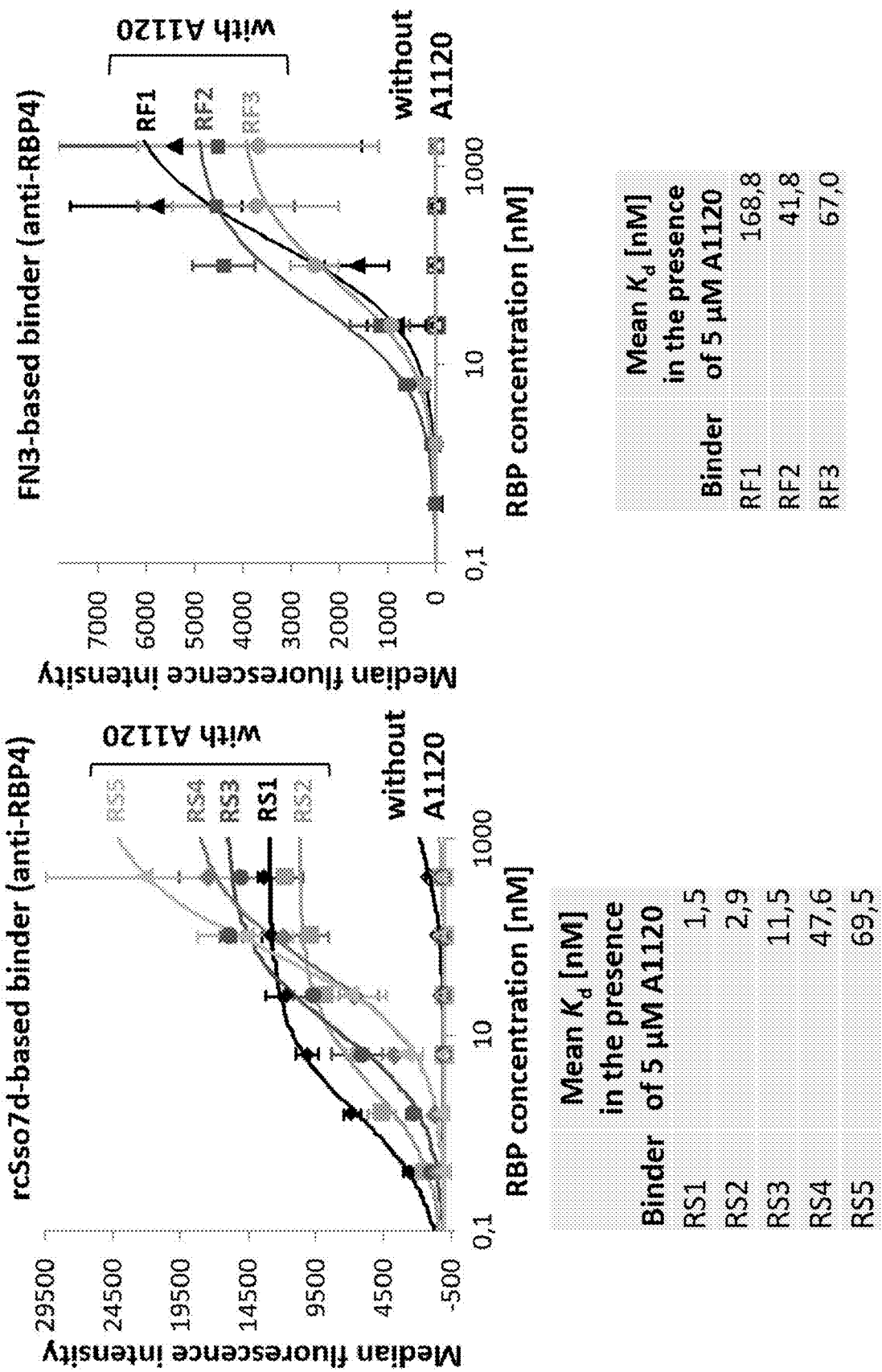
FIG. 3 shows A1120 dependent binding of increasing concentrations of human RBP4 to different rcSso7d- and FN3-based lipocalin-fold binding interaction partners displayed on the surface of yeast. The assay was performed in the presence (5 μM) or absence of the lipocalin-fold ligand A1120. RBP4-binding was detected with an anti-penta-His antibody and subsequently analyzed by flow cytometry.

For bovine and human RBP4 there are a series of ligands known to induce conformational changes in the loop regions, which result in dissociation of the natural protein partner TTR (see prior art cited above). In the present example, it is demonstrated by using human RBP4 and its synthetic non-retinoid ligand A1120 (PubChem CID 25138295) how such a ligand-induced conformational switch of a lipocalin-fold molecule can be used as an element in LRPPI. For this purpose, His-tagged full length RBP4 (UniProt ID P02753) was employed as antigen in an alternating screening process in presence (5 µM) and absence of A1120, respectively, in which ligand-dependent lipocalin-fold binding interaction partners were selected from libraries of two scaffolds with very different protein structure, i.e., FN3- and Sso7d-based scaffolds (Traxlmayr et al., J Biol Chem. 2016; 291(43):22496-22508; Chen et al., Methods Enzymol. 2013; 523:303-326). As described below, this process yielded lipocalin-fold binding interaction partners which bind RBP4 in an A1120-dependent manner. FIG. 3 shows the affinity of these lipocalin-fold binding interaction partners in the presence (5 µM) and absence of the RBP4-ligand A1120. The diagrams in FIG. 3 show the flow cytometric analysis of the binding intensity at different concentrations of human RBP4 in the presence (5 µM) or absence of A1120 to selected rcSso7d- or FN3-based lipocalin-fold binding interaction partners, which were displayed on the surface of yeast. RBP4-binding was detected by using an anti-penta-His antibody (Qiagen), followed by flow cytometric detection. rcSso7d-based lipocalin-fold binding interaction partners are termed RS1 through RS5, respectively, whereas FN3-based lipocalin-fold binding interaction partners are termed RF1, RF2 and RF3. The calculated $K_d$ values are displayed below the diagrams (mean of three measurements). These data in FIG. 3 clearly show that it is possible to engineer LRPPI systems based on lipocalin-fold molecules, i.e. that the affinity of a lipocalin-fold molecule "a" (in this case RBP4) to a lipocalin-fold binding interaction partner "c" (in this case different mutants based on the protein scaffolds rcSso7d or FN3) is increased in the presence of a lipocalin-fold ligand "b" (in this case A1120). Moreover, the data in FIG. 3 also show that LRPPI systems based on lipocalin-fold molecules can be engineered by using structurally diverse lipocalin-fold binding interaction partners (in this example based on either rcSso7d or FN3, respectively) containing binding sites that are structurally very different (in FN3-based binders the binding sites are composed of loop regions, whereas in rcSso7d-based binders the binding sites are composed of rigid β-strands; (Traxlmayr et al., J Biol Chem. 2016; 291(43):22496-22508; Chen et al., Methods Enzymol. 2013; 523:303-326)). This means that LRPPI systems based on lipocalin-fold molecules are not crucially dependent on a particular structure (i.e. fold) of the lipocalin-fold binding interaction partner and therefore such LRPPI systems are highly flexible regarding the choice of the lipocalin-fold binding interaction partner.

Figure 4:
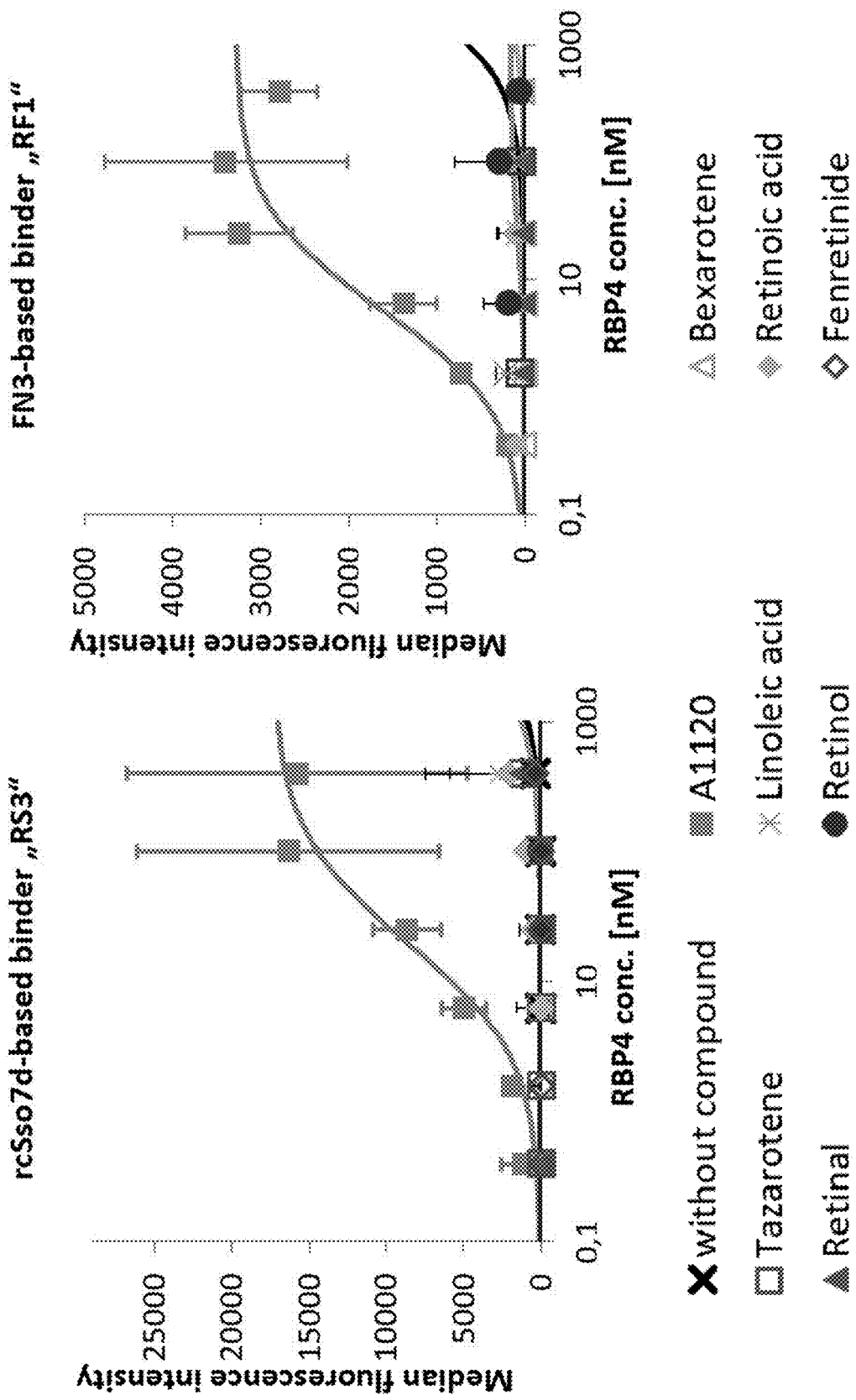
FIG. 4 shows binding of rcSso7d- and FN3-based lipocalin-fold binding interaction partners (displayed on the surface of yeast) to RBP4 loaded with different small molecules. All small molecules were present at a concentration of 5 μM. RBP4-binding was detected with an anti-penta-His antibody and subsequently analyzed by flow cytometry.

The possibility to engineer lipocalin-fold binding interaction partners that can specifically recognize conformational changes in the lipocalin-fold molecule induced by one lipocalin-fold ligand but not or much less the conformations induced by other lipocalin-fold ligands is a key advantage in engineering clinically applicable LRPPI systems that are orthogonal to each other and can work in parallel. FIG. 4 shows that the lipocalin-fold binding interaction partners selected for the A1120-induced conformation of RBP4 indeed have only very low or absent affinity to RBP4 loaded with other ligands known to induce conformational switching of RBP4. This was determined by flow cytometric analysis of the binding intensity (mean of three measurements) of different concentrations of human RBP4 in the presence (5 µM) or absence of the indicated ligands to selected rcSso7d- or FN3-based lipocalin-fold binding interaction partners, which were displayed on the surface of yeast. The sequences of the respective lipocalin-fold binding interaction partners are shown in FIGS. 5A and 5B.

Expression and Purification of Human RBP4

Human His-tagged RBP4 (residues 19-201) in pPICZ-alpha-A vector was kindly provided by John Findlay (Marie Curie lab for membrane proteins, Department of Biology, Maynooth University, Co Kildare, Ireland (Wysocka-Kapcinska et al., Protein Expr Purif. 2010; 71(1):28-32)) and the sequence was verified using Sanger-sequencing. The protein was expressed in *P. pastoris* strain KM71H. Cells were cultivated in YPG (2% peptone, 1% yeast extract, 1% glycerol) supplemented with Zeocin (100 µg/mL) at 30° C. and 180 rpm overnight. Cells were diluted on the following day and further cultivated until $OD_{600}$ of 2 was reached. Protein expression was induced by centrifugation of the cells and resuspension in YP-medium supplemented with 1% methanol and further incubation at 20° C. and 180 rpm for 3 days. Every day fresh methanol was added to a final concentration of 1% to enhance protein expression and subsequent secretion. After 3 days, the supernatant was harvested by 2-step centrifugation (1500 g, 15 min, 4° C. and 12200 g, 25 min, 4° C.) to first remove the cells and further small particles, respectively. Subsequently, diafiltration was performed to exchange the medium with 50 mM phosphate buffer, pH 7.5. The following purification protocol was adapted from Wysocka-Kapcinska et al. (Protein Expr Purif. 2010; 71(1):28-32).

Briefly, the diafiltrated supernatant was supplemented with 5 mM imidazole and applied to a HisTrap FF column (GE healthcare) connected to an ÄKTA FPLC purifier system to enable binding of the His-tagged RBP4 to the column. After washing with 50 mM phosphate buffer (pH 7.5 containing 500 mM NaCl and 5 mM imidazole), elution was performed using a linear imidazole gradient (from 5% to 100% with 50 mM phosphate buffer, pH 7.5, containing 500 mM NaCl and 500 mM imidazole). Absorbance at 280 nm was detected to observe elution of the protein and the corresponding fractions were analysed by SDS-PAGE. Those fractions showing both absorbance and the presence of a protein band at the expected size (22 kDa corresponding to the His-tagged RBP4), were pooled and concentrated using Amicon Ultra-15 10K Centrifugal filters (Merck Millipore). In addition, buffer was exchanged to phosphate buffered saline (PBS, pH 7.4) to prepare the protein solution for size exclusion chromatography (SEC) with a Superdex 200 column (10 mm×300 mm, GE Healthcare).

Before SEC, a fraction of RBP4 was labelled with biotin using the EZ-Link Sulfo-NHS-LC-LC-Biotin kit (Thermofisher Scientific). 10 mM biotin solution was added in a molar excess of 5:1 to the protein solution and incubated at room temperature for 1 hour while stirring. Subsequent preparative SEC was performed to remove remaining unbound biotin molecules and possible aggregates of RBP4, which could only be observed to a limited amount.

Screening for RBP4 Binding Interaction Partners Using Yeast Display

Two different scaffolds were used for screening of RBP4 binding interaction partners ("binders"), one of them being reduced charge Sso7d (rcSso7d), a small (7 kDa) thermostable DNA-binding protein from *Sulfolobus solfataricus* in which excess positive charges have been minimized previously (Traxlmayr et al., J Biol Chem. 2016; 291(43):22496-22508). The second binder scaffold is the tenth type III domain of human fibronectin (FN3), with a molecular weight of 10 kDa (Chen et al., Methods Enzymol. 2013; 523:303-326). Yeast libraries based on rcSso7d (rcSso7d-11 and rcSso7d-18), containing $1.4 \times 10^9$ transformants each and the library G4 based on the FN3 domain (Hackel et al., JMB 2010; 401:84-96), containing $2.5 \times 10^8$ transformants, were used. *S. cerevisiae* cells (strain EBY100) were grown in SD-CAA medium (20 g/L glucose, 6.7 g/L yeast nitrogen base, 5 g/L bacto casamino acids, 11.85 g/L sodium citrate dihydrate and 7.4 g/L citric acid monohydrate) at 30° C. overnight while shaking. On the following day, cells were sub-cultivated to an $OD_{600}$ of 1 in SD-CAA and growth was monitored by measuring the $OD_{600}$. After reaching a maximum $OD_{600}$ of 4, yeast cells were centrifuged and resuspended in SG-CAA medium (2 g/L glucose, 20 g/L galactose, 6.7 g/L yeast nitrogen base, 5 g/L casamino acids, 10.2 g/L disodium hydrogen phosphate and 4.82 g/L sodium phosphate monobasic) for induction of surface expression of rcSso7d- or FN3-mutants, respectively. Cells were incubated at 20° C. overnight with shaking and harvested by centrifugation. Two cycles of bead selection were performed with magnetic streptavidin-coated Dynabeads (Life technologies) loaded with biotinylated RBP4. To avoid the selection for non-specific binders or binders which are specific for streptavidin, negative selection (with bare beads) was performed between cycles of positive selection. In all bead selections, the RBP4 ligand A1120 was present at a concentration of 5 µM. After the second bead-selection cycle, error prone PCR (epPCR) was conducted in order to increase mutations in rcSso7d and FN3 genes which might contribute to binding. The plasmid DNA was subjected to 19 cycles of PCR using nucleotide analogs (2 µM of 8-oxo-2'-deoxyguanosine-5'-triphosphate, 8-oxo-dGTP, and 2 µM 2'-deoxy-p-nucleoside-5'-triphosphate, dPTP) and the primers epSso_fwd (5'-GGCTCTGGTGGAGGCGGTAGCG-GAGGCGGAGGGTCGGCTAGC-3') and epSso_rev (5'-CTATTACAAGTCCTCTTCAGAAATAAGCTTTTGTTCG-GATCC-3') for the rcSso7d-based lipocalin-fold binding interaction partners; and the primers FN3_fwd (5'-CGAC-GATTGAAGGTAGATACCCATACGACGTTCCAGAC-TACGCTCTGCAG3') and FN3_rev (5'-ATCTCGAGCTAT-TACAAGTCCTCTTCAGAAATAAGCTTTTGTTCGGAT CC-3') for the FN3-based lipocalin-fold binding interaction partners. The resulting product was used as a template for amplification by a second PCR. Afterwards, EBY100 cells were transformed with linearized pCTCON2 vector (Chao et al., Nat Protoc. 2006; 1(2):755-768; Angelini et al., Methods Mol Biol. 2015; 1319:3-36) and insert (PCR product) using the square wave protocol (single pulse, 500 V, 15 ms) and Bio-Rad Gene Pulser Xcell (Bio-Rad). After a third round of bead-selection (comprising 3 negative and 1 positive selection), libraries were further enriched by fluorescence activated cell sorting (FACS). Staining of yeast cells was performed in PBS supplemented with 0.1% bovine serum albumin (BSA) in the presence of 5 µM A1120 (Sigma-Aldrich) using 300 nM biotinylated antigen (RBP4) and 5 µg/mL mouse anti-c-myc antibody 9E10 (Thermo Fisher Scientific) and incubation at 4° C. for 1 hour while shaking. After a washing step, secondary staining was performed with 20 µg/mL streptavidin-Alexa Fluor 647 and 20 µg/mL anti-mIgG-AF488 (both from Thermo Fisher Scientific) for 20 minutes at 4° C. while shaking. After a final washing step, cells were sorted using a FACS Aria Fusion (BD). In some sorting rounds, cells were stained with non-biotinylated RBP4 as primary reagent followed by secondary staining with 1 µg/mL anti-HA-Alexa Fluor 647 (clone 16B12, BioLegend) and 5 µg/mL Penta-His-Alexa Fluor 488 (Qiagen), to avoid enrichment of binders recognizing biotinylated epitopes. Between the second and third FACS selection, another epPCR was performed. One round of negative selection was performed in which no A1120 was present and mutants with strongly reduced binding signal were sorted. In total, 6 or 7 rounds of FACS were performed for selection of RBP4-binding interaction partners.

Soluble Expression of Selected RBP4-Binding Interaction Partners

After the last selection round, 96 clones were sequenced. Based on the sequence, 16 RBP4-binders (9 rcSso7d- and 7 FN3-based lipocalin-fold binding interaction partners) were chosen and used for transformation of EBY100 cells. The affinity of single clones was determined by flow cytometry and titration of RBP4. Based on the affinity and the expression level, 8 binders (5 rcSso7d- and 3 FN3-based lipocalin-fold binding interaction partners) were further chosen for soluble expression. For this purpose, binders were subcloned into the pE-SUMO-vector (LifeSensors) and expressed as fusion proteins with His6-tagged small ubiquitin-like modifier (SUMO) protein. After transformation of Rosetta (DE3) *E. coli* cells (Merck Millipore) with the sequence-verified plasmids, cultures were incubated in LB medium supplemented with kanamycin (50 µg/mL) and chloramphenicol (34 µg/mL) at 37° C. overnight while shaking. Cells were diluted in terrific broth (12 g/L tryptone, 24 g/L yeast extract, 4% glycerol, 2.31 g/L $KH_2PO_4$ and 16.43 g/L $K_2HPO_4*3H_2O$) supplemented with kanamycin (50 µg/mL) and chloramphenicol (34 µg/mL) and further incubated at 37° C. until an $OD_{600}$ of 2 was reached. Expression was induced by addition of 1 mM isopropyl β-D-1-thiogalactopyranoside (IPTG) and cells were further cultured overnight at 20° C. On the following day, cells were harvested by centrifugation (5000 g, 20 min, 4° C.) and resuspended in sonication buffer (50 mM sodium phosphate, 300 mM NaCl, 3% glycerol, 1% Triton X-100, pH 8). After sonication (2×90 s, duty cycle 50%, amplitude set to 5) and centrifugation (20000 g, 30 min, 4° C.), purification of the supernatants containing the HIS6-SUMO-fusion proteins was performed using the TALON metal affinity resin (Clontech). Before application to the column, imidazole was added to the supernatants to a final concentration of 10 mM to avoid unspecific binding. Afterwards, supernatants were applied to the column twice, followed by several washing steps with equilibration buffer (50 mM sodium phosphate, 300 mM NaCl, pH 8) containing increasing amounts of imidazole (5-15 mM). Elution was performed with equilibration buffer supplemented with 250 mM imidazole. The buffer was exchanged to PBS using Amicon Ultra-15 10K Centrifugal filters (Merck Millipore) and the concentration was determined by measuring the absorbance at 280 nm with a Nanodrop instrument. A portion of the fusion-proteins was directly frozen at −80° C. while the rest was digested overnight at room temperature with SUMO-protease 1 (1 mg enzyme was used for 100 mg fusion-protein), resulting in cleavage of the hexahistidine tag and SUMO protein from the respective binder. The digested protein was again purified with TALON metal affinity resin (Clontech). His-tagged SUMO protein and His-tagged SUMO protease 1 bound to the resin while cleaved rcSso7d- or FN3-based lipocalin-fold binding interaction partners were found in the flow-through, which was further analyzed by SDS-PAGE. The absorbance at 280 nm of purified rcSso7d- and FN3-based lipocalin-fold binding interaction partners was determined by Nanodrop analysis and the concentration was calculated using the corresponding extinction coefficients. For biophysical measurements, the buffer was exchanged with PBS using Amicon Ultra-15 3K centrifugal filters (Merck Millipore) and the proteins were frozen at −80° C.

Biophysical Characterization of RBP4-Binding Interaction Partners

The stability of RBP4-binding interaction partners is evaluated by determining the melting temperature ($T_m$) by differential scanning calorimetry (DSC) using MicroCal VP-DSC capillary cell microcalorimeter (MicroCal). Briefly, 30 µM protein solution is exposed to an increasing temperature ranging from 20-110° C. with a heating rate of 1° C./min. Buffer baseline is subtracted and the resulting data are normalized for protein concentration, followed by fitting with a non-two-state thermal unfolding model.

Surface plasmon resonance (SPR) is used to determine the affinity of the interaction between RBP4 and rcSso7d- or FN3-based lipocalin-fold binding interaction partners and is performed with BiacoreT200 (GE healthcare). The antigen (RBP4) is coated onto a chip and incubated with various concentrations of binder solution in PBS, followed by a dissociation phase in PBS only. All measurements are performed both in the presence and absence of A1120 or other ligands. Finally, $k_{on}$, $k_{off}$ and $K_d$ values are obtained by global fitting.

For analytical SEC analysis, a total amount of 25 µg rcSso7d or FN3 mutants in running buffer (PBS with 200 mM NaCl) is filtered through 0.1 µm Ultrafree-MC filter (Merck Millipore), applied to a Superdex 200 10/300 GL column (GE healthcare) connected to an HPLC prominence LC20 system (Shimadzu) and eluted with a flow rate of 0.75 mL/min at 25° C. In addition, multi-angle light scattering (MALS) is used for determining the molecular mass using WYATT Heleos Dawn8+ plus QELS, a refractive index detector RID-10A (Shimadzu) and a diode array detector SPD-M20A (Shimadzu).

For the thermodynamic characterization of the interaction between RBP4 and rcSso7d- or FN3-based lipocalin-fold binding interaction partners, isothermal titration calorimetry (ITC) is conducted using an automated MicroCal PEAQ-ITC instrument (Malvern Instruments). The samples are centrifuged (17,000 g, 10 min, 20° C.) and filtered (0.1 µm Ultrafree-MC filter, Merck Millipore). RBP4 protein solution is applied to the sample cell and the respective binders are titrated with varying intervals. Different concentrations both for RBP4 and binders are used and in some experiments, binders are applied to the sample cell and RBP4 is titrated. The experiments are performed both in the presence and absence of the ligand A1120 or other ligands. Data analysis is performed with the MicroCal PEAQ-ITC analysis software.

Example 2: Identification of Clinically Applicable Lipocalin-Fold ligands with capacity for inducing conformational switching in a lipocalin-fold By using human RBP4 and its native interaction partner TTR we exemplified a strategy for identifying novel lipocalin-fold ligands with capacity for inducing conformational switching of a lipocalin-fold. With the aim of identifying clinically applicable lipocalin-fold ligands we performed a virtual screening of several databases (World Drug Index, KEGG Medicus, KEGG Ligands, DrugBank, Human Metabolome Database, ChEBI, ChEMBL, MDDR) with different stringency by using a pharmacophore model deduced from the RBP4/A1120 complex (PDB 3FMZ). The result of this virtual screening is shown in Table 1, which contains a series of approved and experimental drugs and other molecules potentially attractive for clinical and non-clinical applications.

TABLE 1

| Nr | database HMDB |
|---|---|
| 1 | Nafcillin |
| 2 | Gerberinol |
| 3 | Montelukast |
| 4 | Flurazepam |
| 5 | Quinidine barbiturate |
| 6 | Glyceollin I |
| 7 | Glyceollin II |
| 8 | (−)-Shinpterocarpin |
| 9 | Kanzonol W |
| 10 | 6alpha-Hydroxy-phaseollin |
| 11 | (1a,5b,6a)-7-Pro-toilludene-1,5,6,14-tetrol 14-(2,4-dihydroxy-6-methylbenzoic acid) |
| 12 | 4'-O-Methylkanzonol W |
| 13 | Cyclokievitone |
| 14 | Licofuranone |
| 15 | Armillatin |
| 16 | 2-(4-Methyl-3-pentenyl)-anthraquinone |
| 17 | Sorafenib beta-D-Glucuronide |
| 18 | Heterophyllin |
| 19 | 2'-O-Methylphaseol-linisoflavan |
| 20 | Tiapride |
| 21 | Gluten exorphin C |
| 22 | Mulberrofuran M |
| 23 | Dulxanthone G |
| 24 | Sclareol |
| 25 | Colupdox a |
| 26 | Kanzonol F |
| 27 | Mangostinone |
| 28 | Gancaonin X |
| 29 | Rubraflavone D |
| 30 | Cyclokievitone hydrate |
| 31 | Glyceollidin II |
| 32 | Cyclandelate |
| 33 | Dulxanthone E |
| 34 | Morusin |
| 35 | (E)-2',4,4'-Trihydroxy-3-prenylchalcone |
| 36 | Dulxanthone H |
| 37 | Judeol |
| 38 | Artonin E |
| 39 | Kanzonol T |

TABLE 1-continued

| Nr | |
|---|---|
| 40 | Fragransol A |
| 41 | Dulxanthone F |
| 42 | Mulberrofuran T |
| 43 | Garcimangosone A |
| 44 | Artonin B |
| 45 | Asteltoxin |
| | database KEGG |
| 46 | Oxyfedrine |
| 47 | Profluthrin |
| 48 | Momfluorothrin |
| 49 | Xyloylsulfamine |
| 50 | Cetotiamine hydrochloride hydrate |
| 51 | Dicethiamine hydrochloride hydrate |
| 52 | Dicetamin |
| 53 | Oxolamine |
| 54 | Oksalamin |
| 55 | Crisnatol mesylate |
| 56 | Ioflubenzamide I |
| 57 | Ceritinib |
| 58 | Zykadia |
| 59 | Imiprothrin |
| 60 | Triclabendazole |
| 61 | Fasinex |
| 62 | Brivanib alaninate |
| 63 | Transfluthrin |
| 64 | Enolicam sodium |
| 65 | Enolicam sodium monohydrate |
| 66 | Dibucaine |
| 67 | Cinchocaine |
| 68 | Nupercaine |
| 69 | Trametinib |
| | database WDI |
| 70 | FLUCLOXACILLIN |
| 71 | S-FARNESYLTHIOSALICYLIC ACID |
| 72 | 2-FLUOROTROPAPRIDE |
| 73 | BUTAMPICILLIN |
| 74 | DICLOXACILLIN SULFATE |
| 75 | FUROXACILLIN |
| 76 | IBUCILLIN |
| 77 | PRAZOCILLIN |
| 78 | SALETAMIDE |
| 79 | TETRACHLORSALICYLANILIDE |
| 80 | CARBENICILLIN |
| 81 | DICLOMETIDE |
| 82 | METHYL-SULFOMETURON |
| 83 | TRICHLOROSALICYLANILIDE |
| 84 | CLOMETOCILLIN |
| 85 | CYSTODYTIN-F |
| 86 | DETANOSAL |
| 87 | DIARBARONE |
| 88 | DICLOFOP |
| 89 | EPIPHENETHICILLIN |
| 90 | FTALIL-MEDEYOL |
| 91 | SALETAMIDE HYDROCHLORIDE |
| 92 | TIAPRIDE HYDRO CHLORIDE |
| 93 | TRUNCULIN-A |
| 94 | DEOXYPENTA LENYLGLUCURON |
| 95 | LAFLUNIMUS |
| 96 | MERAZOLAM |
| 97 | DIBUSADOL |
| 98 | PHENETICILLIN POTASSIUM |
| 99 | PRANOSAL |
| 100 | DALEFORMIS |
| 101 | DIPHENICILLIN |
| 102 | FENOTEROL HYDROCHLORIDE |
| 103 | GIGANTIC-ACID |
| 104 | HALOLITORALIN-B |
| 105 | ISOPROPICILLIN |
| 106 | PROGUANIL HYDROCHLORIDE |
| 107 | PYRANOKUNTHONE-B |
| 108 | TUBEROSIN |
| 109 | ZOPFIELLAMIDE-B |
| 110 | CLOXACILLIN SODIUM |
| 111 | LETIMIDE HYDROCHLORIDE |
| 112 | BAIGENE-B |
| 113 | BIDWILLON-B |
| 114 | CARBENICILLIN DISODIUM |
| 115 | HYDROXYPROCAINE |
| 116 | OCHRATOXIN-A |
| 117 | THEROX |
| 118 | MACARANGAFLAVANONE-B |
| 119 | MENOXYMYCIN-B |
| 120 | PENICILLIN-S |
| 121 | PSORALIDIN |
| 122 | RUBIGINONE-C1 |
| 123 | SECOPSUEDOPTEROSIN-E |
| 124 | ASADISULFIDE |
| 125 | BARANGCADOIC-ACID-A |
| 126 | BEPHEDON |
| 127 | MELLEDONAL-B |
| 128 | NERAMINOL |
| 129 | PHOMOPSOLIDE-A |
| 130 | ROBUSTIC-ACID |
| 131 | ZOPFIELLAMIDE-A |
| 132 | CYSTODYTIN-B |
| 133 | DICLOXACILLIN |
| 134 | FLUOROPROPRANOLOL |
| 135 | ILIOCICOLIN-B |
| 136 | INDICANINE-B |
| 137 | JACAREUBIN |
| 138 | KOTTAMIDE-C |
| 139 | MEXOLAMINE |
| 140 | MYCAPEROXIDE-H |
| 141 | OTOGIRIN |
| 142 | OXOLAMINE HYDROCHLORIDE |
| 143 | OXOPROPALINE-A |
| 144 | PURVALANOL-A |
| 145 | RUBIGINONE-C2 |
| 146 | TERACRYLSHIKONIN |
| 147 | CLODINAFOP-PROPARGYL-ESTER |
| 148 | MAZATICOL |
| 149 | SETHOXYDIM |
| 150 | SULFAGUANOLE |
| 151 | BALAPERIDONE |
| 152 | FLUCLOXACILLIN SODIUM |
| 153 | GEODIAMOLIDE-TA |
| 154 | LUCANTHONE-SULFOXIDE |
| 155 | MELLEOLIDE-D |
| 156 | NADOXOLOL HYDROCHLORIDE |
| 157 | BECLOBRIC-ACID-GLUCURONIDE |
| 158 | CLOXACILLIN |
| 159 | HYPERGUINONE-B |
| 160 | OLIGOSPOROL-A |
| 161 | PROPOXYCAINE HYDROCHLORIDE |
| 162 | RONIFIBRATE |
| 163 | SUDAN-BLUE-GN |
| 164 | TRICHODERMAMIDE-B |
| 165 | BOTRYLLAMIDE-A |
| 166 | CARFECILLIN |
| 167 | CLETHODIM |
| 168 | DUTADRUPINE |
| 169 | EPICOCHLIOQUINONE-B-14 |

TABLE 1-continued

| Nr | |
|---|---|
| 170 | FLURAZEPAM |
| 171 | HYDROXYFLUCLOXACILLIN |
| 172 | RHINACANTHIN-C |
| 173 | TEFLUBENZURON |
| 174 | XENYSALATE |
| 175 | ANTIMYCIN-A8A |
| 176 | ARTOINDONESIANIN-U |
| 177 | BRONCHOCAINE |
| 178 | ENOLICAM |
| 179 | IPAZILIDE |
| 180 | MORDANT-BROWN-1 |
| 181 | PROPRANOLOL PHENO-BARBITAL |
| 182 | PUGHIININ-A |
| 183 | AMPHIBINE-H |
| 184 | ARMILLARIC-ACID |
| 185 | CARINDACILLIN |
| 186 | CHLOROBIOCATE |
| 187 | CHLORPROGUANIL |
| 188 | CYLINDROL-B |
| 189 | ECLIPTALBINE |
| 190 | GARCIGERRIN-A |
| 191 | O-DEMETHYLCHLORO-THRICIN |
| 192 | SANGGENON-C |
| 193 | TETRAPTEROL-G |
| 194 | CHLORSULFURON |
| 195 | DEXAMETHASONE-DI-ETHYLAMINOACETATE |
| 196 | DIETHYXIME |
| 197 | PYRIDOVERICIN ESTER |
| 198 | SUBENDAZOLE |
| 199 | THIOCAINE |
| 200 | TRAPEZIFOLIXANTHONE |
| 201 | TRICLAZAN |
| 202 | 3',4'-DICHLOROBENZAMIL |
| 203 | CHAETOVIRIDIN-C |
| 204 | CYCLOGREGATIN |
| 205 | FLURAZEPAM MONO-HYDROCHLORIDE |
| 206 | FUSIDILACTONE-B |
| 207 | GRISEOCHELIN-METHYL-ISOBUTYL-SHIKONIN |
| 208 | |
| 209 | MICINICATE |
| 210 | AJUDAZOL-B |
| 211 | CYSTODYTIN-E |
| 212 | DEMETHYLPRAECANSONE-A |
| 213 | DESTRUXIN-A |
| 214 | DIFENIDOL EMBONATE |
| 215 | DISCOKIOLIDE-B |
| 216 | IRUMANOLIDE-2 |
| 217 | LACTOQUINOMYCIN |
| 218 | NEOBORNYVAL |
| 219 | SAROTHRALEN-D |
| 220 | ABYSSINONE-V |
| 221 | AXITIROME |
| 222 | CHLORFLUAZURON |
| 223 | CHONDRILLIDIENE-18,20 |
| 224 | EUGLOBAL-G2 |
| 225 | IDARUBICIN HYDRO-CHLORIDE |
| 226 | MUTISICOUMARANONE-A |
| 227 | 3-O-METHYL-CALOPOCARPIN |
| 228 | ALLOCLAMIDE HYDRO-CHLORIDE |
| 229 | ANOPTERINE |
| 230 | DIOXATION |
| 231 | EUGLOBAL-IIC |
| 232 | ILICICOLIN-C |
| 233 | MYCINOLIDE-II |
| 234 | SULLIN |
| 235 | TOCOTRIENOL-GAMMA |
| 236 | INDOMYCINONE-BETA |
| 237 | ISOTHIORBAMINE |
| 238 | MEBEVERINE |
| 239 | MUTISICOUMARANONE-D |
| 240 | NYMPHAEOL-C |
| 241 | PRUSOCAIN |
| 242 | ZIMET-20-84 |
| 243 | 2,4-D-BUTOXYPROPYL |
| 244 | ABYSSINONE-IV |
| 245 | BAIGENE-A |
| 246 | CHRYSOCHLAMIC-ACID |
| 247 | EPOLONE-B |
| 248 | ETHOXYCAINE |
| 249 | FLUORENAMIL |
| 250 | GUAIACOL-MEFENAMATE |
| 251 | MAXIMA-ISOFLAVONE-C |
| 252 | SARCODICTYIN-B |
| 253 | TRICLABENDAZOLE |
| 254 | ACHYOFURAN |
| 255 | ASTERRIQUINONE |
| 256 | DIETHYLGLYCOLATE-TOLYHYDRAZIDE |
| 257 | MALLOTOPHILIPPENS-D |
| 258 | NAFTOXATE |
| 259 | PACHYDICTYOL-A-EPOXIDE |
| 260 | RATJADONE |
| 261 | SALVERINE HYDRO-CHLORIDE |
| 262 | 4-MENAHYDROQUINONE |
| 263 | BOTRYLLAMIDE-C |
| 264 | ELSAMICIN |
| 265 | FENFLUTHRIN |
| 266 | MUTISIPHENONE-A |
| 267 | SANGGENONE-A |
| 268 | SCHWEINFURTHIN-A |
| 269 | VANYLIDILOL |
| 270 | 4-O-METHYLMELLEOLIDE |
| 271 | ACETYLVISMIONE-F |
| 272 | ALFENTANIL-HYDRO-CHLORIDE |
| 273 | ASPERTETRONIN-A |
| 274 | BETA-HYDROXYISO-VALERYLSHIKONIN |
| 275 | CARBISOCAINE |
| 276 | CHLORPROGUANIL HYDRO-CHLORIDE |
| 277 | CRYPTOPHYCIN-52 |
| 278 | DIDMETHYL-TOCOTRENOL |
| 279 | FLUOSOL-DA |
| 280 | PYRIDOXYPHEN |
| 281 | TIAZESIM HYDROCHLORIDE |
| 282 | BUTOCTAMIDE |
| 283 | DEOXYSHIKONIN |
| 284 | GAMBIERIC-ACID-A |
| 285 | LICOFURANONE |
| 286 | PREDNYLIDENE-DI-ETHYLAMINOACETATE |
| 287 | PSUEDOPTEROSIN-G |
| 288 | TRIKENDIOL |
| 289 | ZOAPATANOL |
| 290 | ERGOKININ-C |
| 291 | PENTAMOXANE HYDRO-CHLORIDE |
| 292 | SCANDENIN |
| 293 | ACTINOPYRONE-C |
| 294 | AMITON (als Bsp. für Gift!) |
| 295 | CRATOXYARBORENONE-C |
| 296 | CYMOPOL |
| 297 | DOXYCYCLINE-HYCLATE |
| 298 | FLAVIDULOL-C |
| 299 | FRAN-12 |
| 300 | MYRIAPORONE-3 |
| 301 | ORINOCINOLIDE |
| 302 | TONABERSAT |
| 303 | VISMIONE-B |
| 304 | AMIKHELLINE |
| 305 | BUTAMOXANE HYDRO-CHLORIDE |
| 306 | CHLOROBIOCIN |
| 307 | CYCLOCOMMUNIN |
| 308 | FENAZAFLOR |
| 309 | VISMIONE-D |

TABLE 1-continued

| Nr | |
|---|---|
| 310 | 3-TRICHLORMETAPHOS |
| 311 | AMINOPROPYLONE PHENYLBUTAZONE |
| 312 | DIOCLENOL |
| 313 | GRIFOLIN |
| 314 | HYPERJOVINOL-A |
| 315 | TAMOLARIZINE |
| 316 | TOMENTOL |
| 317 | TRANS-DELTA-TOCOTRI-ENOLOIC-ACID |
| 318 | DIACETOLOL HYDRO-CHLORIDE |
| 319 | DUTOMYCIN |
| 320 | LIGUROBUSTOSIDE-O |
| 321 | RAISPAILOL-B |
| 322 | ERECTQUIONE-A |
| 323 | SAROTHRALEN-A |
| 324 | SITAMAQUINE |
| 325 | TRICHOPOLYN-II |
| 326 | 3-HYDROXYTOLUFAZEPAM |
| 327 | DIMETPRAMIDE |
| 328 | FENOREROL HYDRO-BROMIDE |
| 329 | PHENKAPTON |
| 330 | CRATOXYARBORENONE-B |
| 331 | ETHOMOXANE HYDRO-CHLORIDE |
| 332 | ISOCENTRATHERIN |
| 333 | KALIMANTACIN-A |
| 334 | HISPAGLABRIDIN-A |
| 335 | LANKACYCLINOL |
| 336 | MCALURAXANTHONE |
| 337 | PIVAMPICILLIN HYDRO-CHLORIDE |
| 338 | PLURAFLAVIN-A |
| 339 | SIGMOIDIN-I |
| 340 | FENALAMIDE |
| 341 | HYDROXYACLACINOMY-CIN-M,2 |
| 342 | SOPHORADIN |
| 343 | ASCOSCHLORIN |
| 344 | BETA-HYDROXYSANSHOOL |
| 345 | BISTRAMIDE-K |
| 346 | CHLORTETRACYCLINE BORATE |
| 347 | DEHYDROASCOCHLORIN-8+,9+ |
| 348 | DIMETHIALIUM CHLORIDE |
| 349 | MACARANGIN |
| 350 | MARCELLOMYCIN |
| 351 | BENZOYLGMOISIN-H |
| 352 | CLINDAMYCIN HYDRO-CHLORIDE |
| 353 | HYDROXYASCOCHLORIN-8+ |
| 354 | NEOCARZILIN-A |
| 355 | CHAETOVIRIDIN-B |
| 356 | CHLORTETRACYCLINE BISULFATE |
| 357 | NAPYRADIMYCIN-C1 |
| 358 | SAROASPIDIN-B |
| 359 | SARRACINE |
| 360 | ERECTONE-B |
| 361 | HOMOHARZIANIC-ACID |
| 362 | ASTERRIQUINONE-B1 |
| 363 | DETAMID |
| 364 | RUBRAXANTHONE |
| 365 | DOLASTATIN-19 |
| 366 | EDETOL |
| 367 | PHASEOLLIDIN |
| 368 | GEDOCARNIL |
| 369 | MANUMYCIN-B |
| 370 | SANTALOL-BETA-SALICYLATE |
| 371 | COWANIN |
| 372 | INDIBULIN |
| 373 | COWANIN |
| 374 | KARATAVICIN |
| 375 | PICLOXYDINE |
| 376 | PROXAZOLE |
| 377 | STROBILURIN-E |
| 378 | ERECTQUIONE-B |
| 379 | SURICAINIDE |
| 380 | DIETHYLAMINOMETHYL-RUTIN |
| 381 | TROPESIN |
| 382 | PICLOXYDINE HYDRO-CHLORIDE |
| 383 | HEX-1 |
| 384 | DECLOVANILLOBIOCIN |
| database MDDR | |
| 385 | RUBIGINONE C2 |
| 386 | FLOBUFEN |
| 387 | TETRONOTHIODIN |
| 388 | LAFLUNIMUS |
| 389 | MYCAPEROXIDE A |
| 390 | FLURAZEPAM HYDRO-CHLORIDE |
| 391 | RUBIGINONE C1 |
| 392 | CRISNATOL MESYLATE |
| 393 | DOLASTATIN D |
| 394 | EPOLACTAENE |
| 395 | LEXIPAFANT |
| database CHEMBL | |
| 396 | CARBENICILLIN |
| 397 | DICLOFOP |
| 398 | EPIPHENITICILLIN |
| 399 | FLOBUFEN |
| 400 | GIGANTIC ACID |
| 401 | PHENETICILLIN POTASSIUM |
| 402 | DIPHENICILLIN |
| database Pubchem | |
| 403 | Acotiamide |
| 404 | Acoziborole |
| 405 | Acumapimod |
| 406 | Apalutamide |
| 407 | ASP3026 |
| 408 | AZD1480 |
| 409 | BIIB021 |
| 410 | Branplam |
| 411 | Brequinar |
| 412 | Chlorproguanil |
| 413 | Emricasan |
| 414 | Enasidenib |
| 415 | Enolicam |
| 416 | Flurazepam |
| 417 | ILX295501 |
| 418 | Indibulin |
| 419 | Metoclopramide |
| 420 | Mevastatin |
| 421 | MK0686 |
| 422 | Navarixin |
| 423 | Nefazodone |
| 424 | Pantoprazole |
| 425 | Pavinetant |
| 426 | SCYX-7158 |
| 427 | Siccanin |
| 428 | Sulfoguanole |
| 429 | Sunitinib |
| 430 | Suvorexant |
| 431 | Tiapride |
| 432 | Tonabersat |
| 433 | Ulimorelin |
| 434 | Xipammide |
| 435 | MGGBYMDAPCCKCT-UHFFFAOYSA-N |
| 436 | VNBRGSXVFBYQNN-UHFFFAOYSA-N |
| 437 | YUHNXUAATAMVKD-PZJWPPBQSA-N |
| 438 | LMI070 |
| 439 | Erlotinib |
| 440 | Tanespimycin |

The capacity of some of these ligands for inducing conformational switching of RBP4 is detected by exploiting the conformation dependent binding of TTR, which is inhibited by ligands with capacity for inducing conformational switching of RBP4.

Flow Cytometric Detection of Ligand Induced Conformational Switching of RBP4

RBP4-encoding DNA is isolated out of *P. pastoris* using the zymoprep yeast plasmid miniprep kit II (Zymo Research) followed by amplification by PCR using the primers picZalpha_fwd (5'-ATTGCCAGCATTGCTGCTAAAGAAG-3') and picZalpha_rev (5'-GCAAATGGCATTCTGACATCC-3'). The DNA is purified using the illustra GFX PCR DNA and Gel Band Purification Kit (GE healthcare) and sequenced. For cloning into the vector pCTCon2, the RBP4-encoding DNA is amplified with PCR using primers encoding NheI/BamHI restriction sites homologous to the vector. After digestion with NheI and BamHI (both New England Biolabs), the RBP4 encoding sequence is ligated into the linearized vector and electroporated in *E. coli* for verification of the sequence. The different domains of the resulting fusion protein have the order Aga2p—HA-tag—(Gly$_4$Ser)$_3$ Linker—RBP4—c-myc Tag. *S. cerevisiae* strain EBY100 is then transformed with the Quick and easy transformation kit (Takara).

Expression of RBP4 on yeast is induced by culturing the cells in SG-CAA medium (2 g/L glucose, 20 g/L galactose, 6.7 g/L yeast nitrogen base, 5 g/L casamino acids, 10.2 g/L disodium hydrogen phosphate and 4.82 g/L sodium phosphate monobasic) overnight at 20° C. and 180 rpm. For detection of RBP4 expression on the surface of yeast cells, cells are stained with either mouse anti-c-myc antibody 9E10 (Thermo Fisher Scientific) followed by secondary staining with anti-mIgG-AF488 (Thermo Fisher Scientific) or with anti-HA-Alexa Fluor 647 (BioLegend).

Flow cytometric detection of ligand induced conformational switching of RBP4 is based on employing the conformation dependent binding behaviour of TTR. Hereto, recombinant TTR (labelled with Alexa Fluor 488 NHS ester kit, Thermo Fisher Scientific) is added to RBP4-expressing yeast in absence or presence of different concentrations of various small molecule ligands in the staining buffer (PBS supplemented with 0.1% BSA).

Example 3: Integration of an RBP4-Based LRPPI System into a CAR

Figure 8B:
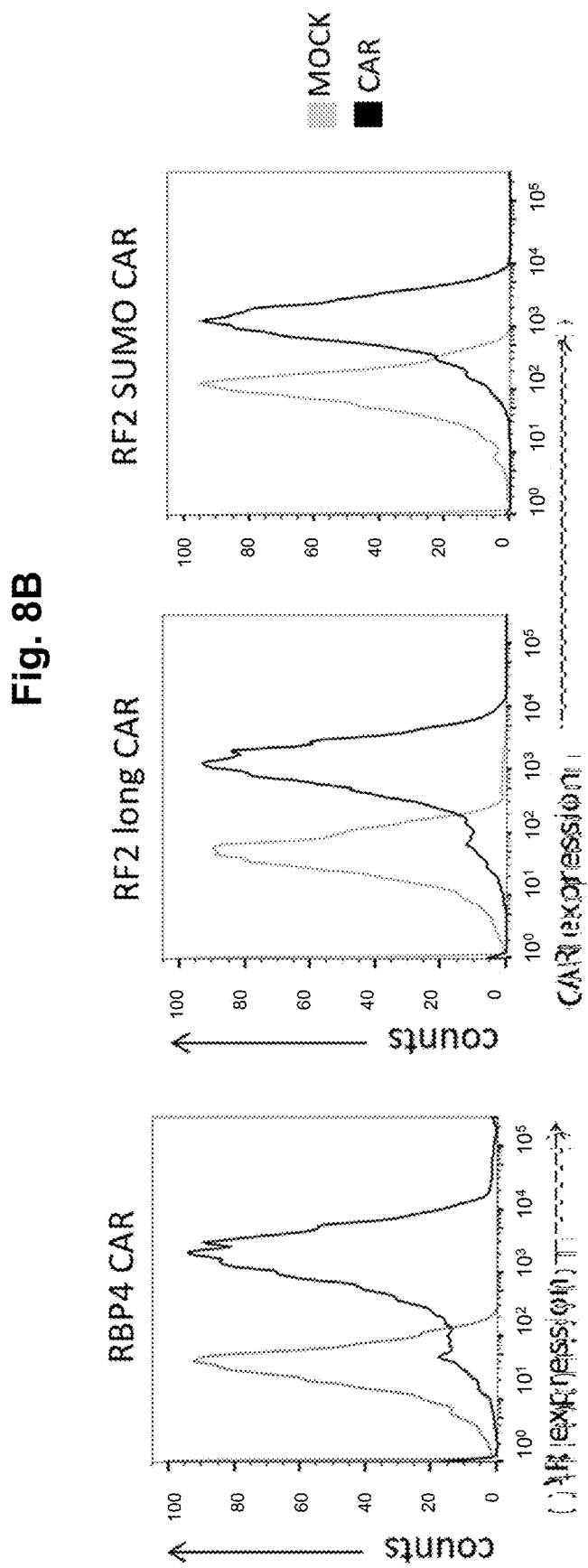
Figure 11:
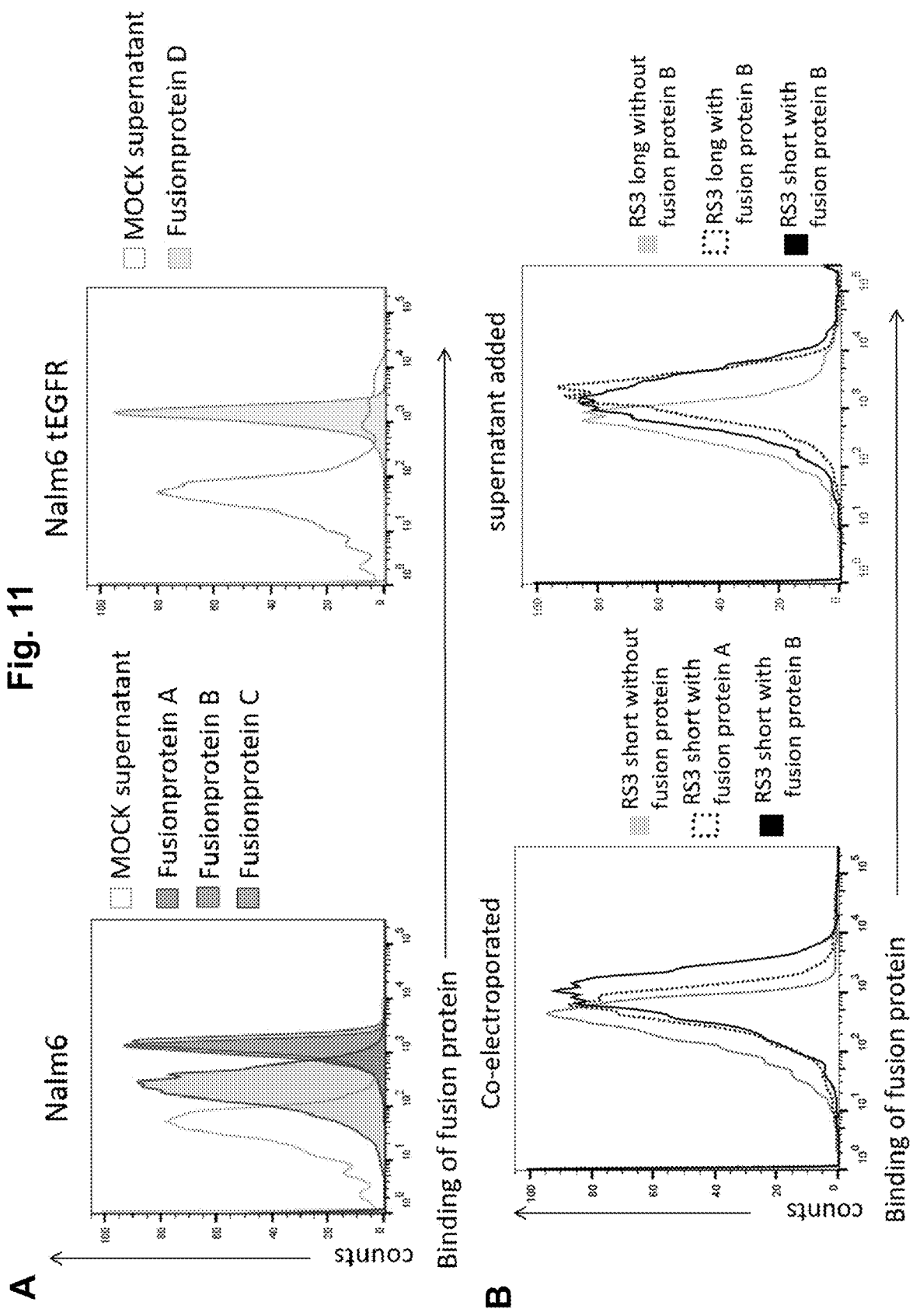
FIG. 11 shows the binding of antigen binding constructs (fusion proteins A-D) to antigen expressing target cells (A) and signaling CAR construct expressing primary human T cells (B): (A) CD19 positive Nalm-6 cells with and without stable expression of a truncated EGFR (tEGFR) were co-incubated with supernatants of Jurkat cells expressing fusion proteins A-D, as indicated; (B) Fusion proteins were either co-expressed in primary human T cells "co-electroporated") or added to primary T cells as supernatants obtained from Jurkat cells that expressed the fusion proteins ("supernatant added"). The primary T cells expressed a signaling transmembrane CAR construct that was either RS3 short CAR or RS3 long CAR, as indicated. Staining of fusion protein binding was performed in the presence of 5 μM A1120.
Figure 12:
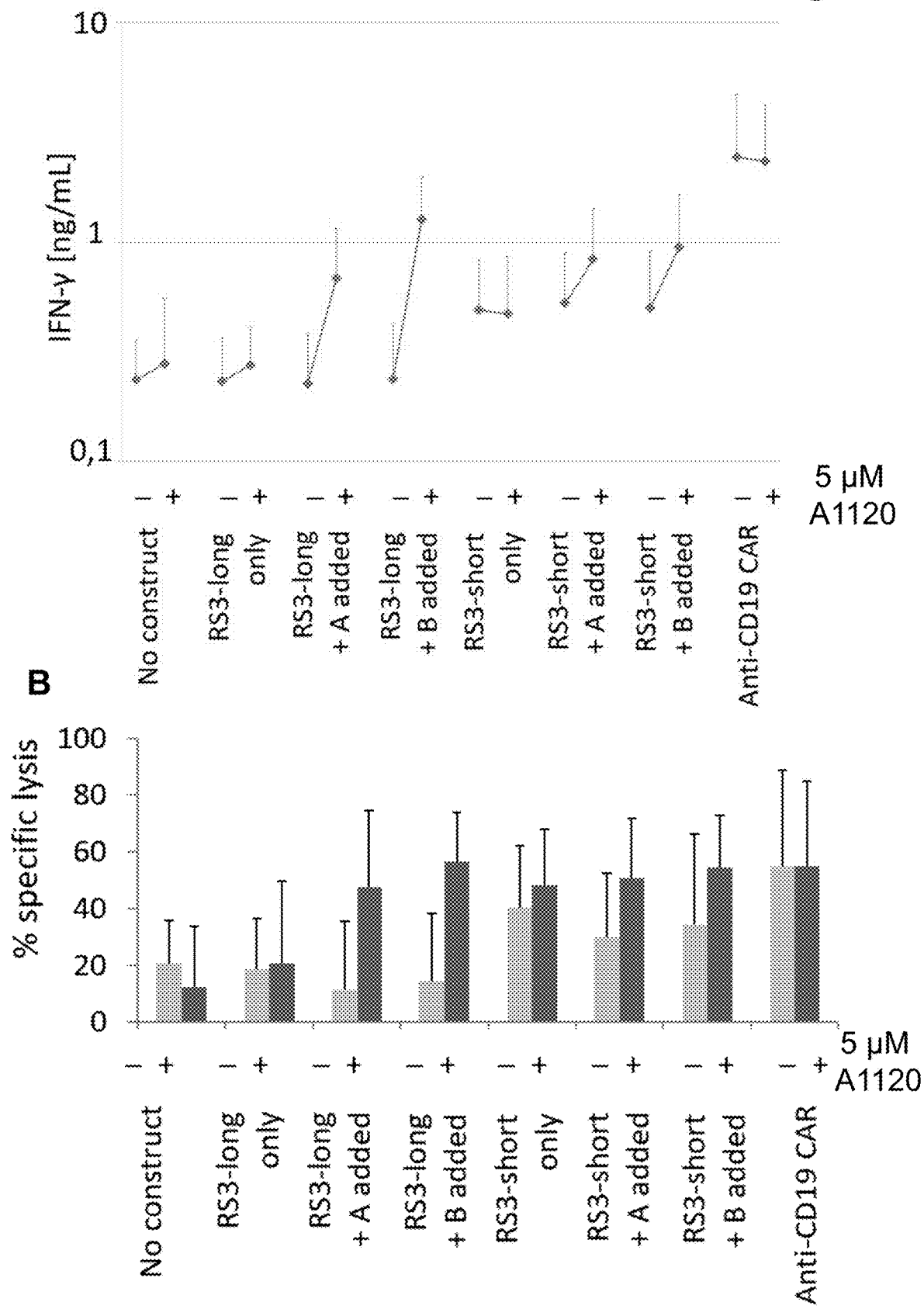
FIG. 12 shows lipocalin-fold ligand (in this case 5 μM A1120) dependent function of different CAR variants in primary T cells, whereby the soluble CAR constructs (fusion proteins A and B) were expressed in Jurkat cells and the supernatants therefrom were added to the primary T cells as indicated. Depicted in (A) and (B) is the capacity for triggering IFN-γ production and cytotoxicity, respectively.

The third example demonstrates the applicability of a LCN-fold based LRPPI for regulation of CAR function by using the RBP4-based LRPPI system described in example 1. The schematics of the CAR constructs shown in FIGS. 6A, 6B and 9 illustrate some tested possibilities of integrating such a lipocalin-fold based LRPPI into a CAR. FIGS. 7A, 7B, 7C, 7D and 10 show the sequences of the tested constructs and FIGS. 8A, and 8B illustrate the expression of signaling CAR constructs in primary human T cells. Primary human T cells were electroporated with 5 μg mRNA for each construct and CAR expression was detected 20 h after electroporation via Strep II Tag or in the case of "RS3 CAR long without c-myc Tag" and "RF2 long CAR" via the Fc domain by using a biotinylated anti-human-IgG1-antibody as primary antibody and a PE-conjugated streptavidin as secondary staining reagent. FIGS. 11A and 11B show the binding of CAR constructs containing the antigen binding domain (fusion proteins A-D, detected via the integrated His Tag) to target cells and to primary human T cells expressing different transmembrane CAR signaling constructs in the presence of 5 μM A1120 (20 h after electroporation of 5 μg mRNA). The fusion proteins were either co-expressed in the primary T cells or added to the primary T cells as supernatants obtained from Jurkat cells that expressed the fusion proteins. The ligand-dependent function of the resulting CARs, as determined by induction of cytotoxicity and cytokine production of primary human T cells in absence and presence of 5 μM A1120, is shown in FIGS. 12 and 13.

Design of CARs

Selected rcSso7d- and FN3-based RBP4-binding interaction partners were incorporated into a second-generation CAR signaling backbone, comprising a CD8 stalk, a 4-1BB costimulatory domain and a CD3zeta signaling domain ("8a-BBz"), or an IgG-Fc spacer fused to a CD28 costimulatory domain and a CD3zeta signaling domain ("Fc-28z"), respectively. RBP4-binding interaction partners based on rcSso7d (RS1-RS5) and Fibronectin (RF1-RF3) were fused to the CAR backbones via a Strep-Tag and one or two repeats of G4S (4× glycine and 1× serine) amino acid residues as linker. The composition of the constructs is given in the schematics of FIGS. 6A and 6B and the sequences are shown in FIGS. 7A, 7B, 7C and 7D. The secreted antigen binding CAR constructs contained either a FMC63-based scFv directed against human CD19 or rcSso7d directed against human EGFR fused to either IgG1-Fc-RBP4, or RBP4 or alternatively a lipocalin-fold binding interaction partner rcSso7d RS3. The schematics and sequences are shown in FIGS. 9 and 10, respectively. CAR constructs were constructed by Gibson Assembly (NEB), using 0.02-0.5 pmol of 2-3 PCR-amplified DNA fragments and 0.2-1 pmol of 4-6 PCR-amplified DNA fragments for assembly, respectively. The resulting constructs were amplified by PCR and subsequently used for in vitro transcription.

In Vitro Transcription and Electroporation of mRNA

In vitro transcription was performed with 50-200 ng of purified PCR product using the mMessage mMachine T7 Ultra Kit (Ambion) according to the manufacturer's instructions. The resulting mRNAs were column purified with an adapted protocol using the RNeasy Kit (Qiagen). According to this protocol, RLT buffer from the kit and 1% beta-mercaptoethanol were added followed by addition of absolute ethanol. The mixture was loaded onto an RNeasy column and purification was performed following the manufacturer's protocol. Purified mRNAs were frozen at −80° C. until electroporation. For CAR expression, Jurkat cells and primary T cells were electroporated with 5 or 10 μg mRNA using the Gene Pulser (Biorad) (square wave protocol, 500 V, 5 ms, 4 mm cuvettes).

Detection of the Expression of Signaling CAR Constructs

Expression of rcSso7d- and FN3-based CARs was detected via the Strep-II Tag using an anti-Strep-II Tag antibody (clone 5A9F9, GenScript) as primary antibody and a PE-conjugated secondary antibody (eBioscience). CARs containing an IgG spacer were detected by using a biotinylated anti-human-IgG1-antibody as primary antibody and a PE-conjugated streptavidin as secondary staining reagent. Finally, cells were analyzed by flow cytometry.

Detection of Binding of the Antigen Binding CAR Constructs Fusion Proteins A-D

Binding of fusion proteins A-D, which were either co-expressed with the signaling CAR constructs or produced by Jurkat cells, was detected by flow cytometry. Accordingly, 25×10$^3$ cells were either first incubated with fusion protein-containing supernatant for 45 min at 4° C. in the presence of 5 μM A1120 (Sigma-Aldrich) and thereafter washed in the presence of 5 μM A1120 before the second step staining with anti-penta-His antibody (Qiagen), or were directly stained with the anti penta-His antibody for 25 min at 4° C. Before flow cytometric analysis, two washing steps were performed again in the presence of A1120.

Cytotoxicity Assay

Analysis of the cytotoxic potential of CAR T cells was performed by a luciferase-based cytotoxicity assay. Therefore, luciferase-expressing tumor target cells were co-cultured with CAR T cells at different effector:target cell ratios (1:1, 2:1, 5:1, 10:1, 25:1, 100:1) in round-bottom 96 well plates for 4 h or 24 h at 37° C. Remaining living cells were then quantified by addition of luciferin (150 μg/mL final concentration; Perkin Elmer) and luciferase activity was measured by using the ENSPIRE Multimode plate reader. The percentage of specific lysis was determined with the following formula:

% killing=100−((*RLU* from well with effector and target cell co-culture)/(*RLU* from well with target cells only)×100)).

Cytokine Release by CAR T Cells and CAR-Expressing Jurkat Cells

Secretion of cytokines into supernatants was assessed by coculturing the target cells with effector cells at effector:target (E:T) ratios of 1:1 or 2:1 in flat-bottom 96 well plates for 4 or 24 h at 37° C. The supernatants were centrifuged (1600 rpm, 7 min) to remove remaining cells and were frozen at −20° C. For analysis of secreted cytokines, IFN-γ ELISA was performed using the Human IFN gamma ELISA Ready-SET-Go!® (eBioscience) according to the manufacturer's instructions. Secreted IL-8 was quantified by IL-8 Ready-SET-Go!® ELISA (Thermo Fisher Scientific). Measurements were conducted using the ENSPIRE Multimode plate reader.

Example 4: Biophysical Characterization of RBP4 Binding Interaction Partners

The RBP4 binding interaction partners of example 1 (in this case the lipocalin-fold binding interaction partners) were further characterized with different biophysical methods. DSC analysis clearly demonstrated that the RBP4 binding interaction partners RS3, RS5 and RF2 are stable proteins. Moreover, SEC analysis showed that the RBP4 binding interaction partners RS3, RS5 and RF2 are well folded, monomeric proteins.

Figure 15:
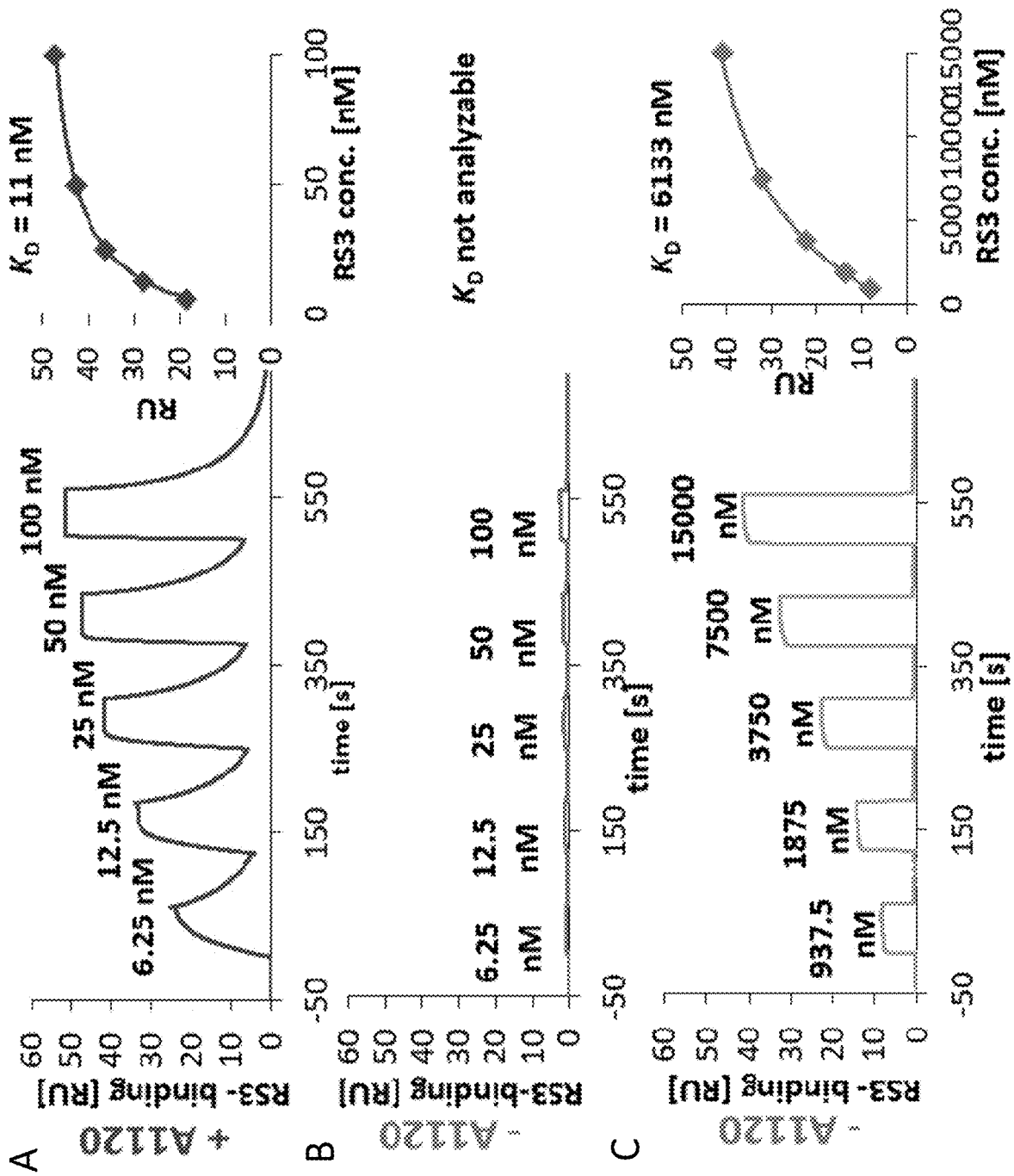
FIG. 15 shows analysis of the affinity of the RBP4 binding interaction partner RS3 to RBP4 by surface plasmon resonance (SPR). (A) Binding of RS3 to RBP4 in the presence of 5 μM A1120. (B) and (C) Binding of RS3 to RBP4 in the absence of A1120. Applied concentrations of RS3 are indicated in the plots. Steady state analysis of $K_d$ values (dissociation constants) is shown in the right panel of A and C.
Figure 17A:
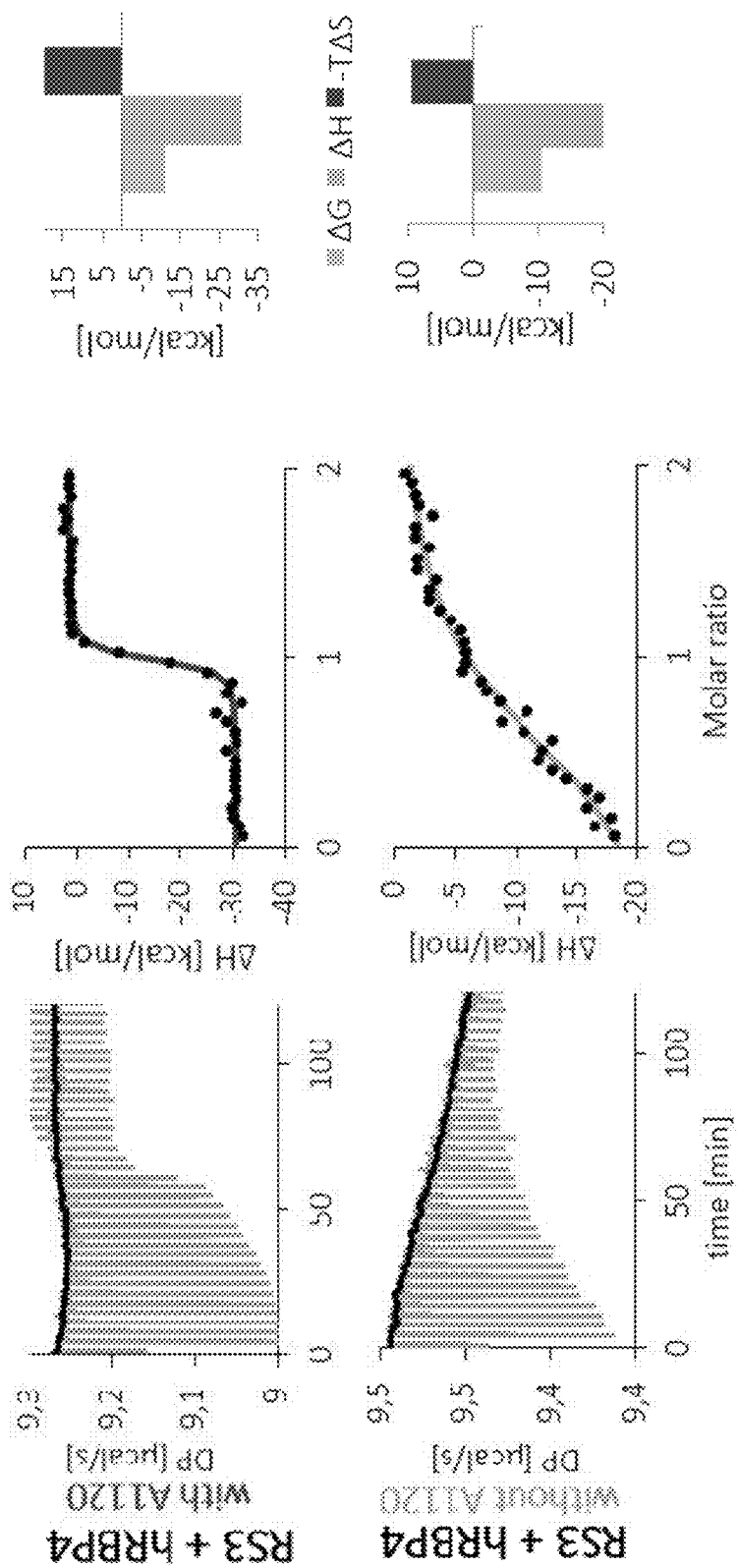
FIGS. 17A-17C show analysis of the affinities of the RBP4 binding interaction partners RS3 (A), RS5 (B) and RF2 (C) to RBP4 in the presence (50 μM) and absence of A1120 as determined by isothermal titration calorimetry (ITC).
Figure 17B:
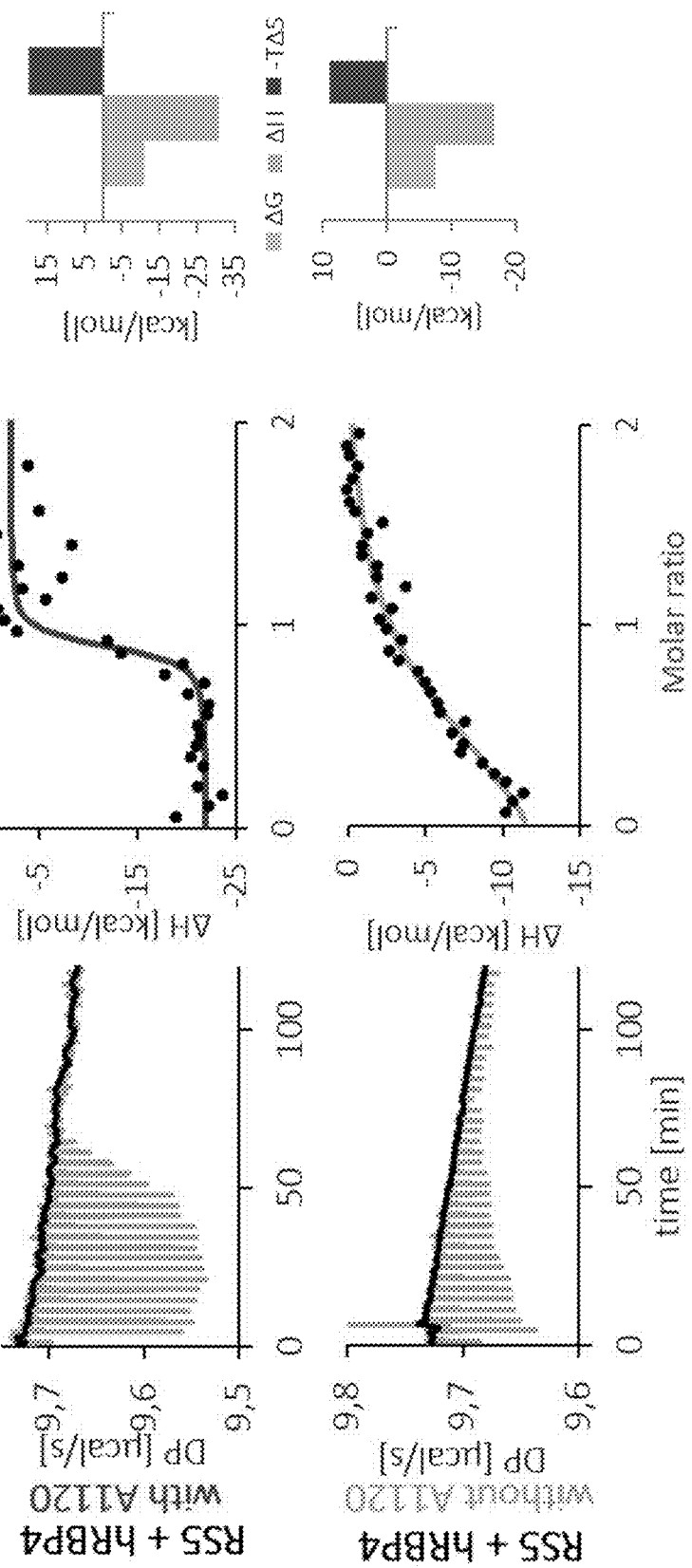
Figure 17C:
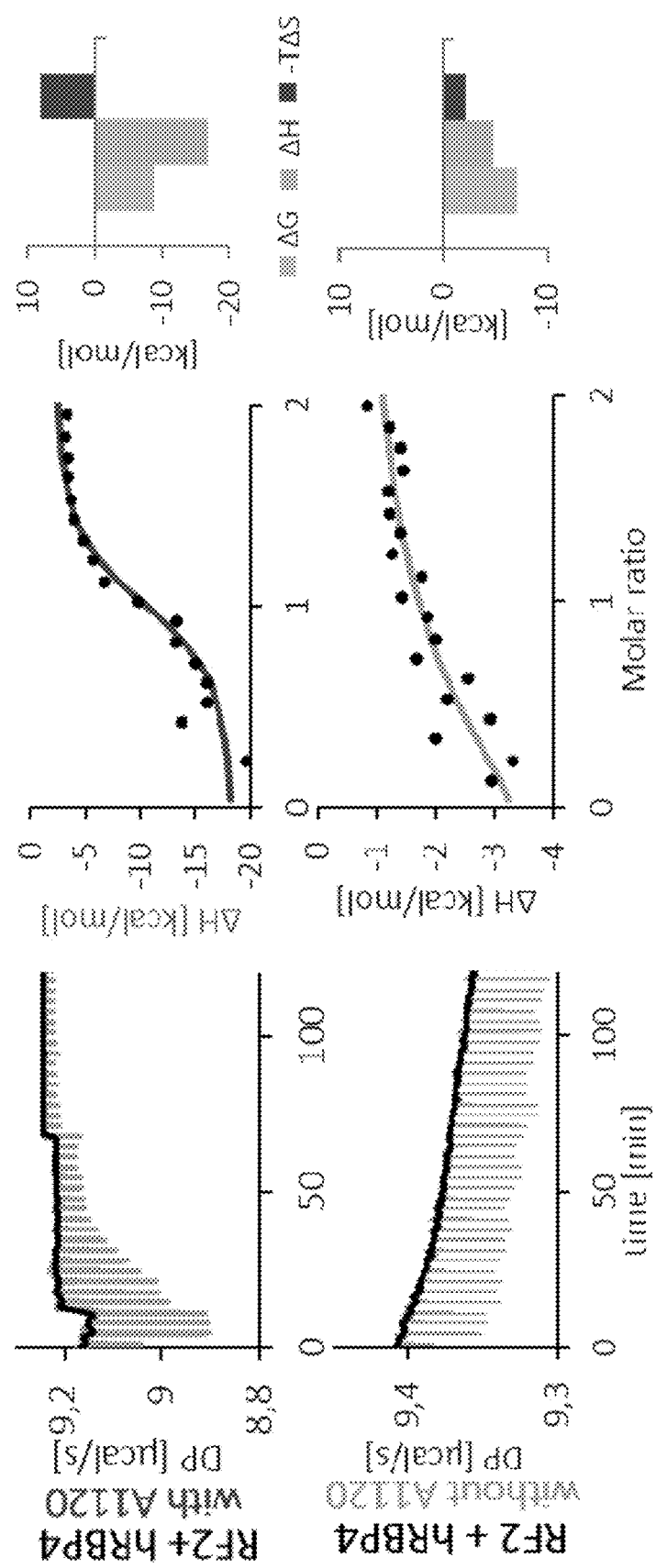

Furthermore, the affinities between RBP4 binding interaction partners (RS3, RS5 and RF2) and RBP4 were analyzed by isothermal titration calorimetry (ITC) and surface plasmon resonance (SPR). These measurements clearly demonstrated that the affinities of those lipocalin-fold binding interaction partners (in this case RS3, RS5 and RF2) to the lipocalin-fold molecule (in this case RBP4) strongly depend on the presence of the lipocalin-fold ligand (in this case A1120). FIGS. 15, 17 and 18 show that addition of the lipocalin-fold ligand A1120 increases the affinity between those lipocalin-fold binding interaction partners and the lipocalin-fold molecule RPB4 by up to several hundred-fold.

Characterization of RBP4 Binding Interaction Partners by DSC

Figure 14:
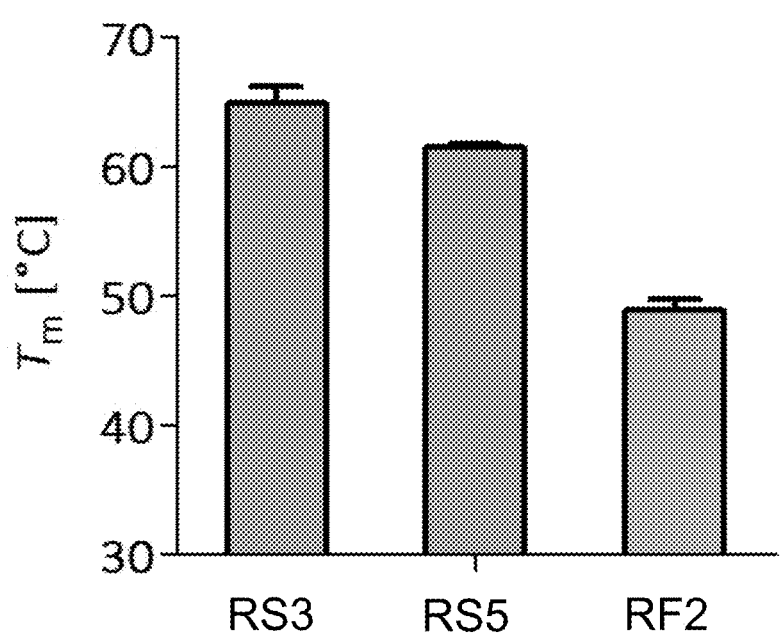
FIG. 14 shows analysis of RBP4 binding interaction partners RS3, RS5 and RF2 (in this case the lipocalin-fold binding interaction partners) by differential scanning calorimetry (DSC) for evaluation of the melting temperature ($T_m$).

The thermal stability of RBP4 binding interaction partners was evaluated by determining the melting temperature ($T_m$) by differential scanning calorimetry (DSC) using the PEAQ Differential Scanning Calorimeter Automated (Malvern Panalytical). Briefly, 80 μM protein solution was exposed to an increasing temperature ranging from 20-110° C. with a heating rate of 1° C./min. Buffer baseline was subtracted and the resulting data were normalized for protein concentration, followed by fitting with a non-two-state thermal unfolding model. FIG. 14 shows the determined $T_m$ values for the RBP4 binding interaction partners RS3, RS5 and RF2 (mean of 3 independent experiments+/−s.d.).

Characterization of the Interaction Between RBP4 Binding Interaction Partners and RBP4 by SPR Surface plasmon resonance (SPR) was used to determine the affinity of the interaction between RBP4 and rcSso7d- or FN3-based lipocalin-fold binding interaction partners and was performed with BiacoreT200 (GE Healthcare). The antigen (RBP4) was coated onto a CM5 chip (GE Healthcare) and incubated with various concentrations of lipocalin-fold binding interaction partner solution in HBS-EP (GE Healthcare), followed by a dissociation phase in HBS-EP. All measurements were performed both in the presence (5 μM) and absence of A1120. Finally, $K_d$ values (dissociation constants) were obtained by steady-state analysis. FIG. 15A shows a single-cycle kinetics (SCK) SPR experiment with RBP4 immobilized on a sensor chip and titrated with the lipocalin-fold binding interaction partner RS3 in the presence of 5 μM A1120. FIG. 15B shows an SCK experiment in the absence of A1120 with the same RS3 concentrations used in (A). Since almost no signal could be observed with these concentrations, they were elevated. FIG. 15C shows an SCK experiment with higher RS3 concentrations in the absence of A1120. $K_D$ values were calculated by steady-state analysis (right diagram in A and C). One representative experiment out of four independent experiments is shown.

Characterization of RBP4 Binding Interaction Partners by SEC

Figure 16:
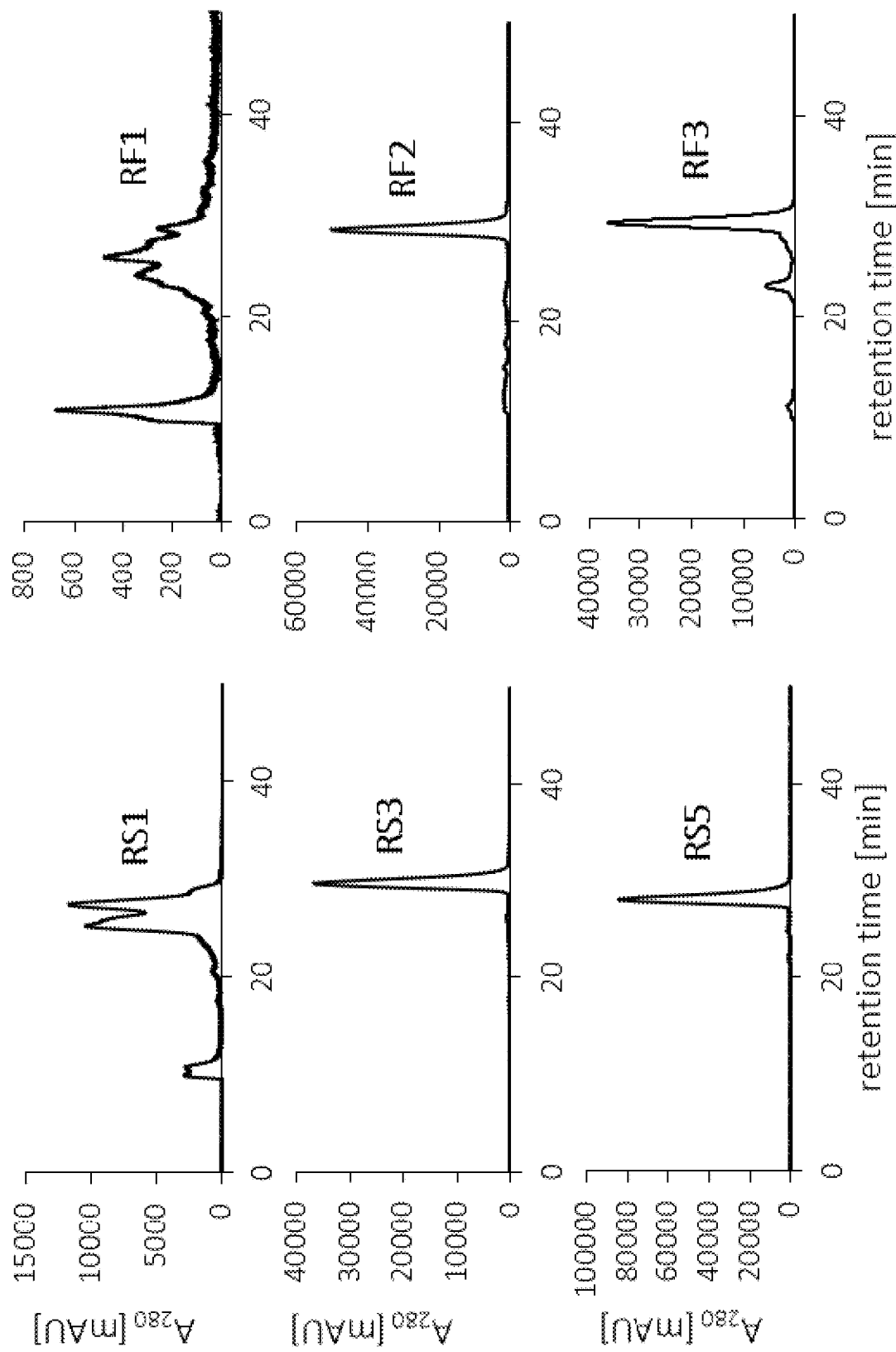
FIG. 16 shows the elution profiles of RBP4 binding interaction partners RS1, RS3, RS5, RF1, RF2 and RF3 analyzed by size exclusion chromatography (SEC).

For analytical SEC analysis, a total amount of 25 μg of RBP4 binding interaction partners in running buffer (PBS with 200 mM NaCl) was filtered through a 0.1 μm Ultrafree-MC filter (Merck Millipore), applied to a Superdex 200 10/300 GL column (GE healthcare) connected to an HPLC Prominence LC20 system (Shimadzu) and eluted with a flow rate of 0.75 mL/min at 25° C. FIG. 16 shows the elution profiles of 6 different RBP4 binding interaction partners (RS1, RS3, RS5, RF1, RF2 and RF3).

Characterization of the Interaction Between RBP4 Binding Interaction Partners and RBP4 by ITC For the thermodynamic characterization of the interaction between RBP4 and rcSso7d- or FN3-based lipocalin-fold binding interaction partners (in this case RBP4 binding interaction partners), isothermal titration calorimetry (ITC) was conducted using the PEAQ Isothermal Titration Calorimeter Automated (Malvern Panalytical). The samples were centrifuged (17000 g, 10 min, 20° C.) and dialysed against the same buffer (PBS). RBP4 protein solution was applied to the sample cell and the respective RBP4 binding interaction partners were titrated with varying intervals. Different concentrations both for RBP4 and RBP4 binding interaction partners were used. The experiments were performed both in the presence and absence of the lipocalin-fold ligand A1120. In the experiments where A1120 was present, the ligand was added both to the RBP4 protein and RBP4 binding interaction partner solution to achieve the same buffer compositions. Data analysis was performed with the MicroCal PEAQ-ITC analysis software and the resulting data were fitted to a one-set-of-sites binding model. FIG. 17A shows the analysis of the interaction of one RBP4 binding interaction partner (RS3) with RBP4 in the presence (50 μM) and absence of A1120 as determined by ITC. The integrated data were fitted to a one-set-of-sites binding model to calculate the $K_D$ values shown in FIG. 18. The signature plots show the thermodynamic parameters of the interaction between RBP4 and RS3. One representative experiment out of four independent experiments is shown. FIG. 17B shows binding of the RBP4 binding interaction partners RS5 and RF2 to RBP4 in the presence (50 µM) and absence of A1120. The integrated data were fitted to one-set-of-sites binding model to calculate the $K_D$ values in FIG. 18. Signature plots show the thermodynamic parameters of the interaction. One representative experiment out of four independent experiments is shown.

FIG. 18 summarizes the affinity measurements for RBP4 and the RBP4 binding interaction partners RS3, RS5 and RF2 by yeast surface display (n=3), SPR (n=4) and ITC (n=4). Mean values+/−s.d. are shown.

Example 5: Screening of Clinically Applicable Lipocalin-Fold Ligands with Capacity to Induce Conformational Switching in a Lipocalin-Fold Molecule The capacity of some of the ligands described in example 2 to induce conformational switching of RBP4 was detected by exploiting the conformation-dependent binding of TTR to RBP4. That is, if a lipocalin-fold ligand induces a conformational switch in RBP4, this can result in reduction (or elevation) of TTR affinity to RBP4, which can be detected by flow cytometric analysis of TTR binding.

Subcloning of RBP4 into the Vector pCTCON2 and Yeast Transformation

RBP4-encoding DNA was isolated from *P. pastoris* using the zymoprep yeast plasmid miniprep kit II (Zymo Research) followed by PCR amplification using the primers picZalpha_fwd (5'-ATTGCCAGCATTGCTGCTAAAGAAG-3') and picZalpha_rev (5'-GCAAATGGCATTCTGACATCC-3'). The DNA was purified using the Illustra GFX PCR DNA and Gel Band Purification Kit (GE healthcare) and sequenced. For cloning into the vector pCTCON2, the RBP4-encoding DNA was amplified by PCR using primers encoding NheI/BamHI restriction sites. After digestion with NheI and BamHI (both New England Biolabs), the RBP4 encoding sequence was ligated into the linearized vector and *E. coli* cells were electroporated with the resulting construct for verification of the sequence. The different parts of the resulting fusion protein have the order Aga2p—HA-tag—(Gly$_4$Ser)$_3$ Linker—RBP4—c-myc Tag. *S. cerevisiae* strain EBY100 was then transformed with the sequence-verified construct using the Quick and easy transformation kit (Takara).

Expression of RBP4 on the surface of yeast was induced by culturing the cells in SG-CAA medium (2 g/L glucose, 20 g/L galactose, 6.7 g/L yeast nitrogen base, 5 g/L casamino acids, 10.2 g/L disodium hydrogen phosphate and 4.82 g/L sodium phosphate monobasic) overnight at 20° C. and 180 rpm. For detection of RBP4 expression on the surface of yeast cells, cells were stained with either mouse anti-c-myc antibody 9E10 (Thermo Fisher Scientific) followed by secondary staining with anti-mouse IgG-AF488 (Thermo Fisher Scientific) or with anti-HA-Alexa Fluor 647 (BioLegend).

Expression and Purification of TTR

Human StrepII-tagged TTR was cloned into the pET52b+ vector and *E. coli* pLys cells were transformed with the construct. For the expression, LB medium (consisting of 10 g/L peptone, 5 g/L yeast extract and 5 g/L sodium chloride) containing ampicillin (100 µg/mL) was inoculated with *E. coli* cells containing the sequence-verified plasmid and cultivated overnight at 37° C. while shaking (180 rpm). Cells were diluted on the following morning and further cultivated until an OD$_{600}$ of 1 was reached. Induction of protein expression was performed by addition of IPTG (Isopropyl-β-D-thiogalactopyranoside, 1 mM). In addition, the temperature was decreased to 20° C. and cells were cultivated overnight at 180 rpm. Cells were harvested by centrifugation (5000 g, 15 min), the pellet was resuspended in lysis buffer (PBS supplemented with 150 mM NaCl, 10 mM imidazole, 5 mM β-mercaptoethanol, pH 7.4) and the protease inhibitor PMSF (Phenylmethylsulfonylfluoride, 1 mM) was added to prevent protein degradation. Cells were lysed by sonication (frequency 50 kHz, 2 times 90 s, amplitude: 5) using the Vibra Cell sonicator (Sonics & Materials Inc.) followed by centrifugation (10,000 g, 20 min). The supernatant was filtered through a 0.45 µm filter (Merck Millipore). A StrepTrap HP column (GE Healthcare) connected to an AKTA FPLC purifier system was equilibrated with binding buffer (PBS supplemented with 150 mM NaCl, pH 7.4) and the sample was applied with a flow rate of 1 mL/min. After washing with binding buffer, elution was performed with elution buffer (binding buffer with 2.5 mM desthiobiotin) and the fractions were analysed by NanoDrop and SDS-PAGE. Those fractions showing both absorbance at 280 nm and the presence of a protein band at the expected size were pooled and concentrated using Amicon Ultra-15 10K Centrifugal filters (Merck Millipore).

Flow Cytometric Detection of Lipocalin-Fold Ligand-Induced Conformational Switching of RBP4

Figure 19:
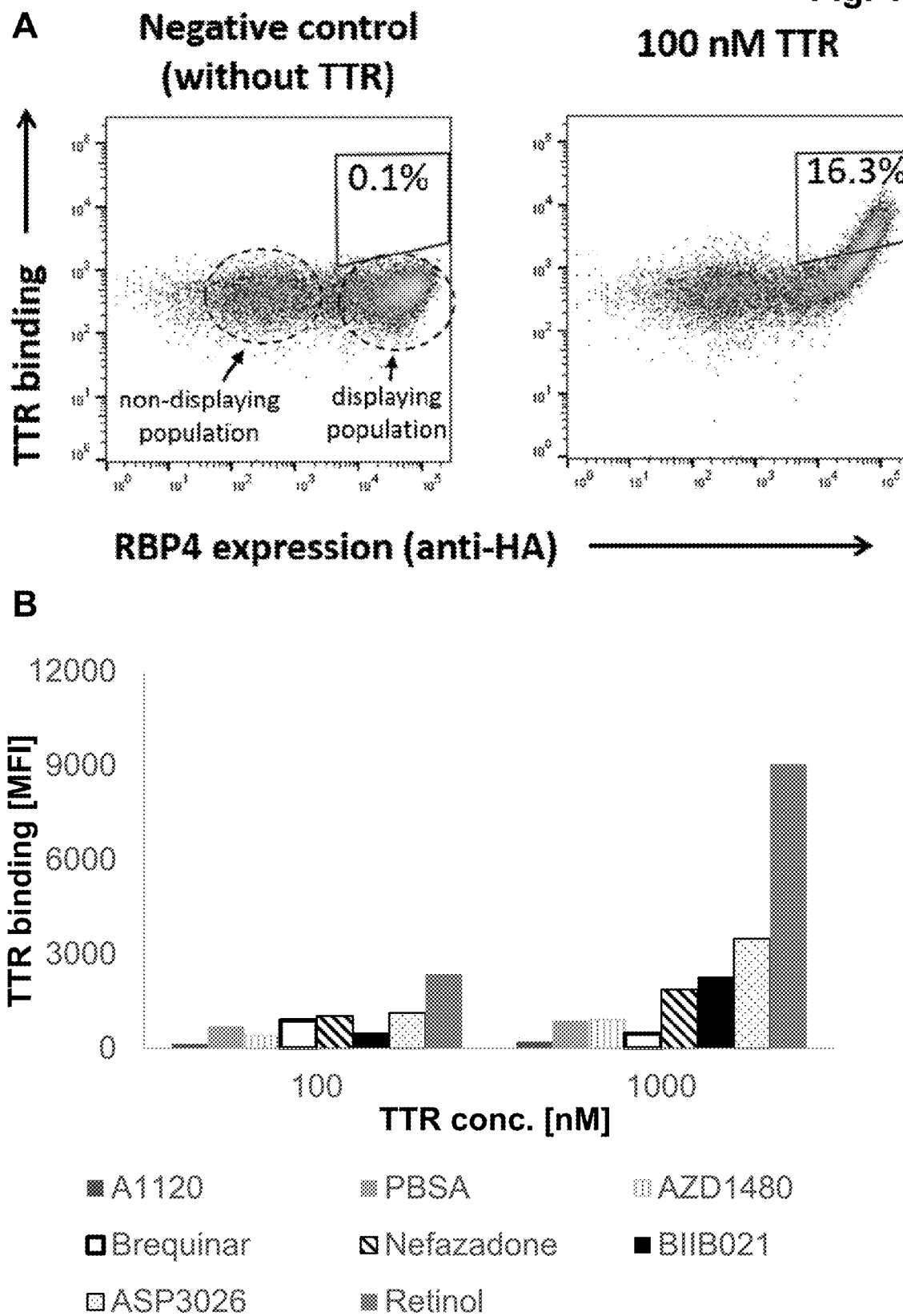
FIG. 19 in panel A shows binding of TTR to RBP4 displayed on the surface of yeast.

Flow cytometric detection of lipocalin-fold ligand induced conformational switching of RBP4 is based on employing the dependence of the RBP4-TTR interaction on the RBP4-conformation. For this purpose, 1×10$^6$ yeast cells displaying RBP4 were incubated with PBSA (PBS supplemented with 0.1% BSA) containing 100 µM of the potential lipocalin-fold ligand and incubated for 20 min at 4° C. while shaking. Afterwards, different concentrations of purified TTR (ranging between 0 and 1000 nM) were added in presence (50 µM) or absence of the potential lipocalin-fold ligand and incubated for 1 h at 4° C. while shaking. Two washing steps were performed followed by incubation (25 min at 4° C.) with a biotinylated anti-Strep II antibody (Genscript), which recognizes the StrepII-tagged TTR. After two washing steps, tertiary staining was performed using Streptavidin-PE (Biolegend) and anti-HA-Alexa Fluor 488 (Biolegend) and incubation for 25 min at 4° C. After two final washing steps, cells were kept as a pellet and resuspended in PBSA just before flow cytometric analysis. FIG. 19A shows dotplots from one representative experiment with stained yeast cells displaying RBP4 and binding to TTR. FIG. 19B shows single measurements of binding of TTR (Median fluorescence intensity) to RBP4 displayed on the surface of yeast in the presence of different potential lipocalin-fold ligands (50 µM) or in the absence of any lipocalin-fold ligand (PBSA).

Figure 20:
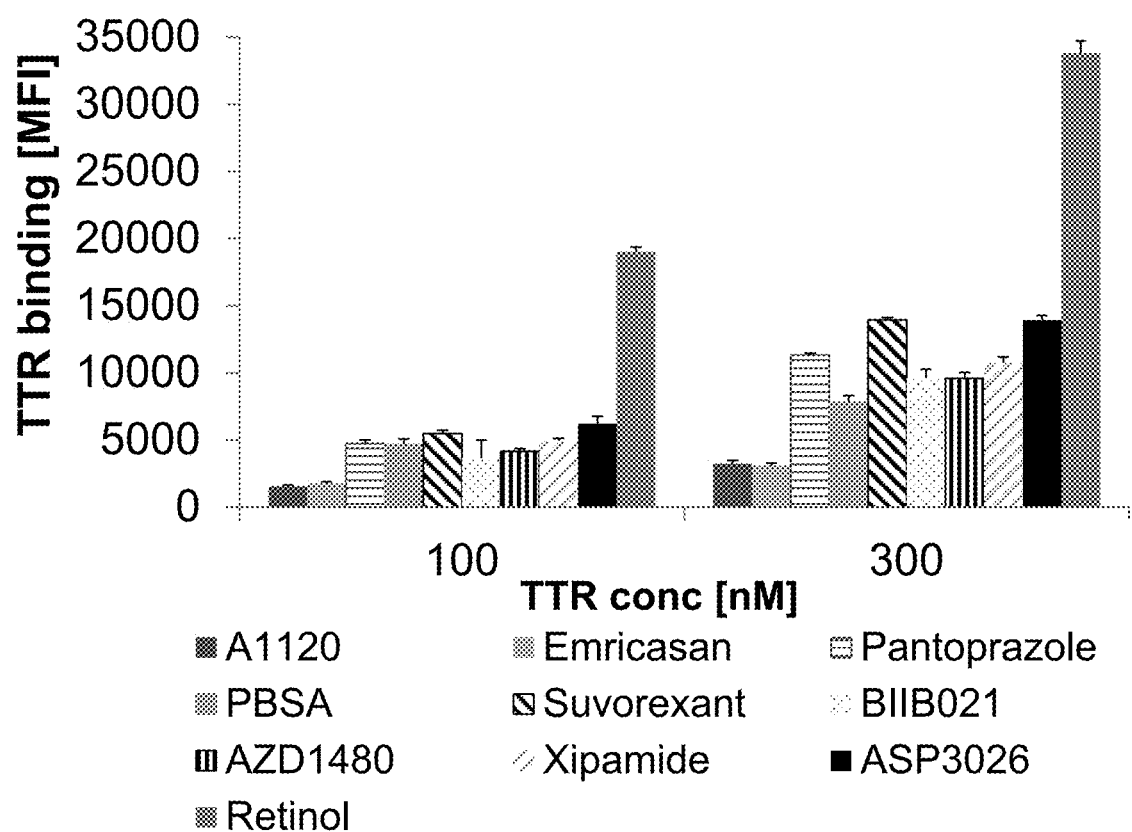
FIG. 20 shows binding of TTR to yeast-displayed RBP4 in the presence (50 µM) or absence (PBSA) of different potential lipocalin-fold ligands.

FIG. 20 shows binding of TTR (Median fluorescence intensity) to RBP4 displayed on the surface of yeast in the presence of various potential lipocalin-fold ligands (50 µM) or in the absence of any lipocalin-fold ligand (PBSA) at two different concentrations of TTR (100 and 300 nM). Mean values of triplicate measurements+/−s.d. are shown.

Accordingly, the present invention discloses the following preferred embodiments:

1. A ligand regulated protein-protein interaction system based on a lipocalin-fold molecule comprising:
   (a) a lipocalin-fold molecule
   (b) a lipocalin-fold ligand with a low molecular weight of 1500 Da or below, and
   (c) a lipocalin-fold binding interaction partner, wherein the lipocalin-fold molecule can bind to the lipocalin-fold ligand; and
wherein the lipocalin-fold molecule bound to the lipocalin-fold ligand binds to the lipocalin-fold binding interaction partner with an affinity which is at least 10-fold higher than the affinity of the lipocalin-fold molecule not bound to the lipocalin-fold ligand,
and wherein the lipocalin-fold binding interaction partner is not a naturally occurring protein which has an affinity of <10 µM to any naturally occurring lipocalin-fold molecule in the presence of any lipocalin-fold ligand.

2. A ligand regulated protein-protein interaction system based on a lipocalin-fold molecule comprising:
(a) a lipocalin-fold molecule
(b) a lipocalin-fold ligand with a low molecular weight of 1500 Da or below, and
(c) a lipocalin-fold binding interaction partner,
wherein the lipocalin-fold molecule has at least a first conformation when the lipocalin-fold ligand is not bound to the lipocalin-fold molecule and at least a second conformation when the lipocalin-fold ligand is bound to the lipocalin-fold molecule; and
wherein the lipocalin-fold molecule bound to the lipocalin-fold ligand in the second conformation binds to the lipocalin-fold binding interaction partner with an affinity which is at least 10-fold higher than the affinity of the lipocalin-fold molecule not bound to the lipocalin-fold ligand in the first conformation,
and wherein the lipocalin-fold binding interaction partner is not a naturally occurring protein which has an affinity of <10 µM to any naturally occurring lipocalin-fold molecule in the presence of any lipocalin-fold ligand.

3. A ligand regulated protein-protein interaction system according to embodiment 1 or 2, wherein the lipocalin-fold binding interaction partner does not contain any segment of at least 50 consecutive amino acids with an amino acid sequence that is at least 98% identical with the amino acid sequence of any segment of a naturally occurring protein which has an affinity of <10 µM to any naturally occurring lipocalin-fold molecule, especially in the presence of a lipocalin-fold ligand.

4. A ligand regulated protein-protein interaction system according to any one of embodiments 1 to 3, wherein the affinity of the lipocalin-fold binding interaction partner to the lipocalin-fold molecule when bound to the lipocalin-fold ligand or in the second conformation, respectively, is below 10 µM, preferably below 2 µM, especially below 400 nM.

5. A ligand regulated protein-protein interaction system according to any one of embodiments 1 to 4, wherein the lipocalin-fold binding interaction partner does not contain any segment of at least 50 consecutive amino acids with an amino acid sequence that is at least 98% identical with the amino acid sequence of any segment of a naturally occurring protein and wherein this segment of at least 50 consecutive amino acids has an affinity of <400 nM to any naturally occurring lipocalin-fold molecule, especially in the presence of a lipocalin-fold ligand.

6. A ligand regulated protein-protein interaction system according to any one of embodiments 1 to 4, wherein the lipocalin-fold binding interaction partner does not contain any segment of at least 50 consecutive amino acids with an amino acid sequence that is at least 98% identical with the amino acid sequence of any segment of a naturally occurring protein and wherein this segment of at least 50 consecutive amino acids has an affinity of <2 µM to any naturally occurring lipocalin-fold molecule, especially in the presence of a lipocalin-fold ligand.

7. A ligand regulated protein-protein interaction system according to any one of embodiments 1 to 4, wherein the lipocalin-fold binding interaction partner does not contain any segment of at least 50 consecutive amino acids with an amino acid sequence that is at least 98% identical with the amino acid sequence of any segment of a naturally occurring protein and wherein this segment of at least 50 consecutive amino acids has an affinity of <10 µM to any naturally occurring lipocalin-fold molecule, especially in the presence of a lipocalin-fold ligand.

8. A ligand regulated protein-protein interaction system according to any one of embodiments 1 to 7, wherein the lipocalin-fold binding interaction partner is not a homolog of a different species than human of a naturally occurring human lipocalin-fold binding interaction partner.

9. A ligand regulated protein-protein interaction system according to any one of embodiments 1 to 8, wherein the lipocalin-fold molecule is an artificial lipocalin-fold molecule which has no natural counterpart.

10. A ligand regulated protein-protein interaction system according to any one of embodiments 1 to 9, wherein the lipocalin-fold binding interaction partner is engineered to specifically recognize the lipocalin-fold molecule with higher affinity if the lipocalin-fold molecule is bound to the lipocalin-fold ligand compared to the affinity to the lipocalin-fold molecule not bound to the lipocalin-fold ligand, and wherein the lipocalin-fold molecule is optionally engineered for binding with higher affinity to the lipocalin-fold ligand.

11. A ligand regulated protein-protein interaction system according to any one of embodiments 1 to 10, wherein the lipocalin-fold molecule is not a homolog of a different species than human of a naturally occurring human lipocalin-fold molecule.

12. A ligand regulated protein-protein interaction system according to any one of embodiments 1 to 11, wherein the lipocalin-fold ligand is a pharmaceutically active molecule, especially a pharmaceutically active molecule with a therapeutic activity in human patients.

13. A ligand regulated protein-protein interaction system according to any one of embodiments 1 to 12, wherein the lipocalin-fold ligand is a molecule which can be effectively administered orally.

14. A ligand regulated protein-protein interaction system according to any one of embodiments 1 to 12, wherein the lipocalin-fold ligand is a molecule which can be effectively administered intravenously.

15. A ligand regulated protein-protein interaction system according to any one of embodiments 1 to 14, wherein the lipocalin-fold ligand is a molecule which can be effectively administered intravenously and/or orally to a human patient.

16. A ligand regulated protein-protein interaction system according to any one of embodiments 1 to 15, wherein the lipocalin-fold binding interaction partner does not contain a domain of a naturally occurring protein that mediates binding to a naturally occurring lipocalin-fold molecule with an affinity of <10 µM, especially in the presence of a lipocalin-fold ligand.

17. A ligand regulated protein-protein interaction system according to any one of embodiments 1 to 16, wherein the lipocalin-fold molecule is a molecule identical with a naturally occurring iLBP (intracellular lipid binding protein), a naturally occurring lipocalin or an anticalin, or is a derivative of any of these molecules with 1-30 amino acid exchanges and/or 1-50 amino acid deletions and/or 1-50 amino acid insertions.

18. A ligand regulated protein-protein interaction system according to any one of embodiments 1 to 17, wherein the lipocalin-fold molecule is a derivative of a naturally occurring or otherwise disclosed lipocalin-fold molecule with at least 70%, preferably at least 80%, especially at least 90% sequence identity in the β-barrel structure.

19. A ligand regulated protein-protein interaction system according to any one of embodiments 1 to 18, wherein the lipocalin-fold molecule is a derivative of a naturally occurring lipocalin or iLBP with at least one, two, three, four, five, six, seven, eight, nine, ten, 25 or 30 amino acid exchanges.

20. A ligand regulated protein-protein interaction system according to any one of embodiments 1 to 19, wherein the lipocalin-fold molecule is a derivative of a naturally occurring lipocalin or iLBP with up to 15, up to 30, or up to 50 amino acid deletions and/or up to 15, up to 30, or up to 50 amino acid insertions outside of the structurally conserved β-barrel structure, preferably corresponding structurally to the regions of amino acid residues selected from amino acid residues 1-20, 31-40, 48-51, 59-70, 79-84, 89-101, 110-113, 121-131 and 139-183 in human RBP4, which define the regions adjoining the structurally conserved β-strands in human RBP4 according to the amino acid residue numbering scheme in the PDB entry 1RBP;

amino acid residues 1-13, 24-36, 44-47, 55-61, 70-75, 80-83, 92-95, 103-110 and 118-158 in human TLC according to the amino acid residue numbering scheme in Schiefner et al., Acc Chem Res. 2015; 48 (4):976-985, which define the regions adjoining the structurally conserved β-strands in human TLC;

amino acid residues 1-43, 54-68, 76-80, 88-95, 104-109, 114-118, 127-130, 138-141 and 149-188 in human ApoM according to the amino acid residue numbering scheme in Schiefner et al., Acc Chem Res. 2015; 48(4):976-985, which define the regions adjoining the structurally conserved β-strands in human ApoM;

amino acid residues 1-4, 13-40, 46-49, 55-60, 66-70, 74-80, 88-92, 97-107, 113-118, 125-128 and 136-137 in human CRABPII according to the amino acid residue numbering scheme in PDB entry 2FS6, which define the regions adjoining the structurally conserved β-strands in human CRABPII;

amino acid residues 1-4, 13-38, 44-47, 53-58, 64-68, 72-78, 86-90, 95-98, 104-108, 115-118 and 126-127 in human FABP1 according to the amino acid residue numbering scheme in PDB entry 2F73, which define the regions adjoining the structurally conserved β-strands in human FABP1.

21. A ligand regulated protein-protein interaction system according to any one of embodiments 1 to 20, wherein the lipocalin-fold molecule is a derivative of a naturally occurring lipocalin or iLBP with at least 70%, preferably at least 80%, especially at least 90% sequence identity in the β-barrel structure, whereby this β-barrel structure is defined as the regions preferably corresponding structurally to the regions of amino acid residues selected from amino acid residues 21-30, 41-47, 52-58, 71-78, 85-88, 102-109, 114-120 and 132-138 in human RBP4 according to the amino acid residue numbering scheme in the PDB entry 1RBP, which define the structurally conserved β-strands in human RBP4;

amino acid residues 14-23, 37-43, 48-54, 62-69, 76-79, 84-91, 96-102 and 111-117 in human tear lipocalin (TLC) as defined by Schiefner et al., Acc Chem Res. 2015; 48(4):976-985, which define the structurally conserved β-strands in human TLC;

amino acid residues 44-53, 69-75, 81-87, 96-103, 110-113, 119-126, 131-137 and 142-148 in human apolipoprotein M (ApoM) as defined by Schiefner et al., Acc Chem Res. 2015; 48 (4):976-985, which define the structurally conserved β-strands in human ApoM;

amino acid residues 5-12, 41-45, 50-54, 61-65, 71-73, 81-87, 93-96, 108-112, 119-124 and 129-135 in human cellular retinoic acid binding protein II (CRABPII) according to the amino acid residue numbering scheme in PDB entry 2FS6, which define the structurally conserved β-strands in human CRABPII;

amino acid residues 5-12, 39-43, 48-52, 59-63, 69-71, 79-85, 91-94, 99-103, 109-114 and 119-125 in human fatty acid binding protein 1 (FABP1) according to the amino acid residue numbering scheme in PDB entry 2F73, which define the structurally conserved β-strands in human FABP1;

22. A ligand regulated protein-protein interaction system according to any one of embodiments 1 to 21, wherein the lipocalin-fold molecule is a fragment of a naturally occurring lipocalin or a derivative thereof with a length of at least 80, preferably at least 100, especially at least 120, amino acids covering at least the structurally conserved β-barrel structure of the lipocalin-fold, or wherein the lipocalin-fold molecule is a fragment of a naturally occurring iLBP or a derivative thereof with a length of at least 80, preferably at least 85, especially at least 90, amino acids covering at least the structurally conserved β-barrel structure of the lipocalin-fold, wherein the structurally conserved β-barrel structure comprises or consists of amino acid positions preferably corresponding structurally to the regions of amino acid residues selected from amino acid residues 21-30, 41-47, 52-58, 71-78, 85-88, 102-109, 114-120 and 132-138 in human RBP4 according to the amino acid residue numbering scheme in the PDB entry 1RBP, which define the structurally conserved β-strands in human RBP4;

amino acid residues 14-23, 37-43, 48-54, 62-69, 76-79, 84-91, 96-102 and 111-117 in human tear lipocalin (TLC) as defined by Schiefner et al., Acc Chem Res. 2015; 48(4):976-985, which define the structurally conserved β-strands in human TLC;

amino acid residues 44-53, 69-75, 81-87, 96-103, 110-113, 119-126, 131-137 and 142-148 in human apolipoprotein M (ApoM) as defined by Schiefner et al., Acc Chem Res. 2015; 48 (4):976-985, which define the structurally conserved β-strands in human ApoM;

amino acid residues 5-12, 41-45, 50-54, 61-65, 71-73, 81-87, 93-96, 108-112, 119-124 and 129-135 in human cellular retinoic acid binding protein II (CRABPII) according to the amino acid residue numbering scheme in PDB entry 2FS6, which define the structurally conserved β-strands in human CRABPII;

amino acid residues 5-12, 39-43, 48-52, 59-63, 69-71, 79-85, 91-94, 99-103, 109-114 and 119-125 in human fatty acid binding protein 1 (FABP1) according to the amino acid residue numbering scheme in PDB entry 2F73, which define the structurally conserved β-strands in human FABP1;

23. A ligand regulated protein-protein interaction system according to any one of embodiments 1 to 22, wherein the lipocalin-fold molecule bound to the lipocalin-fold ligand binds to the lipocalin-fold binding interaction partner with an affinity which is at least 20-fold higher, preferably at least 50-fold higher, than the affinity of the lipocalin-fold molecule not bound to the lipocalin-fold ligand.

24. A ligand regulated protein-protein interaction system according to any one of embodiments 1 to 23, wherein the lipocalin-fold molecule bound to the lipocalin-fold ligand binds to the lipocalin-fold binding interaction partner with an affinity which is at least 100-fold higher, preferably at least 200-fold higher, especially at least 500-fold higher, than the affinity of the lipocalin-fold molecule not bound to the lipocalin-fold ligand.

25. A ligand regulated protein-protein interaction system according to any one of embodiments 1 to 24, wherein the lipocalin-fold molecule bound to the lipocalin-fold ligand binds to the lipocalin-fold binding interaction partner with an affinity which is at least 1000-fold higher than the affinity of the lipocalin-fold molecule not bound to the lipocalin-fold ligand.

26. A ligand regulated protein-protein interaction system according to any one of embodiments 1 to 25, wherein the lipocalin-fold ligand has a molecular weight of 1500 to 75 Da, preferably of 750 Da to 150 Da.

27. A ligand regulated protein-protein interaction system according to any one of embodiments 1 to 26, wherein the lipocalin-fold binding interaction partner is or wherein the lipocalin-fold molecule and/or the lipocalin-fold binding interaction partner comprises an antigen, a cell surface receptor, an antibody, an antibody fragment, or a non-antibody based scaffold, preferably an affibody, a lipocalin-fold molecule, preferably an iLPB or a LCN, especially an anticalin; an avimer, a DARPin, a fynomer, a Kunitz domain, a knottin, a monobody, a Sso7d-based binder, reduced charge Sso7d (rcSso7d)-based binder or Sac7d-based binder.

28. A ligand regulated protein-protein interaction system according to any one of embodiments 1 to 27, wherein the lipocalin-fold binding interaction partner and/or the lipocalin-fold molecule comprises an antigen, a cell surface receptor, an antibody, an antibody fragment, or a non-antibody based scaffold, preferably an affibody, a lipocalin-fold molecule, preferably an iLPB or a LCN, especially an anticalin; an avimer, a DARPin, a fynomer, a Kunitz domain, a knottin, a monobody, a Sso7d-based binder, reduced charge Sso7d (rcSso7d)-based binder or Sac7d-based binder.

29. A ligand regulated protein-protein interaction system according to any one of embodiments 1 to 28, wherein the lipocalin-fold ligand has an affinity to the lipocalin-fold molecule of below 1 mM, preferably of below 100 μM, especially of below 10 μM.

30. A ligand regulated protein-protein interaction system according to any one of embodiments 1 to 29, wherein the lipocalin-fold ligand is a ligand selected from Table 1, especially fenretinide (15-[(4-hydroxyphenyl)amino]retinal), N-Ethylretinamide (PubChem CID: 5288173), all-trans retinoic acid (PubChem CID: 444795), axerophthene (PubChem CID: 5287722), A1120 (PubChem CID 25138295) and derivatives thereof, 1,4-butanediol (Pubchem CID: 8064), sphingosine-1-phosphate (Pubchem CID: 5283560), tetradecanoic acid (Pubchem CID: 11005), indicaxanthin (Pubchem CID: 6096870 and 12310796), vulgaxanthin I (Pubchem CID: 5281217), Montelukast (Pubchem CID: 5281040), Cyclandelate (Pubchem CID: 2893), Oxolamine (Pubchem CID: 13738), Mazaticol (PubchemCID: 4019), Butoctamid (Pubchem CID: 65780), Tonabersat (Pubchem CID: 6918324), Novazin (Pubchem CID: 65734), Diphenidol (Pubchem CID: 3055), Neobornyval, Erlotinib (Pubchem CID: 92131336), Tanespimycin (Pubchem CID: 6505803), LMI070 (Pubchem CID: 85471316), Alloclamide (Pubchem CID: 71837), Diacetolol (Pubchem CID: 50894), Acotiamide (Pubchem CID: 5282338), Acoziborole (Pubchem CID: 44178354), Acumapimod (Pubchem CID: 11338127), Apalutamide (Pubchem CID: 24872560), ASP3026 (Pubchem CID: 25134326), AZD1480 (Pubchem CID: 16659841), BIIB021 (Pubchem CID: 16736529), Branaplam (Pubchem CID: 89971189), Brequinar (Pubchem CID: 57030), Chlorproguanil (Pubchem CID: 9571037), Clindamycin (Pubchem CID: 446598), Emricasan (Pubchem CID: 12000240), Enasidenib (Pubchem CID: 89683805), Enolicam (Pubchem CID: 54679203), Flurazepam (Pubchem CID: 3393), ILX-295501 (Pubchem CID: 127737), Indibulin (Pubchem CID: 2929), Metoclopramide (Pubchem CID: 12598248), Mevastatin (Pubchem CID: 64715), MGGBYMDAPCCKCT-UHFFFAOYSA-N (Pubchem CID: 25134326), MK0686 (Pubchem CID: 16102897), Navarixin (Pubchem CID: 71587743), Nefazodone hydrochloride (Pubchem CID: 54911), Pantoprazole (Pubchem CID: 4679), Pavinetant (Pubchem CID: 23649245), Proxazole (Pubchem CID: 8590), Siccanin (Pubchem CID: 71902), Sulfaguanole (Pubchem CID: 9571041), Sunitinib (Pubchem CID: 5329102), Suvorexant (Pubchem CID: 24965990), Tiapride (Pubchem CID: 5467), Tonabersat (Pubchem CID: 6918324), VNBRGSXVFBYQNN-UHFFFAOYSA-N (Pubchem CID: 24794418), YUHNXUAATAMVKD-PZJWPPBQSA-N (Pubchem CID: 44548240), Ulimorelin (Pubchem CID: 11526696), Xipamide (Pubchem CID: 26618), Tropesin (Pubchem CID: 47530), Triclabendazole (Pubchem CID: 50248), Triclabendazole sulfoxide (Pubchem CID: 127657), Triclabendazole sulfone (Pubchem CID: 10340439) and Trametinib (Pubchem CID: 11707110).

31. A ligand regulated protein-protein interaction system according to any one of embodiments 1 to 30, wherein the lipocalin-fold molecule is part of an ectodomain of a chimeric antigen receptor and wherein the lipocalin-fold binding interaction partner is a cell surface antigen.

32. A ligand regulated protein-protein interaction system according to any one of embodiments 1 to 30, wherein the lipocalin-fold molecule and the lipocalin-fold binding interaction partner are parts of intra- and/or extracellular domains of a chimeric antigen receptor.

33. A ligand regulated protein-protein interaction system according to any one of embodiments 1 to 32, wherein the lipocalin-fold molecule is a lipocalin or a derivative thereof with 1-30 amino acid exchanges and/or 1-50 amino acid deletions and/or 1-50 amino acid insertions.
34. A ligand regulated protein-protein interaction system according to any one of embodiments 1 to 33, wherein the lipocalin-fold molecule has a sequence identity with human RBP4 of at least 95%.
35. A ligand regulated protein-protein interaction system according to any one of embodiments 1 to 33, wherein the lipocalin-fold molecule has a sequence identity with human tear lipocalin (TLC) of at least 95%.
36. A ligand regulated protein-protein interaction system according to any one of embodiments 1 to 33, wherein the lipocalin-fold molecule has a sequence identity with human apolipoprotein M (ApoM) of at least 95%.
37. A ligand regulated protein-protein interaction system according to any one of embodiments 1 to 36, wherein both, the lipocalin-fold molecule and the lipocalin-fold binding interaction partner are not part of a naturally occurring ligand regulated protein-protein interaction system.
38. A ligand regulated protein-protein interaction system according to any one of embodiments 1 to 37, wherein the lipocalin-fold ligand is selected from the group fenretinide (15-[(4-hydroxyphenyl)amino]retinal), N-Ethylretinamide (PubChem CID: 5288173), all-trans retinoic acid (PubChem CID: 444795), axerophthene (PubChem CID: 5287722), A1120 (PubChem CID 25138295) and derivatives thereof, 1,4-butanediol (Pubchem CID: 8064), sphingosine-1-phosphate (Pubchem CID: 5283560), tetradecanoic acid (Pubchem CID: 11005), indicaxanthin (Pubchem CID: 6096870 and 12310796), vulgaxanthin I (Pubchem CID: 5281217), Montelukast (Pubchem CID: 5281040), Cyclandelate (Pubchem CID: 2893), Oxolamine (Pubchem CID: 13738), Mazaticol (PubchemCID: 4019), Butoctamid (Pubchem CID: 65780), Tonabersat (Pubchem CID: 6918324), Novazin (Pubchem CID: 65734), Diphenidol (Pubchem CID: 3055), Neobornyval, Erlotinib (Pubchem CID: 92131336), Tanespimycin (Pubchem CID: 6505803), LMI070 (Pubchem CID: 85471316), Alloclamide (Pubchem CID: 71837), Diacetolol (Pubchem CID: 50894), Acotiamide (Pubchem CID: 5282338), Acoziborole (Pubchem CID: 44178354), Acumapimod (Pubchem CID: 11338127), Apalutamide (Pubchem CID: 24872560), ASP3026 (Pubchem CID: 25134326), AZD1480 (Pubchem CID: 16659841), BIIB021 (Pubchem CID: 16736529), Branaplam (Pubchem CID: 89971189), Brequinar (Pubchem CID: 57030), Chlorproguanil (Pubchem CID: 9571037), Clindamycin (Pubchem CID: 446598), Emricasan (Pubchem CID: 12000240), Enasidenib (Pubchem CID: 89683805), Enolicam (Pubchem CID: 54679203), Flurazepam (Pubchem CID: 3393), ILX295501 (Pubchem CID: 127737), Indibulin (Pubchem CID: 2929), Metoclopramide (Pubchem CID: 12598248), Mevastatin (Pubchem CID: 64715), MGGBYMDAPCCKCT-UHFFFAOYSA-N (Pubchem CID: 25134326), MK0686 (Pubchem CID: 16102897), Navarixin (Pubchem CID: 71587743), Nefazodone hydrochloride (Pubchem CID: 54911), Pantoprazole (Pubchem CID: 4679), Pavinetant (Pubchem CID: 23649245), Proxazole (Pubchem CID: 8590), Siccanin (Pubchem CID: 71902), Sulfaguanole (Pubchem CID: 9571041), Sunitinib (Pubchem CID: 5329102), Suvorexant (Pubchem CID: 24965990), Tiapride (Pubchem CID: 5467), Tonabersat (Pubchem CID: 6918324), VNBRGSXVFBYQNN-UHFFFAOYSA-N (Pubchem CID: 24794418), YUHNXUAATAMVKD-PZJWPPBQSA-N (Pubchem CID: 44548240), Ulimorelin (Pubchem CID: 11526696), Xipamide (Pubchem CID: 26618), Tropesin (Pubchem CID: 47530), Triclabendazole (Pubchem CID: 50248), Triclabendazole sulfoxide (Pubchem CID: 127657), Triclabendazole sulfone (Pubchem CID: 10340439) and Trametinib (Pubchem CID: 11707110).
39. A ligand regulated protein-protein interaction system according to any one of embodiments 1 to 38, wherein the lipocalin-fold molecule and the lipocalin-fold binding interaction partner are polypeptides.
40. A nucleic acid molecule comprising nucleotide sequences encoding the lipocalin-fold molecule and/or the lipocalin-fold binding interaction partner according to any one of embodiments 1 to 39, wherein the nucleic acid is preferably selected from DNA or RNA, more preferably in vitro transcribed RNA or RNA packaged in a retrovirus, especially RNA packaged in a lentivirus.
41. A kit of at least two nucleic acid molecules, wherein the first nucleic acid molecule comprises nucleotide sequences encoding the lipocalin-fold molecule according to embodiment 39 and wherein the second nucleic acid molecule comprises sequences encoding the lipocalin-fold binding interaction partner according to embodiment 39, wherein the nucleic acids are preferably selected from DNA or RNA, more preferably in vitro transcribed RNA or RNA packaged in a retrovirus, especially RNA packaged in a lentivirus.
42. A nucleic acid molecule or a kit of nucleic acid molecules according to embodiments 40 or 41, wherein the nucleic acid molecules are present in a vector and preferably packaged as DNA or RNA into an infectious virus particle.
43. A nucleic acid molecule or a kit of nucleic acid molecules according to any one of embodiments 40 to 42, wherein the nucleic acid sequences are linked to a sequence mediating strong and stable transgene expression in lymphocytes, wherein such a sequence preferably comprises the 5'-LTR of a gamma retrovirus or subelements R and U3 of a 5'-LTR of the Moloney murine leukaemia virus (MMLV) or the promoter of the murine stem cell virus (MSCV) or the promoter of phosphoglycerate kinase (PGK) or even more preferably the human elongation factor 1 (EF-1) alpha promoter.
44. A recombinant expression vector comprising the nucleic acid molecule according to embodiment 40 or the kit of nucleic acid molecules according to embodiment 41.
45. A kit of at least two recombinant expression vectors, wherein the first recombinant expression vector comprises a nucleic acid molecule encoding the lipocalin-fold molecule according to embodiment 40 and wherein the second recombinant expression vector comprises a nucleic acid molecule encoding the lipocalin-fold binding interaction partner according to embodiment 40.
46. A recombinant expression vector or a kit of at least two recombinant expression vectors, wherein the vector or at least one, preferably at least two, of the vectors comprise a T lymphocyte-specific promoter or an NK cell-specific promoter operably linked to the nucleotide sequences encoding the lipocalin-fold molecule and/or the lipocalin-fold binding interaction partner according to embodiment 39.

47. A vector comprising a nucleic acid molecule or a kit of nucleic acid molecules according to any one of embodiments 40 to 43.
48. A kit of at least two vectors comprising nucleic acid molecules according to any one of embodiments 41 to 43, wherein the first vector comprises a nucleic acid molecule encoding the lipocalin-fold molecule and wherein the second vector comprises a nucleic acid molecule encoding the lipocalin-fold binding interaction partner.
49. A vector or a kit of vectors according to embodiments 47 or
48, wherein a vector is a recombinant adeno-associated virus (rAAV) vector or a transposon vector, preferably a Sleeping Beauty transposon vector or PiggyBac transposon vector, or wherein a vector is a retroviral vector, preferably a gamma-retroviral vector or a lentiviral vector.
50. A vector or a kit of at least two vectors according to any one of embodiments 47 to 49, wherein the vector or at least one, preferably at least two, of the vectors are expression vectors, preferably expression vectors in which the nucleotide sequences encoding the lipocalin-fold molecule and/or the lipocalin-fold binding interaction partner according to any one of embodiments 1 to 39 are operably linked to a sequence mediating strong and stable transgene expression in lymphocytes, wherein such a sequence preferably comprises the 5'-LTR of a gamma retrovirus or subelements R and U3 of a 5'-LTR of the Moloney murine leukaemia virus (MMLV) or the promoter of the murine stem cell virus (MSCV) or the promoter of phosphoglycerate kinase (PGK) or even more preferably the human elongation factor 1 (EF-1) alpha promoter.
51. A cell genetically modified to produce the lipocalin-fold molecule and/or the lipocalin-fold binding interaction partner according to embodiment 39.
52. A cell genetically modified to produce the lipocalin-fold molecule and the lipocalin-fold binding interaction partner according to embodiment 39.
53. A cell modified in vitro or ex vivo with a nucleic acid molecule or a kit of nucleic acid molecules according to any one of embodiments 40 to 43 or with a vector or a kit of vectors according to any one of embodiments 47 to 50 to produce the lipocalin-fold molecule and/or the lipocalin-fold binding interaction partner according to any one of embodiments 1 to 39, or a kit comprising two or more of said modified cells.
54. A kit of at least two cells according to embodiment 53, wherein the first cell is genetically modified to produce the lipocalin-fold molecule according to embodiment 39 and wherein the second cell is genetically modified to produce the lipocalin-fold binding interaction partner according to embodiment 39.
55. A cell according to embodiment 53 or a kit of cells according to embodiments 53 or 54, wherein the cell is a prokaryotic or eukaryotic cell, preferably a mammalian cell, more preferably a hematopoietic stem cell, a progenitor cell, or a cell derived from a hematopoietic stem cell or a progenitor cell, especially a T cell or an NK cell.
56. A cell or a kit of cells according to any one of embodiments 53 to 55, wherein the cell is transfected or transformed with a vector or a kit of at least two vectors according to any one of embodiments 47 to 50.
57. A cell or kit of cells according to any one of embodiments 53 to 56, wherein the cell has stably integrated the nucleotide sequences encoding a lipocalin-fold molecule and/or a lipocalin-fold binding interaction partner into its genome.
58. A cell or kit of cells according to any one of embodiments 53 to 57, wherein the cell has stably integrated the nucleotide sequences encoding a lipocalin-fold molecule and/or a lipocalin-fold binding interaction partner into its genome by the use of site directed nuclease technology, preferably by the use of zinc finger nucleases or TALENs, or even more preferably CRISPR/Cas technology.
59. A cell transformed with a recombinant expression vector or a kit of at least two recombinant expression vectors according to any one of embodiments 44 to 46, preferably a mammalian cell, especially a T cell or an NK cell.
60. A pharmaceutical preparation comprising a nucleic acid molecule or a kit of nucleic acid molecules according to any one of embodiments 40 to 43, and/or a vector or a kit of vectors according to any one of embodiments 47 to 50, and/or a cell or a kit of cells according to any one of embodiments 53 to 58.
61. A pharmaceutical preparation according to embodiment 60, wherein the vectors are contained in infectious virus particles.
62. A method of making a cell according to any one of embodiments 53 to 58, the method comprising introducing into the cell, preferably stably integrating into the genome of the cell, in vitro or ex vivo a nucleic acid molecule or a kit of nucleic acid molecules according to any one of embodiments 40 to 43, or a vector or a kit of vectors according to any one of embodiments 47 to 50.
63. A non-human animal comprising a cell according to any one of embodiments 53 to 58.
64. A plant comprising a cell according to any one of embodiments 53 to 58.

The invention claimed is:

1. A ligand regulated protein-protein interaction system comprising:
(a) a lipocalin-fold molecule;
(b) a lipocalin-fold ligand with a low molecular weight of 1500 Da or below; and
(c) a lipocalin-fold binding interaction partner;
wherein the lipocalin-fold molecule can bind to the lipocalin-fold ligand; and
wherein the lipocalin-fold molecule bound to the lipocalin-fold ligand binds to the lipocalin-fold binding interaction partner with an affinity which is at least 10-fold higher than the affinity of the lipocalin-fold molecule not bound to the lipocalin-fold ligand;
and wherein the lipocalin-fold binding interaction partner is not a naturally occurring protein which has an affinity of <10 µM to any naturally occurring lipocalin-fold molecule in the presence of any lipocalin-fold ligand,
wherein the lipocalin-fold molecule is a lipocalin or a derivative thereof with 1-30 amino acid exchanges and/or 1-50 amino acid deletions and/or 1-50 amino acid insertions,
wherein the lipocalin-fold molecule is a derivative of a naturally occurring lipocalin with at least 70% sequence identity in the β-barrel structure, whereby this β-barrel structure is defined as the regions corresponding structurally to the regions of amino acid residues selected from
amino acid residues 21-30, 41-47, 52-58, 71-78, 85-88, 102-109, 114-120 and 132-138 in human RBP4 according to the amino acid residue numbering scheme in the PDB entry 1RBP, which define the structurally conserved ß-strands in human RBP4; and
amino acid residues 14-23, 37-43, 48-54, 62-69, 76-79, 84-91, 96-102 and 111-117 in human tear lipocalin (TLC), which define the structurally conserved ß-strands in human TLC.

2. A ligand regulated protein-protein interaction system comprising:
(a) a lipocalin-fold molecule;
(b) a lipocalin-fold ligand with a low molecular weight of 1500 Da or below; and
(c) a lipocalin-fold binding interaction partner;
wherein the lipocalin-fold molecule has at least a first conformation when the lipocalin-fold ligand is not bound to the lipocalin-fold molecule and at least a second conformation when the lipocalin-fold ligand is bound to the lipocalin-fold molecule; and
wherein the lipocalin-fold molecule bound to the lipocalin-fold ligand in the second conformation binds to the lipocalin-fold binding interaction partner with an affinity which is at least 10-fold higher than the affinity of the lipocalin-fold molecule not bound to the lipocalin-fold ligand in the first conformation,
and wherein the lipocalin-fold binding interaction partner is not a naturally occurring protein which has an affinity of <10 µM to any naturally occurring lipocalin-fold molecule in the presence of any lipocalin-fold ligand,
wherein the lipocalin-fold molecule is a lipocalin or a derivative thereof with 1-30 amino acid exchanges and/or 1-50 amino acid deletions and/or 1-50 amino acid insertions,
wherein the lipocalin-fold molecule is a derivative of a naturally occurring lipocalin with at least 70% sequence identity in the β-barrel structure, whereby this ß-barrel structure is defined as the regions corresponding structurally to the regions of amino acid residues selected from
amino acid residues 21-30, 41-47, 52-58, 71-78, 85-88, 102-109, 114-120 and 132-138 in human RBP4 according to the amino acid residue numbering scheme in the PDB entry 1RBP, which define the structurally conserved β-strands in human RBP4; and
amino acid residues 14-23, 37-43, 48-54, 62-69, 76-79, 84-91, 96-102 and 111-117 in human tear lipocalin (TLC), which define the structurally conserved ß-strands in human TLC.

3. The ligand regulated protein-protein interaction system according to claim 1, wherein the lipocalin-fold molecule is a derivative of a naturally occurring lipocalin with 1-30 amino acid exchanges and/or 1-50 amino acid deletions and/or 1-50 amino acid insertions.

4. The ligand regulated protein-protein interaction system according to claim 1, wherein the lipocalin-fold molecule is a derivative of a naturally occurring lipocalin with at least one, two, three, four, five, six, seven, eight, nine, ten, 25 or 30 amino acid exchanges.

5. The ligand regulated protein-protein interaction system according to claim 1, wherein the lipocalin-fold molecule is a derivative of a naturally occurring lipocalin with up to 15 amino acid deletions and up to 15 amino acid insertions outside of the structurally conserved β-barrel structure, corresponding structurally to the regions of amino acid residues selected from amino acid residues 1-20, 31-40, 48-51, 59-70, 79-84, 89-101, 110-113, 121-131 and 139-183 in human RBP4, which define the regions adjoining the structurally conserved β-strands in human RBP4 according to the amino acid residue numbering scheme in the PDB entry 1RBP;

amino acid residues 1-13, 24-36, 44-47, 55-61, 70-75, 80-83, 92-95, 103-110 and 118-158 in human TLC, which define the regions adjoining the structurally conserved β-strands in human TLC.

6. The ligand regulated protein-protein interaction system according claim 1, wherein the lipocalin-fold molecule is a derivative of a naturally occurring lipocalin with at least 870% sequence identity in the β-barrel structure or wherein the lipocalin-fold molecule is a derivative of a naturally occurring lipocalin with at least 90% sequence identity in the β-barrel structure.

7. The ligand regulated protein-protein interaction system according to claim 1, wherein the lipocalin-fold molecule is a fragment of a naturally occurring lipocalin or a derivative thereof with a length of at least 80 amino acids covering at least the structurally conserved β-barrel structure of the lipocalin-fold, wherein the structurally conserved β-barrel structure comprises or consists of amino acid positions corresponding structurally to the regions of amino acid residues selected from amino acid residues 21-30, 41-47, 52-58, 71-78, 85-88, 102-109, 114-120 and 132-138 in human RBP4 according to the amino acid residue numbering scheme in the PDB entry 1RBP, which define the structurally conserved ß-strands in human RBP4;

amino acid residues 14-23, 37-43, 48-54, 62-69, 76-79, 84-91, 96-102 and 111-117 in human tear lipocalin (TLC), which define the structurally conserved β-strands in human TLC.

8. The ligand regulated protein-protein interaction system according to claim 1, wherein the lipocalin-fold molecule bound to the lipocalin-fold ligand binds to the lipocalin-fold binding interaction partner with an affinity which is at least 20-fold higher than the affinity of the lipocalin-fold molecule not bound to the lipocalin-fold ligand.

9. The ligand regulated protein-protein interaction system according to claim 1, wherein the lipocalin-fold molecule bound to the lipocalin-fold ligand binds to the lipocalin-fold binding interaction partner with an affinity which is at least 100-fold higher than the affinity of the lipocalin-fold molecule not bound to the lipocalin-fold ligand.

10. The ligand regulated protein-protein interaction system according to claim 1, wherein the lipocalin-fold molecule bound to the lipocalin-fold ligand binds to the lipocalin-fold binding interaction partner with an affinity which is at least 1000-fold higher than the affinity of the lipocalin-fold molecule not bound to the lipocalin-fold ligand.

11. The ligand regulated protein-protein interaction system according to claim 1, wherein the lipocalin-fold ligand has a molecular weight of 1500 to 75 Da.

12. The ligand regulated protein-protein interaction system according to claim 1, wherein the lipocalin-fold binding interaction partner is or wherein the lipocalin-fold molecule and the lipocalin-fold binding interaction partner comprises an antigen, a cell surface receptor, an antibody, an antibody fragment, or a non-antibody based scaffold, an affibody, an avimer, a DARPin, a fynomer, a Kunitz domain, a knottin, a monobody, a Sso7d-based binder, reduced charge Sso7d (rcSso7d)-based binder or Sac7d-based binder.

13. The ligand regulated protein-protein interaction system according to claim 1, wherein the lipocalin-fold binding interaction partner and/or the lipocalin-fold molecule comprises an antigen, a cell surface receptor, an antibody, an antibody fragment, or a non-antibody based scaffold, a DARPin, a fynomer, a Kunitz domain, a knottin, a monobody, a Sso7d-based binder, reduced charge Sso7d (rcSso7d)-based binder or Sac7d-based binder.

14. The ligand regulated protein-protein interaction system according to claim 1, wherein the lipocalin-fold ligand has an affinity to the lipocalin-fold molecule of below 1 mM.

15. The ligand regulated protein-protein interaction system according to claim 1, wherein the lipocalin-fold ligand is a ligand selected from the group consisting of fenretinide (15-[(4-hydroxyphenyl)amino]retinal), N-Ethylretinamide (PubChem CID: 5288173), all-trans retinoic acid (PubChem CID: 444795), axerophthene (PubChem CID: 5287722), A1120 (PubChem CID 25138295) and derivatives thereof, 1,4-butanediol (Pubchem CID: 8064), sphingosine-1-phosphate (Pubchem CID: 5283560), tetradecanoic acid (Pubchem CID: 11005), indicaxanthin (Pubchem CID: 6096870 and 12310796), vulgaxanthin I (Pubchem CID: 5281217), Montelukast (Pubchem CID: 5281040), Cyclandelate (Pubchem CID: 2893), Oxolamine (Pubchem CID: 13738), Mazaticol (PubchemCID: 4019), Butoctamid (Pubchem CID: 65780), Tonabersat (Pubchem CID: 6918324), Novazin (Pubchem CID: 65734), Diphenidol (Pubchem CID: 3055), Neobornyval, Erlotinib (Pubchem CID: 92131336), Tanespimycin (Pubchem CID: 6505803), LMI070 (Pubchem CID: 85471316), Alloclamide (Pubchem CID: 71837), Diacetolol (Pubchem CID: 50894), Acotiamide (Pubchem CID: 5282338), Acoziborole (Pubchem CID: 44178354), Acumapimod (Pubchem CID: 11338127), Apalutamide (Pubchem CID: 24872560), ASP3026 (Pubchem CID: 25134326), AZD1480 (Pubchem CID: 16659841), BIIB021 (Pubchem CID: 16736529), Branaplam (Pubchem CID: 89971189), Brequinar (Pubchem CID: 57030), Chlorproguanil (Pubchem CID: 9571037), Clindamycin (Pubchem CID: 446598), Emricasan (Pubchem CID: 12000240), Enasidenib (Pubchem CID: 89683805), Enolicam (Pubchem CID: 54679203), Flurazepam (Pubchem CID: 3393), ILX-295501 (Pubchem CID: 127737), Indibulin (Pubchem CID: 2929), Metoclopramide (Pubchem CID: 12598248), Mevastatin (Pubchem CID: 64715), MGGBYMDAPCCKCT-UHFFFAOYSA-N (Pubchem CID: 25134326, having the structure 2-N-[2-methoxy-4-[4-(4-methylpiperazin-1-yl)piperidin-1-yl]phenyl]-4-N-(2-propan-2-ylsulfonylphenyl)-1,3,5-triazine-2,4-diamine), MK0686 (Pubchem CID: 16102897), Navarixin (Pubchem CID: 71587743), Nefazodone hydrochloride (Pubchem CID: 54911), Pantoprazole (Pubchem CID:

4679), Pavinetant (Pubchem CID: 23649245), Proxazole (Pubchem CID: 8590), Siccanin (Pubchem CID: 71902), Sulfaguanole (Pubchem CID: 9571041), Sunitinib (Pubchem CID: 5329102), Suvorexant (Pubchem CID: 24965990), Tiapride (Pubchem CID: 5467), Tonabersat (Pubchem CID: 6918324), VNBRGSXVFBYQNN-UHFFAOYSA-N(Pubchem CID: 24794418, having the structure N-[4-(2-amino-3-chloropyridin-4-yl)oxy-3-fluorophenyl]-4-ethoxy-1-(4-fluorophenyl)-2-oxopyridine-3-carboxamide), YUHNXUAATAMVKD-PZJWPPBQSA-N(Pubchem CID: 44548240, having the structure [(1R)-2-[(3S)-3-[[5-chloro-2-(tetrazol-1-yl)phenyl]methylcarbamoyl]-3,4-dihydropyrazol-2-yl]-1-(4-fluorophenyl)-2-oxoethyl] propanoate), Ulimorelin (Pubchem CID: 11526696), Xipamide (Pubchem CID: 26618), Tropesin (Pubchem CID: 47530), Triclabendazole (Pubchem CID: 50248), Triclabendazole sulfoxide (Pubchem CID: 127657), Triclabendazole sulfone (Pubchem CID: 10340439) and Trametinib (Pubchem CID: 11707110).

16. The ligand regulated protein-protein interaction system according to claim 1, wherein the lipocalin-fold molecule and the lipocalin-fold binding interaction partner are polypeptides.

17. A nucleic acid molecule comprising nucleotide sequences encoding the lipocalin-fold molecule according to claim 1, wherein the nucleic acid is selected from DNA or RNA packaged in a retrovirus.

18. A kit of at least two nucleic acid molecules, wherein the first nucleic acid molecule comprises nucleotide sequences encoding the lipocalin-fold molecule according to claim 16 and wherein the second nucleic acid molecule comprises sequences encoding the lipocalin-fold binding interaction partner according to claim 16, wherein the nucleic acids are selected from DNA or RNA.

19. A vector comprising the kit of nucleic acid molecules according to claim 18.

20. The kit of at least two vectors comprising nucleic acid molecules according to claim 18, wherein the first vector comprises a nucleic acid molecule encoding the lipocalin-fold molecule and wherein the second vector comprises a nucleic acid molecule encoding the lipocalin-fold binding interaction partner.

* * * * *